US012570975B2

(12) United States Patent
Lee et al.

(10) Patent No.: US 12,570,975 B2
(45) Date of Patent: Mar. 10, 2026

(54) COMPOSITION FOR DIAGNOSIS OR TREATMENT OF A CONDITION ASSOCIATED WITH INCREASED ACTIVITY OF EIF4E COMPRISING AN EIF4E INHIBITOR

(71) Applicant: SoVarGen Co., Ltd., Daejeon (KR)

(72) Inventors: Jeong Ho Lee, Daejeon (KR); Jang Keun Kim, Daejeon (KR); Byung Tae Kim, Daejeon (KR); Sun-Gyun Kim, Daejeon (KR)

(73) Assignee: SOVARGEN CO., LTD., Daejeon (KR)

( * ) Notice: Subject to any disclaimer, the term of this patent is extended or adjusted under 35 U.S.C. 154(b) by 813 days.

(21) Appl. No.: 17/422,160

(22) PCT Filed: Sep. 3, 2020

(86) PCT No.: PCT/KR2020/011877
§ 371 (c)(1),
(2) Date: Jul. 9, 2021

(87) PCT Pub. No.: WO2021/045538
PCT Pub. Date: Mar. 11, 2021

(65) Prior Publication Data
US 2022/0348916 A1 Nov. 3, 2022

(30) Foreign Application Priority Data

Sep. 3, 2019 (KR) ........................ 10-2019-0109090
Sep. 3, 2019 (KR) ........................ 10-2019-0109091

(51) Int. Cl.
| | |
|---|---|
| *C12N 15/113* | (2010.01) |
| *A61K 31/155* | (2006.01) |
| *A61P 25/08* | (2006.01) |
| *C12Q 1/6883* | (2018.01) |
| *G01N 33/68* | (2006.01) |

(52) U.S. Cl.
CPC .......... *C12N 15/113* (2013.01); *A61K 31/155* (2013.01); *A61P 25/08* (2018.01); *C12Q 1/6883* (2013.01); *G01N 33/6896* (2013.01); *C12N 2310/11* (2013.01); *C12N 2310/315* (2013.01); *C12N 2310/321* (2013.01); *C12N 2310/3231* (2013.01); *C12N 2320/30* (2013.01); *C12Q 2600/106* (2013.01); *C12Q 2600/158* (2013.01); *G01N 2800/2857* (2013.01); *G01N 2800/52* (2013.01)

(58) Field of Classification Search
CPC ..... C12Q 2600/158; G01N 2800/2857; G01N 2800/52; C12N 15/113; C12N 2310/11; C12N 2310/14; A61P 25/08
See application file for complete search history.

(56) References Cited

U.S. PATENT DOCUMENTS

| | | | |
|---|---|---|---|
| 7,601,700 B2 | 10/2009 | Dobie et al. | |
| 8,252,762 B2 | 8/2012 | Dean et al. | |
| 8,410,074 B2 * | 4/2013 | Dobie ..................... | A61P 35/00 |
| | | | 435/375 |
| 9,096,851 B2 | 8/2015 | Dean et al. | |
| 9,181,549 B2 | 11/2015 | Prakash et al. | |
| 9,200,285 B2 | 12/2015 | Gleave et al. | |
| 9,217,147 B2 | 12/2015 | Singh et al. | |
| 9,629,346 B2 | 4/2017 | Lee et al. | |
| 9,714,288 B2 | 7/2017 | Oestergaard et al. | |
| 9,856,474 B2 | 1/2018 | Singh et al. | |
| 10,174,318 B2 | 1/2019 | Dibble et al. | |
| 10,563,202 B2 | 2/2020 | Collard et al. | |
| 2009/0017103 A1 | 1/2009 | Adwan et al. | |
| 2009/0192106 A1 | 7/2009 | Dobie et al. | |
| 2009/0203765 A1 | 8/2009 | Bhanot et al. | |
| 2012/0283312 A1 | 11/2012 | Dobie et al. | |
| 2014/0343007 A1 | 11/2014 | Borden et al. | |
| 2014/0343123 A1 | 11/2014 | Prakash et al. | |
| 2017/0095497 A1 | 4/2017 | Boison et al. | |
| 2017/0119809 A1 | 5/2017 | Borden et al. | |
| 2018/0214452 A1 * | 8/2018 | Lee ..................... | A61K 31/436 |

FOREIGN PATENT DOCUMENTS

| | | | | |
|---|---|---|---|---|
| AU | 2018100078 A | 2/2018 | | |
| CN | 1852979 A1 | 10/2006 | | |
| CN | 106047879 A | * 10/2016 | ........... | A61K 31/713 |
| EP | 2 603 222 B1 | 10/2018 | | |
| JP | 2007-505627 | 3/2007 | | |
| JP | 2015-534990 | 12/2015 | | |
| KR | 10-0750788 B | 8/2007 | | |
| KR | 10-2014-0064982 A | 5/2014 | | |
| KR | 10-2016-0108814 A | 9/2016 | | |
| KR | 10-2016-0113516 A | 9/2016 | | |
| RU | 2585489 C2 | 5/2016 | | |

(Continued)

OTHER PUBLICATIONS

Lu et al., Jan. 18, 2016, "Targeting translation: elF4E as an emerging anticancer drug target" Molecular Medicine, 18; e2, p. 1-13 (Year: 2016).*
Satheesha et al., Feb. 14, 2011, "Response to mTOR inhibition: activity of elF4E predicts sensitivity in cell lines and acquired changes in elF4E regulation in breast cancer", Molecular Cancer, 10:19, p. 1-10 (Year: 2011).*
Coleman et al., Apr. 14, 2009, "Combined analysis of elF4E and 4E-binding protein expression predicts breast cancer survival and estimates elF4E activity" British Journal of Cancer, 100, p. 1393-1399 (Year: 2009).*
Uttam et al., Oct. 24, 2018, "elF4E-Dependent Translational Control: A Central Mechanism for Regulation of Pain Plasticity", Frontiers in Genetics, 9(470), p. 1-10 (Year: 2018).*

(Continued)

*Primary Examiner* — Soren Harward
*Assistant Examiner* — Jenna L Persons
(74) *Attorney, Agent, or Firm* — LEX IP MEISTER, PLLC

(57) ABSTRACT

The present discloses relates to a composition, a kit or a method using an elF4E inhibitor for diagnosis or treatment of a condition associated with increased activity of elF4E.

14 Claims, 47 Drawing Sheets

Specification includes a Sequence Listing.

(56)                    References Cited

FOREIGN PATENT DOCUMENTS

WO      WO 2001-096388 A2    12/2001
WO      WO 2001-096389 A2    12/2001
WO       WO 2005028628 A2     3/2005
WO      WO 2013/037043 A1     3/2013
WO      WO 2014/066304 A       5/2014
WO      WO 2014-070868 A1     5/2014
WO      WO 2014-124339 A2     8/2014

OTHER PUBLICATIONS

Tejada et al., 2009, "Eukaryotic Initiation Factors (eIF) 2α and 4E Expression, Localization, and Phosphorylation in Brain Tumors", J Histochemistry & Cytochemistry, 57(5), p. 503-512 (Year: 2009).*
Santini et al., Nov. 7, 2017, "Reducing eIF4E-eIF4G interactions restores the balancebetween protein synthesis and actin dynamicsin fragile X syndrome model mice", Science Signaling, p. 1-12 (Year: 2017).*
Lipton and Sahin, "The Neurology of mTOR", Oct. 22, 2014, Neuron, 84, p. 275-291). (Year: 2014).*
Chung et al., Jan. 12, 2023, "Comprehensive multi-omic profiling of somatic mutations in malformations of cortical development" Nature Genetics, 55(2), p. 209-220 (Year: 2023).*
Kim et al., Sep. 4, 2019, "Brain somatic mutations in MTOR reveal translational dysregulations underlying intractable focal epilepsy" Journal of Clinical Investigtion, 129(10), p. 4207-4223 (Year: 2019).*
Sare et al., Jan. 12, 2018, "Negative Effects of Chronic Rapamycin Treatment on Behavior in a Mouse Model of Fragile X Syndrome" 10(452), p. 1-11 (Year: 2018).*
NM_001122674.1, Homo sapiens ATP binding cassette subfamily D member 3 (ABCD3), transcript variant 2, mRNA, revised Oct. 20, 2018, retrieved Apr. 18, 2024 (Year: 2018).*
Larsson, Jun. 5, 2012, "Distinct perturbation of the translatome by the antidiabetic drug metformin" 109(23), p. 8977-8982 and Supporting Table S2 (Year: 2012).*
Homo sapiens eukaryotic translation initiation factor 4E (EIF4E), RefSeqGene on chromosome 4, NCBI Reference Sequence: NG_047048.2 (Year: 2019).*
Abend et al., 2013, Lancet Neurology, 12: 1170-79 (Year: 2013).*
Aartsma-Rus, 2009, Molecular Therapy, vol. 17, No. 3, p. 548-553 (Year: 2009).*
Chan et al., 2006, CEPP, 33, p. 533-540 (Year: 2006).*
Partial Supplementary Search Report issued in European Patent Application No. 20861342.2 mailed on Jan. 4, 2024.
Culjkovic, Biljana et al., "Understanding and Targeting the Eukaryotic Translation Initiation Factor eIF4E in Head and Neck Cancer," Journal of Oncology, 189 (4) pp. 1-12 (2009).
Thumma, SC et al., "Antisense oligonucleotide targeting eukaryotic translation initiation factor 4E reduces growth and enhances chemosensitivity of non-small-cell lung cancer cells," Cancer Gene Therapy, 22, pp. 396-401 (2015).
Boer, Karin et al., "Pi3K-mTOR Signaling and AMOG Expression in Epilepsy-associated Glioneuronal Tumors," Brain Pathology, 20, pp. 234-244 (2010).
Theofilas, Panos et al., "Adenosine Kinase as a target for therapeutic antisense strategies in epilepsy," Epilepsia, 52(3), pp. 589-601 (2011).

Chan, Wai-Yee et al., "The complexity of antisense transcription revealed by the study of developing male germ cells," Genomics, 87, pp. 681-692 (2006).
Lapidot, Michael et al., "Genome-wide natural antisense transcription coupling its regulation to its different regulatory mechanisms," EMBO Reports, vol. 7, No. 12, 1216-1222 (2006).
Office Action issued in Russian Patent Application No. 2022107375 dated Apr. 7, 2023.
Search Report issued in Russian Patent Application No. 2022107375 dated Apr. 7, 2023.
Blümcke et al., "The clinicopathologic spectrum of focal cortical dysplasias: A consensus classification proposed by an ad hoc Task Force of ht eILAE Diagnostic Methods Commission," Epilepsia 52, 158-174 (2011).
Martinez-Sáez et al., "peIF4E as independent prognostic factor and a potential therapeutic target in diffuse infiltrating astrocytomas," Cancer Med., 5(9): 2501-2512 (2016).
Uttam et al, "eIF4E-Dependent Translational Control: A Central Mechanism for Regulation of Pain Plasticity," Frontiers in Genetics, vol. 9, Article 470 (2018).
Bailey TL et al., "Fitting a mixture model by expectation maximization to discover motifs in biopolymers," Proc. Second Int. Conf. Intell. Syst. Mol. Biol., 28-36 (1994).
Astrinidis, A. et al., "Tuberous sclerosis complex: linking growth and energy signaling pathways with human disease", Oncogene, 24, pp. 7475-7481 (2005).
Parsyan, Armen, "Translation and Its Regulation in Cancer Biology and Medicine," SpringerLink (2020).
Chen, C. et al, "Therapeutic inhibition of mTOC2 rescues the behavioral and neurophysiological abnormalities associated with Pten-deficiency," Nature Medicine, vol. 25, pp. 1684-1690 (2019).
Hsieh A. C. et al., "The translational landscape of mTOR signaling steers cancer initiation and metastasis," Nature, vol. 485, (2012).
Amorim I. S. et al., "The Role of the Eukaryotic Translation Initiation Factor 4E (eLF4E) in Neuropsychiatric Disorders," Frontiers in Genetics, vol. 9, Article 561 (2018).
Lu et al., "Targeting translation: eIF4E as an emerging anticancer drug target," Molecular Medicine, vol. 18 (2016).
Kim, J. K. et al., "Brain somatic mutations in MTOR reveal translational dysregulations underlying intractable focal epilepsy," J Clin Invest (2019).
Salehi, Z. et al, "Expression of Eukaryoteic Initiation Factor 4E in the Children with Medulloblastoma," Pediatric Research, 70, 206 (2011).
Benedetti, A. D., et al., "eIF-4E expression and its role in malignancies and metastases," Oncogene, 23, pp. 3189-3199 (2004).
Mühlebner, A. et al., "New insights into a spectrum of developmental malformations related to mTOR dysregulations: challenges and perspectives," J. Anat. 235 pp. 521-542 (2019).
Pernice, H. F., "mTOR and MAPK: from localized translation control to epilepsy," bmc Neurosci, 17:73 (2016).
Lee, J. H., et al., "De novo somatic mutations in components of the PISK-AKT3-mTOR pathway cause hemimegalencephaly," Nature Genetics, vol. 44, No. 8 (2012).
Graff, J. R., "Therapeutic suppression of translation initiation factor eIF4E expression reduces tumor growth without toxicity," J. Clin Invest., 117(9), pp. 2638-2648 (2007).
International Search Report from PCT/KR2020/011877 dated Mar. 11, 2021 (translation).
Written Opinion from PCT/KR2020/011877 dated Mar. 11, 2021 (Machine Translation from WIPO included).

* cited by examiner

WT          p.C1483Y        p.L2427P

Scale bar = 25 um

FIG. 9d

ACAWYAGC motif e = 6.8-003

| Name | p-value | Motif Locations |
|------|---------|-----------------|
| ASO27 | 3.58e-3 | + |
| ASO35 | 3.94e-3 | + |
| ASO147 | 2.40e-2 | + |
| ASO180 | 3.76e-3 | + |
| ASO178 | 2.16e-2 | + |
| ASO179 | 3.76e-3 | + |
| ASO28 | 3.98e-2 | + |
| ASO182 | 7.77e-3 | + |

| Motif | Symbol | Motif Consensus |
|-------|--------|-----------------|
| 1. | | ACAWYAGC |
| 2. | | DCWHYA |
| 3. | | BYDMMR |

| [Inhibitor] vs. normalized response | ASO #75 | ASO #77 | ASO #35 | ASO #21 | ASO #27 | ASO #182 |
|---|---|---|---|---|---|---|
| IC50 (nM) | 93.93 | 53.82 | 22.77 | 86.69 | 92.45 | 91.07 | qPCR

HEK293T cell
n=4
MM: mismatch control
One ANOVA (Bonferroni's post hoc test

Body weight

A-dyskinesia

B-open field test

C-light & dark test

D-social avoidance test

E-3-chamber test (Social interaction test)   F-marble burying test

G-sucrose preference test

E-3-chamber test (Social interaction test)   F-marble burying test

G-sucrose preference test

A-dyskinesia

B-open field test

C-light & dark test

D-social avoidance test

E-3-chamber test (Social interaction test)    F-marble burying test

G-sucrose preference test

COMPOSITION FOR DIAGNOSIS OR TREATMENT OF A CONDITION ASSOCIATED WITH INCREASED ACTIVITY OF EIF4E COMPRISING AN EIF4E INHIBITOR

INCORPORATION-BY-REFERENCE OF MATERIAL SUBMITTED ELECTRONICALLY

Incorporated by reference in its entirety herein is a computer-readable nucleotide/amino acid sequence listing submitted concurrently herein and identified as follows: One 49,962 Byte ASCII (Text) file named "513386 ST25.txt", created Mar. 31, 2022.

BACKGROUND OF THE INVENTION

Field of the Invention

The present discloses relates to a composition comprising an eIF4E inhibitor for diagnosis or treatment of a condition associated with increased activity of eIF4E and, more specifically, to a composition for prevention, alleviation, reduction, or treatment of a condition associated with increased activity of eIF4E, for example, a disease or a disorder associated with increased activity of eIF4E, symptoms thereof, and an associated disease thereof.

Description of the Related Art eIF4E is a 24-kDa protein functioning as a eukaryotic translation initiation factor that plays an important role in the initiation of mRNA translation. Upon the initiation of mRNA translation, eIF4E binds to the 7-methylguanosine cap structure on the 5'-end of mRNA, which results in the recruitment of the scaffolding protein eIF4G and the helicase eIF5A to form a complex (termed eIF4F). Assembly of the complex is necessary for the initiation of cap-dependent translation. Thus, the binding of eIF4E to eIF4G is a critical process in the translation. The assembly of the eIF4F complex is a rate-limiting step in translation initiation and is dependent on the availability of eIF4E.

The availability of eIF4E for assembly into the eIF4F complex is regulated by the repressor proteins, called eIF4E-binding proteins (4E-BPs: 4E-BP1/2/3), and binding of the 4E-BP1/2/3 to eIF4E is controlled by the phosphorylation status of 4E-BPs. In a normal condition, eIF4E is bound to 4E-BPs and restrained from binding to the 7-methylguanosine cap on the 5'-end of the mRNA. However, when phosphorylated, 4E-BP1/2/3 functionally weakens. As a result, eIF4E against which 4E-BP1/2/3(4E-BPs) act as an inhibitor become active.

WO2001/096388 and WO2001/096389 introduce a nucleic acid molecule encoding a human eIF4E, disclosing cancer therapy that is achieved by administering the polynucleotide composition to cancer patients.

It was previously described that overexpression and activation of eIF4E in mice selectively enhanced the translation of growth promoting genes such as ODC, cyclin D1, c-myc, etc., thereby inducing cellular transformation, tumorigenesis, tumor invasiveness, and tumor metastasis. Particularly, increased expression and activation of eIF4E in cancer enhances the translation of genes involved in growth promotion to increase cell growth and provoke oncogenesis and metastasis. Elevated expression of eIF4E is known to associate with oncogenesis and play a role in the progression of leukemia, lymphoma, breast cancer, colorectal cancer, bladder cancer, lung cancer, prostate cancer, and head and neck cancer (Oncogene. 2004 Apr. 19; 23(18):3189-99, eIF-4E expression and its role in malignancies and metastases).

In addition, the upregulated expression of eIF4E is found in cancer, enhancing angiogenesis and tumor growth. eIF4E inhibitors downregulate the expression of eIF4E and decrease the expression of the oncogenes c-myc and cyclin D1 and the anti-apoptotic proteins surviving and Bcl-2. Thus, eIF4E inhibitors are known to induce apoptosis in tumor cells and reduce cell viability in tumor cells (J. Clin. Invest. 117:2638-2648, 2007). Conventionally, the expression of eIF4E was therefore a target of studies on hyperproliferative disorders, such as angiogenesis or solid cancers.

SUMMARY OF THE INVENTION

The present disclosure is drawn to a composition comprising an eIF4E inhibitor for diagnosis or treatment of a condition associated with increased activity of eIF4E, or a kit or a method therefor.

An embodiment of the present invention provides a composition comprising an eIF4E inhibitor as an active ingredient for prevention, alleviation, or treatment of a brain disease associated with increased activity of eIF4E, for example, FMCD (Focal Malformation of Cortical Development), symptoms of FMCD, or an associated disease thereof, or a kit or a method therefor.

Another embodiment of the present invention provides a method for prevention, alleviation, or to treatment of a disease associated with increased activity of eucaryotic translation initiation factor 4E (eIF4E) in brain neuronal cells or nervous tissues or a symptom thereof, the method comprising a step of administering an eIF4E inhibitor to a subject in need thereof.

An additional embodiment of the present disclosure provided a biomarker for diagnosis of a brain disease associated with increased activity of eIF4E, for example, FMCD, symptoms of FMCD, or an associated disease thereof, wherein the biomarker is at least one selected from the group consisting of eIF4E, eIF4E activation-sensitive proteins the expression or activity of which is regulated by eIF4E, and nucleic acid molecules coding therefor.

Another embodiment of the present invention provides a composition or kit for diagnosis of a brain disease associated with increased activity of eIF4E, for example, FMCD, symptoms of FMCD, or an associated disease thereof, the composition or kit comprising a molecule or agent capable of detecting at least one biomarker selected from the group consisting of eIF4E, eIF4E activation-sensitive proteins the expression or activity of which is regulated by eIF4E, and nucleic acid molecules coding therefor, or a method for diagnosis of a brain disease associated with increased activity of eIF4E, for example, FMCD, symptoms of FMCD, or an associated disease thereof or a method for providing diagnostic information on a brain disease associated with increased activity of eIF4E, for example, FMCD, symptoms of FMCD, or an associated disease thereof, the method using a molecule or agent capable of detecting at least one biomarker selected from the group consisting of eIF4E, eIF4E activation-sensitive proteins the expression or activity of which is regulated by eIF4E, and nucleic acid molecules coding therefor. The molecule or agent capable of detecting a biomarker may be a primer, a probe, or an aptamer which are all hybridizable with the biomarker, or an antibody or an aptamer that each bind specifically to the biomarker protein.

Another embodiment of the present invention provides a method for selecting a subject to be administered an eIF4E inhibitor, for predicting susceptibility of a subject to an eIF4E inhibitor, or for monitoring administration efficacy of an eIF4E inhibitor in a subject, the method using at least one biomarker selected from the group consisting of eIF4E, eIF4E activation-sensitive proteins the expression or activity of which is regulated by eIF4E, and a nucleic acid molecule coding therefor.

As used herein, the term "pharmaceutically acceptable salt" refers to a physiologically and pharmaceutically acceptable salt of a compound according to the present disclosure, that is, a salt that retains the desired biological activity of the parent compound and does not impart undesirable toxicological effects.

As used herein, the term "diagnosis" is intended to encompass identifying the presence or characteristic of a pathological condition, determining the onset of a pathological condition, detecting or probing risk or possibility of pathogenesis, and monitoring a pathological condition.

The term "treatment", as used herein, is intended to encompass alleviating or relieving a condition, a disease, a disorder, or a symptom thereof, reducing an extent of a disease, delaying or deterring the progression of a disease, ameliorating, alleviating, or stabilizing the state of a disease, partial or complete recovery, prolonging survival, or other beneficial outcomes. Herein, "treatment" encompasses the relief, alleviation, reduction, or treatment of a condition associated with increased activity of eIF4E (e.g., a disease, a disorder, a symptom thereof, or an associated disease thereof) by administering an eIF4E inhibitor to a patient suffering therefrom.

Meant by the term "subject" herein is a human or non-human animal that is selected for diagnosis, alleviation, prevention, or treatment. The subject may be a human or an animal that suffers from an eIF4E activity-induced brain disease, for example, FMCD, a symptom of FMCD, or an associated disease thereof, has risk or possibility of onset of the disease, or has undergone surgery for a lesion of the disease.

The subject may be a subject in need of preventing, alleviating, or treating a disease associated with increased activity of eIF4E in a brain neuronal cell or nervous tissue or a symptom thereof, for example, may have a brain disease caused by increased expression, intracellular level, or activity of eIF4E, a symptom thereof, or an associated disease thereof, or may undergo a change in the expression or activity of an upstream gene in the PI3K-AKT-mTOR signaling pathway in a brain neuronal cell or nervous tissue, the upstream gene inducing the activation of an eIF4E activation-sensitive gene the expression of activation of which is regulated by eIF4E, or the activation of eIF4E. The eIF4E activation-sensitive gene is activated by increased activity of eIF4E and includes a motif regulated by eIF4E in the 5'-untranslated region thereof, for example, at least one motif selected from a U-rich motif, a guanine quartet motif, an A-rich motif, and a CERT motif in the 5'-untranslated region. Concrete examples of the gene are listed in Table 1, below.

The eIF4E inhibitor may be to inhibit or reduce the activity, expression, or level of IF4E. In detail, the eIF4E inhibitor may function to suppress the production and/or expression of eIF4E or inhibit the activity of eIF4E, for example, may be a drug, an antibody, an shRNA, an siRNA, a microRNA, an antisense oligonucleotide, etc. which are all inhibitory of eIF4E. An inhibitor against the mRNA expression of eIF4E mRNA, for example, a substance complementarily binding to IF4E, e.g., a drug, an antibody, an siRNA, an shRNA, a microRNA, an antisense oligonucleotide, which all inhibit eIF4E, fall within the scope of the present disclosure.

An embodiment of the present disclosure pertains to an antisense oligonucleotide inhibiting the activity or expression of eucaryotic translation initiation factor 4E and having a length of 14 to 30, 15 to 30, 16 to 30, 17 to 30, 18 to 30, or 19 to 30 nucleotides. More specifically, the antisense oligonucleotide may be an antisense nucleic acid molecule hybridizing specifically with at least one selected from a 5'-untranslated region, an initiation region, an exon, an intron, and a 3'-untranslated region in eIF4E.

An embodiment of the present disclosure provides a composition or a kit comprising the antisense oligonucleotide as an eIF4E inhibitor for diagnosis, prevention, alleviation, or treatment of a brain disease associated with increased activity of eIF4E, for example, FMCD (Focal Malformation of Cortical Development), a symptom of FMCD, or an associated disease thereof, or a method using the antisense oligonucleotide as an eIF4E inhibitor for diagnosis, prevention, alleviation, or treatment of a brain disease associated with increased activity of eIF4E, for example, FMCD (Focal Malformation of Cortical Development), a symptom of FMCD, or an associated disease thereof.

Below, a detailed description will be given of the present disclosure.

In the present disclosure, the brain disease caused by increased activity of eIF4E, a symptom thereof, or an associated disease thereof may be caused by increased activity of eIF4E in a brain neuronal cell or nervous tissue. The brain disease associated with increased activity of eIF4E may be caused by increased expression, intracellular level, or activity of eIF4E. For example, the brain disease caused by increased activity of eIF4E may be FMCD, for example, may include focal cortical dysplasia (FCD), hemimegalencephaly (HME), hemihypertrophy, multiple sclerosis (TSC), or Sturge-Weber syndrome (SWS).

The increased expression, intracellular level, or activity of eIF4E may be achieved through an upstream gene responsible for regulating eIF4E activity or expression, for example, a gene promotive of the activity and/or a gene inhibitory of the activity, or through the phosphorylation of eIF4E.

The activation of eIF4E by phosphorylation is largely conducted in two patterns including phosphorylation of eIF4E-binding proteins (4E-BPs) and phosphorylation of eIF4E. For example, mTOR is responsible for regulating eIF4E activity or expression and the disease may be caused by increased activity or expression of eIF4E which is driven by the upregulated activity or expression of mTOR gene. The activation of eIF4E by mTOR activating mutation may be accounted for by brain somatic mutation in an upstream gene which is involved in the PI3K-AKT-mTOR signaling pathway in a brain nervous tissue and neuronal cell. In detail, the brain somatic mutation in an upstream gene, for example, mTOR, PI3K, AKT, TSC, etc., in the PI3K-AKT-mTOR signaling pathway may be amino acid deletion, substitution, or insertion, and preferably amino acid substitution. Examples of the disease caused by the brain somatic mutation include focal cortical dysplasia (FCD) (e.g., FCD type II), hemimegalencephaly (HME), or Surge-Weber syndrome (SWS).

The brain disease associated with increased activity of eIF4E according to the present disclosure refers to a brain disease associated with increased activity of eIF4E in a brain neuronal cell or nervous tissue, but does not cover a hyper-proliferative disease associated with increased activity of eIF4E in body portions other than the brain or in cells or tissue other than neuronal cells or nervous tissues, for example, malignant tumors.

A symptom or an associated disease of the disease associated with increased activity of eIF4E according to the present disclosure may include at least one selected from the group consisting of epilepsy (especially intractable epilepsy), generation of abnormal neural cells in the cerebrum, and neuropsychiatric disorder. Specific symptoms of epilepsy include spontaneous seizure, behavioral seizure and/or electroencephalogram seizure. The neuropsychiatric disorder includes anxiety, cognitive impairment, short-term memory impairment, motor impairment, social behavior disorder, repetitive behavior disorder, and depression.

The term "epilepsy", as used herein, refers to a chronic disorder characterized by recurrent seizures as a result of an excessive electrical change in some neurons for a short period of time. The term "intractable epilepsy" refers to epilepsy that does not respond to any of the anti-epileptic drugs developed thus far. A disease causative of the intractable epilepsy includes malformations of cortical development, such as FCD, especially FCD Type II, HME, and TSC.

The epilepsy may be caused by a brain somatic mutation in a gene involved in the mTOR signaling pathway and more particularly, a brain somatic mutation in the gene mTOR, PI3K, AKT, or eIF4E involved in the mTOR signaling pathway, for example, amino acid deletion, substitution, or insertion, and preferably amino acid substitution.

Focal cortical dysplasia is one of sporadic cerebral cortical developmental abnormalities, which is accompanied by structural abnormalities of cerebral cortex and cytologic abnormalities of neuronal cells. Focal cortical dysplasia is divided into several types according to pathological criteria. Among them, FCD type II exhibits uniform pathological findings characterized by cortical dysplasia, dysmorphic neurons, or balloon cells (Epilepsia 52, 158-174 (2011)).

In brain tissues surgically obtained from focal cortical dysplasia patients, brain lesion-specific somatic mutations for focal cortical dysplasia can be detected using various deep sequencing techniques, such as whole exome sequencing, hybrid capture sequencing, amplicon sequencing, etc.

As demonstrated from the FMCD model animal according to an embodiment of the present disclosure, mTOR activating mutation increases eIF4E activity through the aforementioned mechanism, which in turn increases the activity and/or expression of an eIF4E activation-sensitive gene having A-rich, guanine quartet (GGC)$_4$, CERT, and/or U-rich motifs in the 5'-UTR thereof, leading to the onset of intractable epilepsy.

In the present disclosure, expression or activity of the eIF4E activation-sensitive genes is commonly regulated by eIF4E and the eIF4E activation-sensitive genes have a specific common motif, which is regulated by eIF4E, in the 5'-UTRs thereof. When the common motif is removed from the 5'-UTR, the expression of the gene was not upregulated any more by the increased activity of eIF4E. Therefore, it was found that the specific motif in the 5'-UTR of the eIF4E activation-sensitive gene according to the present disclosure is specifically regulated by eIF4E.

Specifically, the eIF4E activation-sensitive gene according to the present disclosure may include at least one motif selected from the group consisting of a U-rich motif, a guanine quartet motif, an A-rich motif, and a CERT motif. By way of example, the 5'-UTR may contain two or more different motifs, repeats of one motif, or a combination thereof. The U-rich motif is accounted for by TTDWTTTTNT (SEQ ID NO: 97), the guanine quartet motif by GGCGGCGGCGGC (SEQ ID NO: 98), the A-rich motif by AAAANATAAAA (SEQ ID NO: 99), and the CERT motif by GCCGCCGCCGCC (SEQ ID NO: 100). One guanine quartet is detected in the 5'-UTR of ADK gene, guanine quartet, A-rich, and CERT motifs in the 5'-UTR of CREB1 gene, and a U-rich motif in the 5'-UTR of IRSp53 gene.

The eIF4E hyperactivation-sensitive gene is listed in Table 1, below and preferably may be at least one selected from the group consisting of adenosine kinase (ADK), cAMP responsive element binding protein 1 (CREB1), and IRSp53. The eIF4E activation-sensitive gene or protein may be used as a biomarker for probing, detecting, or diagnosing a condition caused by increased eIF4E activity, for example, a disease, a disorder, a symptom thereof, or an associated disease thereof.

Specifically, from the distribution of fold changes in translational efficiency (TE) of individual genes at each time point relative to the control, 256 genes with z-score of 1.2 or more in MTOR-C1483Y or MTOR-L2427P models relative to MTOR-WT models were selected for eIF4E activation-sensitive proteins or genes. The selected genes are given in Table 1, below. The z-score of 1.2 or more in the distribution of TE fold changes meets the condition of log 2(TE [p.C1483Y]/[WT])≥2.142605598 and log 2(TE[p.L2427P]/[WT])≥2.232171262.

TABLE 1

| Gene Symbol | log2(TE [p.C1483Y]/ [WT]) | log2(TE [p.L2427P]/ [WT]) | Z-score(TE [p.C1483Y]/ [WT]) | Z-score(TE [p.L2427P]/ [WT]) |
|---|---|---|---|---|
| 5830418K08Rik | 3.2856631 | 4.5591033 | 1.7868901 | 2.5603092 |
| 9130011E15Rik | 3.51417249 | 2.6823654 | 1.9028764 | 1.4671319 |
| Abcd3 | 2.50073286 | 2.8555022 | 1.3884768 | 1.567982 |
| Abhd11 | 3.90207066 | 3.6263167 | 2.0997649 | 2.0169722 |
| Acp2 | 2.64286893 | 4.9551647 | 1.460622 | 2.7910102 |
| Acss2 | 4.40712622 | 4.6151318 | 2.3561199 | 2.5929451 |
| Adk | 4.75289218 | 3.1865551 | 2.5316231 | 1.7608164 |
| Akap12 | 2.79269016 | 2.8719541 | 1.5366679 | 1.5775651 |
| Akap6 | 3.64116218 | 4.1969928 | 1.9673335 | 2.3493842 |
| Aldh6a1 | 3.84339227 | 2.3184609 | 2.0699811 | 1.2551619 |
| Aldh7a1 | 3.71542216 | 4.0948263 | 2.0050263 | 2.2898734 |
| Alg10b | 3.80165894 | 3.7793599 | 2.0487981 | 2.106118 |
| Alkbh8 | 2.45996221 | 3.2205098 | 1.3677826 | 1.7805946 |
| Anapc11 | 3.24367565 | 4.3904542 | 1.7655782 | 2.4620731 |
| Ankrd13a | 3.19254087 | 3.128509 | 1.7396233 | 1.7270052 |
| Arfgap2 | 3.06321482 | 2.3417788 | 1.6739802 | 1.2687444 |
| Arfip2 | 2.17275667 | 2.7423389 | 1.2220034 | 1.5020658 |
| Atg2a | 2.25567335 | 3.0777147 | 1.26409 | 1.6974181 |
| Atp9b | 3.86588752 | 3.085986 | 2.0813991 | 1.7022361 |
| B4galt3 | 3.66297481 | 2.363857 | 1.9784051 | 1.2816046 |
| Bag1 | 3.11791212 | 2.6654072 | 1.7017434 | 1.457254 |
| Bai3 | 3.6397109 | 3.5282795 | 1.9665969 | 1.9598667 |
| BC037034 | 4.42211929 | 4.0664985 | 2.3637301 | 2.2733728 |
| Bcap31 | 5.89061681 | 3.0055392 | 3.1091069 | 1.6553768 |
| Bicd2 | 4.31449403 | 3.9481991 | 2.3091019 | 2.2044648 |
| C2cd21 | 2.74187106 | 2.2321713 | 1.5108732 | 1.2048993 |
| Cacng7 | 4.54392732 | 4.1402893 | 2.4255571 | 2.3163551 |
| Casp8ap2 | 2.15343867 | 3.3493978 | 1.212198 | 1.8556703 |
| Cbfb | 2.93248177 | 4.305199 | 1.607623 | 2.412413 |
| Ccdc85c | 2.80008216 | 2.9677035 | 1.5404199 | 1.6333379 |
| Ccna2 | 6.55094526 | 2.5901207 | 3.4442751 | 1.4134005 |
| Ccng2 | 2.93037152 | 2.3633945 | 1.6065519 | 1.2813352 |
| Cd9912 | 2.23567856 | 2.3494794 | 1.2539411 | 1.2732298 |
| Cdc26 | 2.27667706 | 4.1367687 | 1.2747511 | 2.3143043 |
| Cdc37 | 2.33722519 | 2.7254588 | 1.305484 | 1.4922333 |
| Cdc37l1 | 2.18987873 | 2.796954 | 1.2306942 | 1.5338784 |
| Cdk1 | 4.11012324 | 3.7569592 | 2.2053678 | 2.0930699 |
| Cep170b | 2.97138905 | 2.9107013 | 1.6273715 | 1.6001348 |
| Cep70 | 2.73848736 | 2.6855048 | 1.5091558 | 1.4689606 |
| Chchd1 | 2.94115082 | 3.5703768 | 1.6120232 | 1.9843879 |

TABLE 1-continued

| Gene Symbol | log2(TE [p.C1483Y]/ [WT]) | log2(TE [p.L2427P]/ [WT]) | Z-score(TE [p.C1483Y]/ [WT]) | Z-score(TE [p.L2427P]/ [WT]) |
|---|---|---|---|---|
| Chka | 3.77709567 | 3.3294571 | 2.0363304 | 1.8440551 |
| Clcn7 | 2.63037157 | 3.0387087 | 1.4542786 | 1.6746976 |
| Cluap1 | 2.38917506 | 3.0370247 | 1.3318526 | 1.6737167 |
| Cops3 | 3.02119963 | 3.8907357 | 1.6526543 | 2.1709031 |
| Cplx1 | 2.56291271 | 2.6107044 | 1.4200379 | 1.4253902 |
| Crl1 | 4.10628594 | 2.6910166 | 2.2034201 | 1.4721712 |
| Creb1 | 3.78627579 | 4.6574872 | 2.04099 | 2.6176166 |
| Ctsa | 4.70786584 | 4.0924853 | 2.5087687 | 2.2885098 |
| Ctsz | 4.28655898 | 3.7028614 | 2.2949227 | 2.0615585 |
| CUnbp2n1 | 3.22636487 | 3.4067755 | 1.7567916 | 1.8890921 |
| Dcun1d1 | 4.35230961 | 2.3695016 | 2.3282962 | 1.2848926 |
| Ddx28 | 2.79381592 | 2.312294 | 1.5372393 | 1.2515698 |
| Ddx54 | 2.5603724 | 3.0298635 | 1.4187485 | 1.6695454 |
| Dicer1 | 2.36124952 | 3.3004263 | 1.3176782 | 1.827145 |
| Dimt1 | 2.36710718 | 2.9739816 | 1.3206514 | 1.6369949 |
| Dlg3 | 2.46615436 | 2.4639877 | 1.3709255 | 1.3399296 |
| Dmxl1 | 5.30365144 | 2.8198142 | 2.8111763 | 1.5471942 |
| Dusp11 | 3.25281329 | 3.4605326 | 1.7702162 | 1.920405 |
| Dync2h1 | 3.08234773 | 3.4810935 | 1.6836917 | 1.9323814 |
| Dyrk2 | 2.90241867 | 5.1938115 | 1.5923637 | 2.9300191 |
| E430025E21Rik | 3.14365957 | 2.8084614 | 1.7148212 | 1.5405844 |
| Eef1d | 2.32632222 | 2.7207772 | 1.2999498 | 1.4895064 |
| Efhd2 | 2.70490435 | 3.8944797 | 1.4921098 | 2.1731739 |
| Efna4 | 4.53388702 | 3.2598453 | 2.4204609 | 1.803507 |
| Eif4ebp2 | 2.19032536 | 3.222706 | 1.2309208 | 1.7818738 |
| Epn2 | 2.3432873 | 3.418907 | 1.3085609 | 1.8961586 |
| Ept1 | 2.58907202 | 2.5398365 | 1.4333158 | 1.3841106 |
| Exd2 | 3.03585336 | 5.5851586 | 1.6600922 | 3.157974 |
| Fam214a | 3.33349073 | 3.1353713 | 1.8111663 | 1.7310024 |
| Fbxl15 | 3.15650571 | 2.7981507 | 1.7213326 | 1.5345755 |
| Fbx15 | 2.94836835 | 3.07889 | 1.6156867 | 1.6981027 |
| Fbxo44 | 3.64710956 | 3.5892837 | 1.9703523 | 1.995401 |
| Fkbp1a | 3.00733504 | 3.9047968 | 1.6456169 | 2.1791835 |
| Fkbp5 | 5.68378185 | 3.3894767 | 3.0041221 | 1.8790157 |
| Fundc1 | 2.93613865 | 3.0659569 | 1.6094792 | 1.6905694 |
| Galnt2 | 2.20931657 | 3.0053342 | 1.2405604 | 1.6552574 |
| Gas8 | 3.39376258 | 4.4158914 | 1.841759 | 2.4768899 |
| Gbas | 3.32439775 | 2.4686182 | 1.8065509 | 1.3426268 |
| Gfm2 | 4.47640785 | 2.3433825 | 2.3912858 | 1.2696785 |
| Gmppa | 7.44392554 | 3.1146183 | 3.8975321 | 1.7189141 |
| GPhn | 3.37808116 | 2.6308913 | 1.8337994 | 1.4371489 |
| Grsf1 | 2.85377027 | 2.601336 | 1.5676708 | 1.4199333 |
| Gtf2ird1 | 2.91476453 | 2.7898979 | 1.5986301 | 1.5297683 |
| Hap1 | 2.23006946 | 2.8261261 | 1.2510941 | 1.5508708 |
| Hdac4 | 2.66190057 | 3.0625822 | 1.470282 | 1.6886037 |
| Hint1 | 3.08842934 | 2.3646244 | 1.6867786 | 1.2820516 |
| Hist1h2bm | 3.2919312 | 2.2535338 | 1.7900716 | 1.2173427 |
| Hist2h4 | 2.94503466 | 3.0574136 | 1.6139946 | 1.685593 |
| Hnl1 | 3.52766105 | 2.5378846 | 1.9097229 | 1.3829736 |
| Hsd11 | 3.57453224 | 2.3092549 | 1.9335136 | 1.2497996 |
| Hspbp1 | 4.68052072 | 3.0532918 | 2.4948889 | 1.6831921 |
| Ifnar1 | 2.4036695 | 3.1484884 | 1.3392096 | 1.738643 |
| Ints9 | 2.48240568 | 2.7552702 | 1.3791744 | 1.5095981 |
| Ipo7 | 3.39895604 | 4.0937511 | 1.844395 | 2.2892471 |
| Kctd13 | 2.64340416 | 2.4354735 | 1.4608936 | 1.3233204 |
| Kctd17 | 8.09699097 | 4.7229141 | 4.2290137 | 2.655727 |
| Kdm1b | 6.04558712 | 2.8712246 | 3.1877665 | 1.5771402 |
| Klhl2 | 3.28764197 | 2.338704 | 1.7878945 | 1.2669533 |
| Klhl42 | 2.89493913 | 2.5216341 | 1.5885672 | 1.3735079 |
| Lcmt1 | 3.56908844 | 3.5116271 | 1.9307505 | 1.9501669 |
| Leprotl1 | 4.17016905 | 4.5564652 | 2.2358457 | 2.5587725 |
| Lhfpl4 | 2.66962768 | 2.8123077 | 1.4742041 | 1.5428218 |
| Lman2 | 3.69744247 | 4.1797903 | 1.9959002 | 2.3393639 |
| Lac16b | 3.65134149 | 5.5159584 | 1.9725003 | 3.1176658 |
| Lsm4 | 5.92260312 | 4.6432292 | 3.1253425 | 2.6093115 |
| Lta4h | 2.29319667 | 2.8477669 | 1.2831361 | 1.5634763 |
| Lyz2 | 4.40107743 | 2.2536795 | 2.3530497 | 1.2174276 |
| Mak16 | 2.76339212 | 2.8096904 | 1.5217969 | 1.5412972 |
| Man1b1 | 4.41782659 | 3.1114358 | 2.3615512 | 1.7170603 |
| Mapk9 | 5.30550998 | 4.7466957 | 2.8121197 | 2.6695795 |
| Mesdc2 | 2.8210658 | 2.4839872 | 1.5510707 | 1.351579 |
| Mfsd8 | 2.77168992 | 2.9983641 | 1.5260086 | 1.6511974 |
| Mgst3 | 2.8464849 | 2.8503997 | 1.5639729 | 1.5650099 |
| Mon2 | 2.22500165 | 2.3417553 | 1.2485218 | 1.2687306 |
| Mrpl23 | 2.44827635 | 3.5112 | 1.3618511 | 1.9499181 |
| Mrpl30 | 2.44828353 | 2.4608321 | 1.3618547 | 1.3380915 |

TABLE 1-continued

| Gene Symbol | log2(TE [p.C1483Y]/ [WT]) | log2(TE [p.L2427P]/ [WT]) | Z-score(TE [p.C1483Y]/ [WT]) | Z-score(TE [p.L2427P]/ [WT]) |
|---|---|---|---|---|
| Mrpl43 | 3.72077909 | 2.765537 | 2.0077453 | 1.5155784 |
| Mrpl45 | 2.20302539 | 2.2891612 | 1.2373671 | 1.2380952 |
| Mrto4 | 2.20687131 | 3.5162877 | 1.2393192 | 1.9528817 |
| Msantd3 | 2.29587326 | 2.4701118 | 1.2844946 | 1.3434967 |
| Nampt | 4.13781088 | 3.3783726 | 2.2194214 | 1.8725478 |
| Narf1 | 2.44807601 | 4.0853359 | 1.3617494 | 2.2843454 |
| Ndufa3 | 2.24135388 | 2.2427935 | 1.2568218 | 1.2110866 |
| Nelfa | 5.73959286 | 2.619677 | 3.0324505 | 1.4306167 |
| Nme7 | 2.75229653 | 2.767858 | 1.516165 | 1.5169303 |
| Nploc4 | 3.89962171 | 2.4852057 | 2.0985219 | 1.3522888 |
| Nrp2 | 3.67752176 | 3.2936718 | 1.9857888 | 1.8232106 |
| Osbpl2 | 4.78535716 | 3.3304507 | 2.5481016 | 1.8446338 |
| Pagr1a | 3.57789227 | 3.1983288 | 1.9352191 | 1.7676744 |
| Pan2 | 5.46529766 | 5.5151547 | 2.8932244 | 3.1171976 |
| Papd5 | 2.4110601 | 3.1823173 | 1.3429609 | 1.7583479 |
| Pard6a | 3.3105048 | 4.1092909 | 1.7994992 | 2.2982989 |
| Pcyt1a | 5.64522189 | 2.7058002 | 2.9845499 | 1.4807824 |
| Pdcd2 | 2.67770779 | 3.9559438 | 1.4783054 | 2.2089761 |
| Pdxp | 5.31809271 | 2.6260715 | 2.8185064 | 1.4343414 |
| Pex13 | 3.49963446 | 3.167124 | 1.8954972 | 1.749498 |
| Pfktb2 | 2.96806352 | 3.6649636 | 1.6256835 | 2.0394835 |
| Polr2c | 4.05837061 | 3.173369 | 2.1790993 | 1.7531356 |
| Pop4 | 3.33928325 | 2.6235951 | 1.8141065 | 1.4328989 |
| Ppplr10 | 2.32116548 | 3.0526632 | 1.2973324 | 1.6828259 |
| Prkar2a | 2.16590205 | 3.7084944 | 1.2185241 | 2.0648397 |
| Prpf38a | 3.25065058 | 3.1483157 | 1.7691185 | 1.7385424 |
| Psd3 | 3.98929206 | 2.7247325 | 2.1440366 | 1.4918103 |
| Ptcd3 | 3.82278389 | 3.7194961 | 2.0595207 | 2.0712481 |
| Ptpm2 | 2.86899971 | 2.6882481 | 1.5754009 | 1.4705585 |
| Ptpru | 2.50900243 | 4.0679509 | 1.3926743 | 2.2742188 |
| R3hcc1 | 2.24104709 | 2.2730127 | 1.2566661 | 1.2286889 |
| Rab2a | 6.5186579 | 4.844434 | 3.4278867 | 2.7265109 |
| Rap1gap | 5.19527675 | 4.4354615 | 2.7561677 | 2.4882893 |
| Rap2b | 2.34847275 | 2.4767369 | 1.311193 | 1.3473558 |
| Rbm45 | 3.55196324 | 3.050396 | 1.9220581 | 1.6815054 |
| Rcbtb2 | 3.51733022 | 2.3475437 | 1.9044792 | 1.2721023 |
| Rgs3 | 2.9111232 | 2.772411 | 1.5967819 | 1.5195824 |
| Rian | 2.87076983 | 3.1755758 | 1.5762994 | 1.754421 |
| Ric8 | 8.72513303 | 2.3826736 | 4.5478447 | 1.2925651 |
| Rlf | 4.3374585 | 3.9990296 | 2.3207581 | 2.234073 |
| Rnaseh2c | 2.48371622 | 3.1367336 | 1.3798396 | 1.731796 |
| Rnd3 | 2.46299386 | 4.1229297 | 1.3693214 | 2.3062433 |
| Rnf24 | 6.70574007 | 4.6457462 | 3.5228455 | 2.6107776 |
| Rpa2 | 2.51965707 | 2.8051124 | 1.3980823 | 1.5386306 |
| Rpgr | 5.74588167 | 2.5880439 | 3.0356426 | 1.4121908 |
| Samd4b | 5.29992671 | 3.0706801 | 2.8092857 | 1.6933206 |
| Sap130 | 2.99737365 | 2.6659827 | 1.6405607 | 1.4575892 |
| Sart1 | 2.61309671 | 2.9733795 | 1.4455102 | 1.6366441 |
| Sbds | 4.76991977 | 2.6350228 | 2.5402659 | 1.4395554 |
| Scaf8 | 3.78782237 | 3.685814 | 2.041775 | 2.0516287 |
| Sec23a | 2.69727519 | 3.149027 | 1.4882374 | 1.7389567 |
| Sept9 | 2.16801345 | 4.1109862 | 1.2195958 | 2.2992863 |
| Sh3glb1 | 2.1426056 | 2.6075124 | 1.2066994 | 1.423531 |
| Shkbp1 | 2.27249537 | 2.7246948 | 1.2726285 | 1.4917883 |
| Sike1 | 2.78217733 | 2.4686615 | 1.5313318 | 1.342652 |
| Sipa1l1 | 3.14755761 | 2.2693811 | 1.7167908 | 1.2265736 |
| Slc25a17 | 2.40962792 | 2.798179 | 1.342234 | 1.534592 |
| Slc29a4 | 3.50483688 | 2.3975639 | 1.8981378 | 1.3012385 |
| Slc30a5 | 3.3525133 | 3.1579409 | 1.8208217 | 1.7441489 |
| Slc35b4 | 3.14790045 | 2.2767761 | 1.7169648 | 1.2308811 |
| Smc6 | 3.57120524 | 3.0694862 | 1.9318249 | 1.6926252 |
| Snapc3 | 3.04143459 | 2.4534287 | 1.6629251 | 1.3337791 |
| Snx13 | 4.78391441 | 2.6276813 | 2.5473693 | 1.4352791 |
| Socs6 | 3.67887016 | 4.3720688 | 1.9864733 | 2.4513639 |
| Spns1 | 2.90741242 | 2.4968309 | 1.5948984 | 1.3590603 |
| Spryd3 | 4.69336996 | 2.4758247 | 2.5014109 | 1.3468244 |
| Srsf4 | 5.0080472 | 2.5154349 | 2.9149231 | 1.3698969 |
| Stk35 | 2.95341596 | 2.5856721 | 1.6182488 | 1.4108092 |
| Stk36 | 2.54379578 | 5.682034 | 1.4103346 | 3.2144028 |
| Sult4a1 | 2.194657 | 2.4852584 | 1.2331195 | 1.3523195 |
| Tars2 | 2.46042694 | 3.0555761 | 1.3680184 | 1.6845227 |
| Tbc1d14 | 3.51508436 | 3.464142 | 1.9033392 | 1.9225074 |
| Tbp | 5.41048128 | 3.9875535 | 2.8654008 | 2.2273883 |
| Tbrg1 | 2.29159917 | 2.2850008 | 1.2823252 | 1.2356719 |
| Tmem11 | 3.51118312 | 3.1221879 | 1.901359 | 1.7233232 |
| Tmem132b | 3.28355027 | 4.3736388 | 1.7858176 | 2.4522784 |

TABLE 1-continued

| Gene Symbol | log2(TE [p.C1483Y]/ [WT]) | log2(TE [p.L2427P]/ [WT]) | Z-score(TE [p.C1483Y]/ [WT]) | Z-score(TE [p.L2427P]/ [WT]) |
|---|---|---|---|---|
| Tmem44 | 3.104972 | 3.7682099 | 1.6951753 | 2.0996233 |
| Tmub2 | 2.34540761 | 2.567316 | 1.3096372 | 1.400117 |
| Traf4 | 2.2585901 | 3.8347851 | 1.2655705 | 2.1384025 |
| Trim8 | 2.88701245 | 4.1994575 | 1.5845438 | 2.3508198 |
| Ttc13 | 4.07886504 | 3.2371211 | 2.1895018 | 1.7902704 |
| Ttc33 | 5.95232536 | 2.2989447 | 3.1404288 | 1.243794 |
| Ttyh1 | 4.54541338 | 3.9692053 | 2.4263114 | 2.2167007 |
| Tub | 3.12756533 | 2.9711791 | 1.7066431 | 1.6353625 |
| Txn2 | 6.00419076 | 4.2368528 | 3.1667546 | 2.3726021 |
| Txndc16 | 2.43947484 | 2.9849377 | 1.3573836 | 1.6433766 |
| Ube2m | 3.90088402 | 2.4202251 | 2.0991626 | 1.3144384 |
| Unc79 | 3.74317238 | 2.6195756 | 2.0191117 | 1.4305576 |
| Upf3a | 7.68946208 | 3.6402834 | 4.022161 | 2.0251077 |
| Uso1 | 4.92411717 | 4.3719504 | 2.6185331 | 2.4512949 |
| Usp11 | 4.89078293 | 4.7420138 | 2.6016134 | 2.6668524 |
| Vti1b | 4.02417391 | 4.0869526 | 2.1617418 | 2.2852871 |
| Wdr5 | 3.06576486 | 2.5963471 | 1.6752746 | 1.4170273 |
| Ypel1 | 5.82431342 | 3.7186054 | 3.0754528 | 2.0707292 |
| Zcchc17 | 4.23987298 | 4.1958037 | 2.2712259 | 2.3486915 |
| Zfp128 | 3.27218513 | 2.7063625 | 1.7800489 | 1.4811099 |
| Zfp553 | 2.37628249 | 3.5674136 | 1.3253086 | 1.9826619 |
| Zfp623 | 4.16147602 | 3.125352 | 2.2314333 | 1.7251663 |
| 2310045N01Rik | n.a. | n.a. | n.a. | n.a. |
| Abat | n.a. | n.a. | n.a. | n.a. |
| Abhd13 | n.a. | n.a. | n.a. | n.a. |
| Acy1 | n.a. | n.a. | n.a. | n.a. |
| Adamts18 | n.a. | n.a. | n.a. | n.a. |
| Adarb1 | n.a. | n.a. | n.a. | n.a. |
| Adpgk | n.a. | n.a. | n.a. | n.a. |
| Atg13 | n.a. | n.a. | n.a. | n.a. |
| B230118H07Rik | n.a. | n.a. | n.a. | n.a. |
| Baiap2 (IRSp53) | n.a. | n.a. | n.a. | n.a. |
| Ccrs4 | n.a. | n.a. | n.a. | n.a. |
| Cln8 | n.a. | n.a. | n.a. | n.a. |
| Cmtr2 | n.a. | n.a. | n.a. | n.a. |
| Commd8 | n.a. | n.a. | n.a. | n.a. |
| Dhodh | n.a. | n.a. | n.a. | n.a. |
| Esyt2 | n.a. | n.a. | n.a. | n.a. |
| Fcf1 | n.a. | n.a. | n.a. | n.a. |
| Galk1 | n.a. | n.a. | n.a. | n.a. |
| Gmppb | n.a. | n.a. | n.a. | n.a. |
| Hmces | n.a. | n.a. | n.a. | n.a. |
| Kctd18 | n.a. | n.a. | n.a. | n.a. |
| Leng1 | n.a. | n.a. | n.a. | n.a. |
| Mettl22 | n.a. | n.a. | n.a. | n.a. |
| Mrpl1 | n.a. | n.a. | n.a. | n.a. |
| Mrpl57 | n.a. | n.a. | n.a. | n.a. |
| Nfxl1 | n.a. | n.a. | n.a. | n.a. |
| Nsmaf | n.a. | n.a. | n.a. | n.a. |
| Pofut2 | n.a. | n.a. | n.a. | n.a. |
| Psrc1 | n.a. | n.a. | n.a. | n.a. |
| Rev1 | n.a. | n.a. | n.a. | n.a. |
| Rpap1 | n.a. | n.a. | n.a. | n.a. |
| Slc15a4 | n.a. | n.a. | n.a. | n.a. |
| Smg5 | n.a. | n.a. | n.a. | n.a. |
| Suv420h2 | n.a. | n.a. | n.a. | n.a. |
| Tmem178b | n.a. | n.a. | n.a. | n.a. |
| Tor1aip1 | n.a. | n.a. | n.a. | n.a. |
| Trub1 | n.a. | n.a. | n.a. | n.a. |
| Vamp3 | n.a. | n.a. | n.a. | n.a. |
| Zfp426 | n.a. | n.a. | n.a. | n.a. |
| Zfp566 | n.a. | n.a. | n.a. | n.a. |
| Zfyve9 | n.a. | n.a. | n.a. | n.a. |
| Zscan12 | n.a. | n.a. | n.a. | n.a. |

As a concrete example of the eIF4E hyperactivation-sensitive gene, adenosine kinase (ADK, EC 2.7.1.20) is an evolutionarily conserved phosphotransferase that converts adenosine to 5'-adenosine monophosphate. ADK plays a role as an upstream regulator in the complicated homeostasis and metabolism network. ADK dysfunction is associated with various pathologies including diabetes, cancer, etc. Amino acid and nucleic acid sequences of human adenosine kinase are known, as exemplified by NCBI accession number NP_001114.2, NP_001189378.1, NP_001189379.1, NP_001356052.1, or NP_006712.2 for the amino acid sequence and by NCBI accession number NC_000010.11 for the nucleic acid sequence. A model that suffers from epilepsy upon the overexpression of ADK in astrocytes is known, but is irrelevant to the present disclosure, which is drown to the epilepsy that occurs as ADK is overexpressed in neurons.

cAMP responsive element binding protein 1 (CREB1), which is a cellular transcription factor, binds to certain DNA sequences called cAMP response elements (CRE), thereby regulating the transcription of the downstream genes. Amino acid and nucleic acid sequences of human CREB1 are known, as exemplified by NCBI accession number NP_001307722.1, NP_004370.1, and NP_604391.1 for the amino acid sequences and by NCBI accession number NG_023299.1 for the nucleic acid sequence.

Insulin receptor substrate p53 (IRSp53), also known as brain-specific angiogenesis inhibitor 1-associated protein 2 (BAIAP2), interacts with brain-specific angiogenesis inhibitor 1 and functions as an insulin receptor tyrosine kinase substrate. Amino acid and nucleic acid sequences of human IRSp53 are known as exemplified by NCBI accession numbers NP_001138360.1, NP_006331.1, NP_059344.1, and NP_059345.1 for the amino acid sequences and by NCBI accession number NG_029486.2 for the nucleic acid sequence.

The eIF4E inhibitor according to the present disclosure is a substance capable of inhibiting the expression, activity, or level of eIF4E in the brain and may encompass compounds (e.g., metformin), polynucleotides (e.g., siRNA, shRNA, miRNA, antisense oligonucleotide, etc.), polypeptides and antibodies (e.g., whole antibodies, antibody fragments, etc.), but is not limited thereto. Preferably, the polynucleotide may be an antisense polynucleotide. In detail, the polynucleotide may be any polynucleotide or nucleic acid molecule capable of complementarily binding to a target gene and include DNA and RNA which may be single-stranded or double-stranded. The term "inhibitory activity against the expression, activity, or level of eIF4E" refers to reducing the expression, activity, or level of eIF4E to 95% or less, 90% or less, 85% or less, 80% or less, 75% or less, 70% or less, 65% or less, 60% or less, 55% or less or 50% or less of that in a subject free of a brain disease associated with increased expression of eIF4E.

Therefore, so long as it is known in the art, any eIF4E inhibitor may be available in the present disclosure. For example, the eIF4E inhibitor includes (i) Ribavirin, synthetic nucleotide derivative 7-benzyl guanosine monophosphate (7-BnGMP), and 4Ei-1 (nontoxic small molecule), which are each a cap-binding antagonist that binds to eIF4E and competitively inhibits EIF4E binding to 7-MeG-Capped mRNA, (ii) 4EGI-1. 4E1RCat, Ouabain, (a kind of cardiac glycoside), and Perilly alcohol (a kind of secondary product of plant mevalonate metabolism), which are each an eIF4E-eIF4G interaction inhibitor, (iii) 4EBP mimetic peptide and GnRH agonist-4EBP fusion peptide, which each bind to eIF4E to decreases a level of free eIF4E, (iv) CGP052088 (a derivative of staurosporine, a broad spectrum kinase inhibitor), CGP57380 (a potent Mnk1 and Mnk2 inhibitor), and Retinamides (a novel Mnk inhibitor/one of retinoic acid metabolism blocking agents/blocked eIF4E phosphorylation), which are each an Mnk inhibitor blocking eIF4E phosphorylation, and (v) an antisense oligonucleotide.

The eIF4E inhibitor may be a cap-binding antagonist, an eIF4E-eIF4G interaction inhibitor, a substance binding to eIF4E to decrease a level of free eIF4E, an Mnk inhibitor blocking eIF4E phosphorylation, or a nucleic acid binding to eIF4E. More specifically, the eIF4E inhibitor may be metformin, Ribavirin, 7-BnGMP, 4Ei-1, 4EGI-1. 4E1RCat, Quabain, Perilly alcohol, 4EBP mimetic peptide, GnRH agonist-4EBP fusion peptide, CGP052088, CGP57380, or siRNA, shRNA or antisense oligonucleotide capable of binding to eIF4E.

So long as it has inhibitory activity against eIF4E expression, activity, or level, any antisense oligonucleotide (MO) can be employed as an eIF4E inhibitor in the present disclosure even though known as an anticancer agent in the art. Examples of the antisense oligonucleotide include those disclosed in U.S. Pat. Nos. 9,096,851, 8,410,074, 8,252,762, and 7,601,700, but without limitations thereto. Exemplary eIF4E-specific ASO includes LY2275796 and ISIS 183750, but are not limited thereto.

In an embodiment thereof, the present disclosure provides an eIF4E mRNA expression inhibitor, for example, eIF4E inhibitor including a polynucleotide capable of complementarily binding to eucaryotic translation initiation factor 4E (eIF4E). Herein, the "mRNA expression inhibitor" complementarily binds to mRNA to inhibit the expression of the protein encoded by the mRNA and may be preferably at least one selected from the group consisting of an antisense oligonucleotide, an siRNA, an shRNA, and a microRNA, and more preferably an shRNA, but without limitations thereto. The shRNA can achieve more effectively the goal because it has a high turnover rate, with a low degradation rate, when transfected.

In the present invention, the polynucleotide functioning as the eIF4E inhibitor may be an antisense oligonucleotide, an siRNA, or an shRNA, which each bind complementarily to an eIF4E mRNA. The polynucleotide complementarily binds to eIF4E mRNA which is in turn subjected to the degradation mediated by RNase H, thereby preventing, alleviation, or treating a disease associated with increased eIF4E expression, a symptom thereof, or an associated disease thereof.

In an embodiment according to the present disclosure, the eIF4E inhibitor may be an eIF4E inhibiting drug, for example, metformin. Alternatively, the eIF4E inhibitor may be an shRNA and may include, for example, SEQ ID NO: 203 or SEQ ID NO: 204. In another embodiment, the eIF4E inhibitor may be an antisense oligonucleotide (ASO) examples of which are listed in Table 2, below. Any oligonucleotide that inhibits the expression and/or activity of an eIF4E gene is available.

The oligonucleotide may be an antisense oligonucleotide that inhibits the activity or expression of eIF4E and 14 to 30 nucleotides, 15 to 30 nucleotides, 16 to 30 nucleotides, 17 to 30 nucleotides, 18 to 30 nucleotides, 19 to 30 nucleotides, 14 to 25 nucleotides, 15 to 25 nucleotides, 16 to 25 nucleotides, 17 to 25 nucleotides, 18 to 25 nucleotides, 19 to 25 nucleotides, 14 to 23 nucleotides, 15 to 23 nucleotides, 16 to 23 nucleotides, 17 to 23 nucleotides, 18 to 23 nucleotides, or 19 to 23 nucleotides long. More particularly, the antisense oligonucleotide may be an antisense nucleic acid molecule that hybridizes specifically with at least one selected from a 5'-untranslated region, an translation initiation region, an exon, an intron, and 3'-untranslated region in eIF4E.

Generally, an antisense oligonucleotide refers to a single-stranded oligonucleotide having a base sequence that allows hybridization with a corresponding segment of a target nucleic acid molecule.

The antisense oligonucleotide according to an embodiment of the present disclosure is an antisense nucleic acid molecule that hybridizes specifically with at least one selected from the group consisting of a 5'-untranslated region, an translation initiation region, an exon, an intron, and a 3'-untranslated region in eIF4E to reduce the production expression level, and/or activity of eIF4E, thereby preventing, alleviating, or treating a condition caused by the hyperactivation or increased activity of eIF4E in brain neuronal cells, specifically, a disease or disorder or a symptom of the disease or disorder. In addition, the antisense oligonucleotide according to the present disclosure can inhibit or reduce the activity of eIF4E and thus can regulate the expression or activity of an eIF4E activation-sensitive gene the expression of which is regulated by eIF4E. The eIF4E activation-sensitive gene is as described above.

In greater detail, the antisense oligonucleotide can reduce the expression level of eIF4E mRNA to 95% or less, 90% or less, 85% or less, 80% or less, 75% or less, 70% or less, 65% or less, 60% or less, 55% or less, or 50% or less of that of the control having the sequence of SEQ ID NO: 201.

Various chemical modifications for improving stability in vivo, conferring resistance to nucleases, and reducing non-specific immune responses may be imparted to the oligonucleotide.

The antisense oligomer compound may be modified to have at least one stabilizing group at at least one terminus of the oligomer strand in order to increase, for example, stability to nucleases. The term "cap structure" or "terminal cap moiety" means chemical modifications, which have been incorporated at either terminus of an antisense oligomer compound.

In addition, the antisense oligonucleotide may have a chemically modified inter-nucleoside linkage, sugar moiety, or base. The "modified oligonucleotide" refers to an oligonucleotide having at least one modified inter-nucleoside linkage, a modified sugar, and/or a modified nucleobase.

Used in the chemically modified nucleotide may be at least one selected from the group consisting of: a modification in which the OH group at 2' position of the sugar moiety of the nucleotide is substituted with —CH3 (methyl), —OCH3 (methoxy), —NH2, —F, —O-2-methoxyethyl, —O-propyl, —O-2-methylthioethyl, —O-3-aminopropyl, —O-3-dimethylaminopropyl, —O—N-methylacetamido, or —O-dimethylamidooxyethyl; a modification in which the oxygen on the sugar moiety of the nucleotide is substituted with sulfur; a modification in which a cytosine in the nucleotide is modified to have a methyl group at 5 position; and a modification in which the inter-nucleoside linkage is modified into a phosphorothioate, boranophosphate, or methyl phosphonate linkage. The oligonucleotide may include a modification into PNA (peptide nucleic acid), LNA (locked nucleic acid), or UNA (unlocked nucleic acid). LNA is a modified nucleotide in which the ribose moiety is modified with an extra methylene bridge connecting the 2' oxygen and 4' carbon "cEt" or "constrained ethyl" or "cEt modified sugar" means a bicyclic nucleoside having a sugar moiety comprising a bridge connecting the 4'-carbon and the 2'-carbon, wherein the bridge has the formula: 4'-CH(CH3)-O-2'.

In an embodiment of the present disclosure, the antisense oligonucleotide may include at least one chemical modification selected from the group consisting of a chemically modified inter-nucleoside linkage, a chemically modified sugar moiety, and a chemically modified nucleobase.

Individual nucleotides in the oligonucleotide may be chemically modified and may comprise a modified sugar moiety selected from constrained ethyl (cET), 2'-O-methoxyethyl (2'-MOE), and locked nucleic acid (LNA). In the oligonucleotide, the number of the modified nucleotide may be 1 to 6, for examples 1, 2, 3, 4, 5, or 6 at each terminus thereof.

Individual nucleotides in the oligonucleotide may include a chemically modified base. The term "modified base" means any nucleobase other than adenine, cytosine, guanine, thymidine or uracil. "Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U). For example, a modified base may be cytosine having a methyl group at 5-position.

In the antisense oligonucleotide, the inter-nucleoside linkage may be chemically modified, as exemplified by a phosphorothioate linkage, a boranophosphate linkage, or a methyl phosphonate linkage, with preference for a phosphorothioate linkage.

In the present disclosure, the administration of an antisense oligonucleotide, the adeno associated virus (AAV)-mediated delivery of siRNA, the administration of an eIF4E activity inhibitory (e.g., eFT-508), or the peptide-mediated delivery of RNA may be conducted.

The composition according to the present disclosure may be administered to a subject via various routes. All modes of administration may be contemplated. For example, administration may be made parenterally. Parenteral administration means administration through injection (e.g., bolus injection) or infusion. Parenteral administration includes subcutaneous injection, intravenous injection, intramuscular injection, intra-arterial injection, intraperitoneal injection, intracerebral injection, intrathecal injection, or intracerebroventricular injection.

Concrete examples of the antisense polynucleotide are listed in Table 2. In Table 2, the oligonucleotides of SEQ ID NOS: 1 to 89 and SEQ ID NOS: 101 to 200 comprise 2'-MOE modification on the nucleotides at positions 1-5 and 16-20 in the 5' to 3' direction. The oligonucleotides of SEQ ID NOS:81 to 95 comprise 2'-MOE on the nucleotides at positions 1-3 and 14-16. All of the oligonucleotides in Table 2 are modified to contain a phosphorothioate bond between every adjacent two nucleotides.

TABLE 2

| SEQ ID NO | Id | Nucleotide sequence (5'->3') | Target Position |
|---|---|---|---|
| 1 | EIF4E_98879841 | AAACAAAGATAGCCACATCA | 3' UTR |
| 2 | EIF4E_98879924 | TCAAACTAGTGCTCCAAACT | 3' UTR |
| 3 | EIF4E_98880043 | AGGACAAATCTAGTTGTCTA | 3' UTR |
| 4 | EIF4E_98880044 | GGACAAATCTAGTTGTCTAA | 3' UTR |
| 5 | EIF4E_98880054 | AGTTGTCTAAAAGACAATTC | 3' UTR |
| 6 | EIF4E_98881125 | CTTTCCTTGTATACCCTCCT | Exon7 |
| 7 | EIF4E_98881126 | TTTCCTTGTATACCCTCCTA | Exon7 |
| 8 | EIF4E_98882525 | AGGATAGGTTTTTTTATAC | Intron6 |
| 9 | EIF4E_98882527 | GATAGGTTTTTTTTATACCT | Intron6 |
| 10 | EIF4E_98883689 | CACTGCGCCTGGTGTCAAAT | Intron6 |
| 11 | EIF4E_98883695 | GCCTGGTGTCAAATATTACT | Intron6 |
| 12 | EIF4E_98885582 | GGCATACATACAGGGACATG | Intron5 |
| 13 | EIF4E_98885583 | GCATACATACAGGGACATGT | Intron5 |
| 14 | EIF4E_98886839 | GCTTACTGTGGTGAGAGTCA | Intron5 |
| 15 | EIF4E_98886840 | CTTACTGTGGTGAGAGTCAA | Intron5 |
| 16 | EIF4E_98887070 | AAACCTTACTGTCTCTAGCC | Exon5 |
| 17 | EIF4E_98887071 | AACCTTACTGTCTCTAGCCA | Exon5 |
| 18 | EIF4E_98887260 | AACAGTTAAGCAACAACACT | Intron4 |
| 19 | EIF4E_98887261 | ACAGTTAAGCAACAACACTG | Intron4 |
| 20 | EIF4E_98887650 | CTGGATAATCAAAGCTCTCA | Intron4 |
| 21 | EIF4E_98887651 | TGGATAATCAAAGCTCTCAT | Intron4 |
| 22 | EIF4E_98887880 | TAAGCATACCTTAAAAAGTG | Exon4 |
| 23 | EIF4E_98887881 | AAGCATACCTTAAAAAGTGA | Exon4 |
| 24 | EIF4E_98887882 | AGCATACCTTAAAAAGTGAG | Exon4 |
| 25 | EIF4E_98887883 | GCATACCTTAAAAAGTGAGT | Exon4 |

TABLE 2 -continued

| SEQ ID NO | Id | Nucleotide sequence (5'->3') | Target Position |
|---|---|---|---|
| 26 | EIF4E_98887884 | CATACCTTAAAAAGTGAGTA | Exon4 |
| 27 | EIF4E_98888747 | TCTCCAATATTAGATGGCAG | Intron3 |
| 28 | EIF4E_98888750 | CCAATATTAGATGGCAGAAA | Intron3 |
| 29 | EIF4E_98889967 | AAATTATTAGGCCTTAAATG | Intron3 |
| 30 | EIF4E_98889970 | TTATTAGGCCTTAAATGTAG | Intron3 |
| 31 | EIF4E_98891226 | TGGTTACTTACGCCCAAAAG | Exon3 |
| 32 | EIF4E_98891227 | GGTTACTTACGCCCAAAAGT | Exon3 |
| 33 | EIF4E_98891228 | GTTACTTACGCCCAAAAGTC | Exon3 |
| 34 | EIF4E_98891229 | TTACTTACGCCCAAAAGTCT | Exon3 |
| 35 | EIF4E_98891231 | ACTTACGCCCAAAAGTCTTC | Exon3 |
| 36 | EIF4E_98901055 | CCAAGTCAGCACGGACTTTT | Intron2 |
| 37 | EIF4E_98901056 | CAAGTCAGCACGGACTTTTT | Intron2 |
| 38 | EIF4E_98901057 | AAGTCAGCACGGACTTTTTT | Intron2 |
| 39 | EIF4E_98901649 | TCCATTATGACCAATACTTT | Intron2 |
| 40 | EIF4E_98901650 | CCATTATGACCAATACTTTT | Intron2 |
| 41 | EIF4E_98901651 | CATTATGACCAATACTTTTC | Intron2 |
| 42 | EIF4E_98901863 | TTAGAAAGCTTACCTGTTCT | Exon2 |
| 43 | EIF4E_98901864 | TAGAAAGCTTACCTGTTCTG | Exon2 |
| 44 | EIF4E_98901865 | AGAAAGCTTACCTGTTCTGT | Exon2 |
| 45 | EIF4E_98916244 | TATAACAATTACAGGAAGCT | Intron1 |
| 46 | EIF4E_98916247 | AACAATTACAGGAAGCTATA | Intron1 |
| 47 | EIF4E_98923992 | CATGCTCATTTCCACTTCTC | Intron1 |
| 48 | EIF4E_98928252 | TACAGCGATCTGTAGGCCTC | Intron1 |
| 49 | EIF4E_98928259 | ATCTGTAGGCCTCGCTCCTC | Intron1 |
| 50 | EIF4E_98928283 | TTCCCTCCTCCATGACAGCC | Intron1 |
| 51 | EIF4E_98929081 | AAGGCAATACTCACCGGTTC | Exon1 |
| 52 | EIF4E_98929101 | GACAGTCGCCATCTTAGATC | Exon1 |
| 53 | EIF4E_98929115 | TAGATCGATCTGATCGCACA | 5' UTR |
| 54 | EIF4E_98929123 | TCTGATCGCACAACCGCTCC | 5' UTR |
| 55 | EIF4E_98929166 | AATGAGATTCAAACCGGATT | 5' UTR |
| 56 | EIF4E_98929170 | AGATTCAAACCGGATTGGCC | 5' UTR |
| 57 | EIF4E_98929269 | GGCTTCTGGGAAGTGGAGTC | 5' UTR |
| 58 | EIF4E_98929547 | ATAAGGCTTCATTTGCTTAG | 5' UTR |
| 59 | EIF4E_98930006 | GGGTCAACTATGACTCTTGA | 5' UTR |
| 60 | EIF4E_98930012 | ACTATGACTCTTGACGTTGA | 5' UTR |
| 61 | EIF4E_98930017 | GACTCTTGACGTTGACTCAT | 5' UTR |
| 62 | EIF4E_98930038 | CTCCTTAGGCGAGTGACTTA | 5' UTR |
| 63 | EIF4E_98930102 | GATACACTTACCTCACAAGG | 5' UTR |
| 64 | EIF4E_98930109 | TTACCTCACAAGGGTGTGCT | 5' UTR |

TABLE 2 -continued

| SEQ ID NO | Id | Nucleotide sequence (5'->3') | Target Position |
|---|---|---|---|
| 65 | EIF4E_98880048 | AAATCTAGTTGTCTAAAAGA | 3' UTR |
| 66 | EIF4E_98880053 | TAGTTGTCTAAAAGACAATT | 3' UTR |
| 67 | EIF4E_98928260 | TCTGTAGGCCTCGCTCCTCC | Intron1 |
| 68 | EIF4E_98928261 | CTGTAGGCCTCGCTCCTCCC | Intron1 |
| 69 | EIF4E_98928284 | TCCCTCCTCCATGACAGCCC | Intron1 |
| 70 | EIF4E_98929933 | AGATGCCAGCCAGGGAAGCC | 5' UTR |
| 71 | EIF4E_98929937 | GCCAGCCAGGGAAGCCACTC | 5' UTR |
| 72 | EIF4E_98884969 | TGCTATCTTATCACCTTTAG | Exon6 |
| 73 | EIF4E_98880876 | GGCGAATGAGACTTCTCTTA | 3' UTR |
| 74 | EIF4E_98880414 | TCCTGGATCCTTCACCAATG | 3' UTR |
| 75 | EIF4E_98880406 (ASO-1) | TGTCATATTCCTGGATCCTT | 3' UTR |
| 76 | EIF4E_98880417 (ASO-2) | TGGATCCTTCACCAATGTTA | 3' UTR |
| 77 | EIF4E_98880419 (ASO-3) | GATCCTTCACCAATGTTACA | 3' UTR |
| 78 | EIF4E_98884977 (ASO-4) | TATCACCTTTAGCTCTAACA | Exon6 |
| 79 | EIF4E_98887921 (ASO-5) | AATTACTAGACAACTGGATA | Exon4 |
| 80 | EIF4E_98929104 | CATCTTAGATCGATCTGATC | Exon1 |
| 81 | EIF4E_98880414_shortform | CTGGATCCTTCACCAA | 3' UTR |
| 82 | EIF4E_98884969_shortform | CTATCTTATCACCTTT | Exon6 |
| 83 | EIF4E_98887921_shortform | TTACTAGACAACTGGA | Exon4 |
| 84 | EIF4E_98929104_shortfonn | ATCTTAGATCGATCTG | Exon1 |
| 85 | EIF4E_98891227_shortform | TTACTTACGCCCAAAA | Exon3 |
| 86 | EIF4E_98881125_shortform | TTCCTTGTATACCCTC | Exon7 |
| 87 | EIF4E_98887070_shortfonn | ACCTTACTGTCTCTAG | Exon5 |
| 88 | EIF4E_98901864_shortfonn | GAAAGCTTACCTGTTC | Exon2 |
| 89 | EIF4E_98930017_shortform | CTCTTGACGTTGACTC | 5' UTR |
| 90 | EIF4E_98928261_shortform | GTAGGCCTCGCTCCTC | Intron1 |
| 91 | EIF4E_98901649_shortform | CATTATGACCAATACT | Intron2 |
| 92 | EIF4E_98888750_shortform | AATATTAGATGGCAGA | Intron3 |
| 93 | EIF4E_98887650_shortform | GGATAATCAAAGCTCT | Intron4 |
| 94 | EIF4E_98886839_shortform | TTACTGTGGTGAGAGT | Intron5 |
| 95 | EIF4E_98883695_shortform | CTGGTGTCAAATATTA | Intron6 |
| 101 | EIF4E_98929109 | CCATCTTAGATCGATCTGAT | EXON1 |
| 102 | EIF4E_98929111 | ATCTTAGATCGATCTGATCG | EXON1 |
| 103 | EIF4E_98929201 | ACGTGACGGATATGTCCGTT | EXON1 |
| 104 | EIF4E_98929463 | TGCCAGGCAAGCCTACTGTG | EXON1 |
| 105 | EIF4E_98929873 | GAAGTTCTGTGCAACCGTTC | EXON1 |
| 106 | EIF4E_98929875 | AGTTCTGTGCAACCGTTCCA | EXON1 |
| 107 | EIF4E_98929917 | GAAATAGCCTAAGTCCAGAT | EXON1 |

TABLE 2 -continued

| SEQ ID NO | Id | Nucleotide sequence (5'->3') | Target Position |
|---|---|---|---|
| 108 | EIF4E_98929921 | TAGCCTAAGTCCAGATGCCA | EXON1 |
| 109 | EIF4E_98930010 | CAACTATGACTCTTGACGTT | EXON1 |
| 110 | EIF4E_98930095 | AGGTGATGATACACTTACCT | EXON1 |
| 111 | EIF4E_98930164 | GACTCTAGAAATGATTCATA | EXON1 |
| 112 | EIF4E_98902048 | ACTAAACCTGAACTGATATG | Intron1 |
| 113 | EIF4E_98902052 | AACCTGAACTGATATGCTGA | Intron1 |
| 114 | EIF4E_98902946 | CTATCGTAACCTAAAAGTTC | Intron1 |
| 115 | EIF4E_98902976 | TATTTTCAATGGAACCTAAC | Intron1 |
| 116 | EIF4E_98904158 | GTATTTGTGAAACGTAAGCA | Intron1 |
| 117 | EIF4E_98906453 | ATTCAGGCTTACATATTGTA | Intron1 |
| 118 | EIF4E_98908332 | ACGTGTTCGGTCAATGCTAC | Intron1 |
| 119 | EIF4E_98908338 | TCGGTCAATGCTACAGCACC | Intron1 |
| 120 | EIF4E_98910345 | TCATATATCAATCATGATTC | Intron1 |
| 121 | EIF4E_98910440 | ACTGGATTACTAAAGAGTTG | Intron1 |
| 122 | EIF4E_98910444 | GATTACTAAAGAGTTGTGAT | Intron1 |
| 123 | EIF4E_98911027 | CCAGGCCTAAAACTTGGATG | Intron1 |
| 124 | EIF4E_98911030 | GGCCTAAAACTTGGATGAAT | Intron1 |
| 125 | EIF4E_98912603 | TACATACGTTGAACATTATG | Intron1 |
| 126 | EIF4E_98913964 | CGTTTATGATGTAAGCACTA | Intron1 |
| 127 | EIF4E_98917268 | AGTTCAGCTTTAATCCAATC | Intron1 |
| 128 | EIF4E_98920149 | GGAGATAGGTTTTCCACATT | Intron1 |
| 129 | EIF4E_98920153 | ATAGGTTTTCCACATTAGAC | Intron1 |
| 130 | EIF4E_98925375 | AGAAACACGACCTACTGGAG | Intron1 |
| 131 | EIF4E_98901927 | TTAGATTCCGTTTTCTCCTC | EXON2 |
| 132 | EIF4E_98901929 | AGATTCCGTTTTCTCCTCTT | EXON2 |
| 133 | EIF4E_98901937 | TTTTCTCCTCTTCTGTAGTC | EXON2 |
| 134 | EIF4E_98901940 | TCTCCTCTTCTGTAGTCGGG | EXON2 |
| 135 | EIF4E_98901943 | CCTCTTCTGTAGTCGGGGGA | EXON2 |
| 136 | EIF4E_98901946 | CTTCTGTAGTCGGGGGATTA | EXON2 |
| 137 | EIF4E_98901950 | TGTAGTCGGGGGATTAGGAG | EXON2 |
| 138 | EIF4E_98901953 | AGTCGGGGGATTAGGAGTAG | EXON2 |
| 139 | EIF4E_98891637 | GGTGATTGCCACTAGCCAAA | Intron2 |
| 140 | EIF4E_98891970 | CGGAATTCACAGAAATGACG | Intron2 |
| 141 | EIF4E_98893710 | GCTTCAAAGTCATCAATACG | Intron2 |
| 142 | EIF4E_98894256 | AGTCATTGGCTGCAAGATCC | Intron2 |
| 143 | EIF4E_98897774 | TTCATCTGCCACTGTAAGCC | Intron2 |
| 144 | EIF4E_98897930 | TAAGCAGTGTATGATGTTAA | Intron2 |
| 145 | EIF4E_98900200 | GTTAAACTATATAAGACTGC | Intron2 |
| 146 | EIF4E_98900208 | ATATAAGACTGCCTCTAACG | Intron2 |

TABLE 2 -continued

| SEQ ID NO | Id | Nucleotide sequence (5'->3') | Target Position |
|---|---|---|---|
| 147 | EIF4E_98901760 | CCTCAACCTTAGCATATCTA | Intron2 |
| 148 | EIF4E_98901769 | TAGCATATCTAAAACTAGTC | Intron2 |
| 149 | EIF4E_98901104 | GACATCTTGCTTCATTTGAC | Intron2 |
| 150 | EIF4E_98887991 | GTAATATAGAGTTTAGGTGC | Intron3 |
| 151 | EIF4E_98887997 | TAGAGTTTAGGTGCTTACAT | Intron3 |
| 152 | EIF4E_98888000 | AGTTTAGGTGCTTACATATA | Intron3 |
| 153 | EIF4E_98888635 | CGATGACTTAGTTGCTTGCC | Intron3 |
| 154 | EIF4E_98888641 | CTTAGTTGCTTGCCTGAAGG | Intron3 |
| 155 | EIF4E_98889221 | CACAAATATAGTTTAGGTGA | Intron3 |
| 156 | EIF4E_98889228 | ATAGTTTAGGTGAGACAACC | Intron3 |
| 157 | EIF4E_98890236 | ATGAGCAGAATATCTTGAGG | Intron3 |
| 158 | EIF4E_98890336 | TTAGATAACTGCTAGGTAAT | Intron3 |
| 159 | EIF4E_98890730 | GAGGTTGATCAAAGTATAAT | Intron3 |
| 160 | EIF4E_98887924 | TACTAGACAACTGGATATGG | Exon4 |
| 161 | EIF4E_98887927 | TAGACAACTGGATATGGTTG | Exon4 |
| 162 | EIF4E_98887930 | ACAACTGGATATGGTTGTAC | Exon4 |
| 163 | EIF4E_98887933 | ACTGGATATGGTTGTACAGA | Exon4 |
| 164 | EIF4E_98887357 | GCATGACATTGCAGAATTAG | Intron4 |
| 165 | EIF4E_98887647 | AGACTGGATAATCAAAGCTC | Intron4 |
| 166 | EIF4E_98887648 | GACTGGATAATCAAAGCTCT | Intron4 |
| 167 | EIF4E_98887092 | AAGCGATCGAGGTCACTTCG | Exon5 |
| 168 | EIF4E_98887095 | CGATCGAGGTCACTTCGTCT | Exon5 |
| 169 | EIF4E_98887098 | TCGAGGTCACTTCGTCTCTG | Exon5 |
| 170 | EIF4E_98887101 | AGGTCACTTCGTCTCTGCTG | Exon5 |
| 171 | EIF4E_98887103 | GTCACTTCGTCTCTGCTGTT | Exon5 |
| 172 | EIF4E_98885135 | TTTGCATAGAAACTAAAGGC | Intron5 |
| 173 | EIF4E_98885140 | ATAGAAACTAAAGGCAGTTT | Intron5 |
| 174 | EIF4E_98885275 | TTGGCAGTTAATGTCATGGC | Intron5 |
| 175 | EIF4E_98885278 | GCAGTTAATGTCATGGCAGA | Intron5 |
| 176 | EIF4E_98885327 | TGCTCTGCTGCTGCTTATAT | Intron5 |
| 177 | EIF4E_98886329 | TGTCTTGTAAAGCCAGAAGT | Intron5 |
| 178 | EIF4E_98884989 | CTCTAACATTAACAACAGCG | Exon6 |
| 179 | EIF4E_98884993 | AACATTAACAACAGCGCCAC | Exon6 |
| 180 | EIF4E_98884997 | TTAACAACAGCGCCACATAC | Exon6 |
| 181 | EIF4E_98885000 | ACAACAGCGCCACATACATC | Exon6 |
| 182 | EIF4E_98885005 | AGCGCCACATACATCATCAC | Exon6 |
| 183 | EIF4E_98881534 | GACCTGTATCACATGCATAC | Intron6 |
| 184 | EIF4E_98881537 | CTGTATCACATGCATACTTA | Intron6 |

TABLE 2 -continued

| SEQ ID NO | Id | Nucleotide sequence (5'->3') | Target Position |
|---|---|---|---|
| 185 | EIF4E_98881795 | TTTCAAGTAAGACATGACTC | Intron6 |
| 186 | EIF4E_98881800 | AGTAAGACATGACTCTATTG | Intron6 |
| 187 | EIF4E_98882037 | TGAGATAAAGCTGACAAGGT | Intron6 |
| 188 | EIF4E_98882042 | TAAAGCTGACAAGGTTTCAG | Intron6 |
| 189 | EIF4E_98884156 | TTAATGAAAATTATACGTAG | Intron6 |
| 190 | EIF4E_98884163 | AAATTATACGTAGTAAACAC | Intron6 |
| 191 | EIF4E_98873115 | CAACCTTCATAAAAGTACTA | Exon7 |
| 192 | EIF4E_98874238 | TGCCACTTGATACTGCTGAA | Exon7 |
| 193 | EIF4E_98875120 | AGTTTCTAGACACGTACAAG | Exon7 |
| 194 | EIF4E_98875416 | ACTTTACTTGGACAATCATA | Exon7 |
| 195 | EIF4E_98877382 | CTTTTGAATGCAACTTTAGC | Exon7 |
| 196 | EIF4E_98879129 | TATGTACAGTATGCTGAGAT | Exon7 |
| 197 | EIF4E_98879807 | CTAAGACTGAATGACTGTGC | Exon7 |
| 198 | EIF4E_98879820 | ACTGTGCCTTACTTTATAAA | Exon7 |
| 199 | EIF4E_98880301 | CACTGATTTGAATGAAATGC | Exon7 |
| 200 | EIF4E_98880973 | CCAAATCTCGATTGCTTGAC | Exon7 |

The delivery of a therapeutically effective dose of the oligonucleotide according to the present invention into cells may be achieved by subcutaneous injection, intravenous injection, intramuscular injection, intra-arterial injection, intraperitoneal injection, intracerebral injection, intrathecal injection, or intracerebroventricular injection. Because an eIF4E inhibitor is known as an anticancer agent in addition to acting on the nervous system, intravenous injection allows the anticancer activity to be effectuated, but the eIF4E inhibitor cannot cross the brain blood bather into the brain. Hence, intracerebral injection, intrathecal injection, or intracerebroventricular injection is preferable, with more preference for intrathecal injection.

The pharmaceutical composition comprising an eIF4E inhibitor according to the present disclosure may be variously formulated together with a pharmaceutically acceptable carrier by methods known in the art, depending on administration routes. The carrier includes all types of solvents, dispersive media, oil-in-water or water-in-oil emulsions, aqueous compositions, liposomes, microbeads, and microsomes.

The pharmaceutical composition according to the present disclosure may be administered in a pharmaceutically effective amount, that is, an amount sufficient to prevent, alleviate, or treat epilepsy or a symptom thereof. By way of example, the composition may be administered at a daily dose of 0.01 to 1000 mg/kg and preferably at a daily dose of 1 to 100 mg/kg. The pharmaceutical composition of the present disclosure may be administered once or divided into multiple doses within a desired dose range. However, the dose of the composition according to the present invention may be properly selected by a person skilled in the art depending on the route of administration, subject to be administered, age, sex, body weight, individual difference, and disease state.

In addition, the pharmaceutical composition according to the present invention may be administered orally or parenterally. Moreover, the administration of the pharmaceutical composition according to the present disclosure can be made with the aid of any device capable of delivering the active ingredient to target cells. The pharmaceutical composition according to the present disclosure may be formulated into suitable dosage forms depending on various administration routes.

In accordance with an embodiment thereof, the present disclosure provides at least one biomarker selected from the group consisting of eIF4E, eIF4E activation-sensitive proteins, and nucleic acid molecules coding therefor. The biomarker can be used in probing, detecting, or diagnosing a brain disease caused by increased eIF4E activity, for example, FMCD, a symptom of FMCD, or an associated disease thereof.

Thus, contemplated according to an embodiment of the present disclosure is a composition or kit for diagnosis of a brain disease associated with increased activity of eIF4E, for example, FMCD, a symptom of FMCD, or an associated disease thereof, the composition or kit comprising a molecule or agent capable of detecting the biomarker, or a method for diagnosing or providing diagnostic information on a brain disease associated with increased activity of eIF4E, for example, FMCD, a symptom of FMCD, or an associated disease thereof or a method for providing diagnostic information on a brain disease associated with increased activity of eIF4E, for example, FMCD, a symptom of FMCD, or an associated disease thereof, the method using a molecule or agent capable of detecting the biomarker. An additional embodiment of the present disclosure pertains to a composition or kit comprising a molecule or agent capable of the biomarker for probing, detecting, or diagnosing a brain disease associated with increased activity of eIF4E, for example, FMCD, a symptom of FMCD, or an associated disease thereof Another embodiment of the present disclosure pertains to a method for selecting a subject to be administered an eIF4E inhibitor, for predicting susceptibility of a subject to an eIF4E inhibitor, or for monitoring administration efficacy of an eIF4E inhibitor in a subject, the method using at least one biomarker selected from the group consisting of eIF4E, eIF4E activation-sensitive proteins the expression or to activity of which is regulated by eIF4E, and a nucleic acid molecule coding therefor.

In an embodiment of the present disclosure, the method comprises the steps of measuring the biomarker for activity, expression, or concentration level in a biological test sample from a test subject and comparing measurements of the activity, expression, or concentration level of the biomarker between the test sample and a reference sample.

In addition, the method may further comprise the steps of: selecting a subject in need of an eIF4E inhibitor; and administering the eIF4E inhibitor to the selected subject when the activity, expression, or concentration level of the biomarker is higher in the biological sample from the test subject than the reference sample in the comparing step. The reference sample may be obtained from a subject free of a brain disease associated with increased activity of eIF4E, a symptom thereof, or an associated disease thereof. The test sample may be obtained from a subject that has a risk of onset of a disease associated with increased activity of eIF4E, a symptom thereof, or an associated disease thereof, or has undergone surgery due to of a disease associated with increased activity of eIF4E.

As used herein, the term "sample from a patient" or "sample from a subject" refers to a sample such as a tissues or cell from which a biomarker protein or gene can be detected, and is intended to encompass a brain tissue, a brain cell, a brain tissue homogenate, or a cerebrospinal fluid, but without limitations thereto.

The brain disease associated with increased activity of eIF4E, for example, FMCD, a symptom of FMCD, or an associated disease thereof, eIF4E, eIF4E hyperactivation-sensitive proteins, and nucleic acid molecules coding therefor are as described above.

The molecule or agent capable of detecting a biomarker according to the present invention may be a primer, a probe, or an aptamer capable of hybridizing with the biomarker, or an antibody or aptamer binding specifically to the biomarker.

In detail, "agent capable of detecting a gene" in the present disclosure means a substance available for detecting a target gene in a sample of interest. In a concrete embodiment, the agent may be a primer, a probe, an antisense oligonucleotide, or an aptamer that can bind complementarily to a nucleic acid sequence of a target gene. The primer, the probe, or the antisense oligonucleotide binds specifically to a target gene, but preferably not to other nucleic acid sequences. The probe may be constructed into a form of an oligonucleotide probe, a single-stranded DNA probe, a double-stranded DNA probe, or an RNA probe. In the present disclosure, the diagnosis may be made by determining hybridization between the target gene and a probe, primer, or antisense oligonucleotide complementary thereto. Selection of suitable sequences and hybridization conditions may be modified based on knowledge in the art.

In the diagnostic composition, the diagnostic kit, the diagnostic method, and the method of providing diagnostic information for a brain disease associated with increased activity of eIF4E, for example, FMCD, a symptom of FMCD, or an associated disease thereof, the detection of a biomarker gene in a sample derived from a subject may be carried by amplifying a nucleic acid sequence from a sample of a patient, and/or determining the sequence of amplified nucleic acids.

In detail, the nucleic acid amplification may be carried out by polymerase chain reaction (PCR), multiplex PCR, touchdown PCR, hot start PCR, nested PCR, booster PCR, real-time PCR, differential display PCR (DD-PCR), rapid amplification of cDNA ends (RACE), inverse PCR, vectorette PCR, thermal asymmetric interlaced PCR (TAIL-PCR), ligase chain reaction, repair chain reaction, transcription-mediated amplification, self-retaining sequence replication or selective amplification reaction of a target sequence.

In addition, the step of sequencing an amplicon may be performed by Sanger sequencing, Maxam-Gilbert sequencing, Shotgun sequencing, pyrosequencing, hybridization by microarray, allele specific PCR, dynamic allele-specific hybridization (DASH), PCR extension analysis, TaqMan® method, automatic sequence analysis or next generation sequencing. The next generation sequencing may be conducted using a sequence analysis system widely used in the art, and for example, 454 GS FLX of Roche Company, Genome Analyzer of Illumina Company, SOLid Platform of Applied Biosystems Company, and the like may be used.

Herein, "agent capable of detecting a gene" means a substance which can be used for detecting a target protein in a sample of interest. Preferably, the agent may be a specific compound, a peptide, an antibody, an aptamer, or a synthetic material that targets the target protein. The antibody may be polyclonal or monoclonal.

In addition, the composition comprising an agent capable of detecting a target gene or protein for diagnosis of epilepsy may be provided in the form of a kit. The kit may comprise a composition, solution or device containing one or more different ingredients suitable for analysis as well as the agent, capable of detecting a gene or protein, including a primer, a probe, an antisense nucleic acid, an aptamer, an antibody, a peptide, and a compound for detecting a mTOR activation-sensitive gene or protein.

The detection of the eIF4E activation-sensitive protein or a nucleic acid molecule coding therefor can be performed by detecting a downstream gene in the eIF4E signaling pathway, thereby achieving minimally invasive diagnosis without resection of a brain tissue and having advantage over conventional gene detection methods in terms of time and cost.

Effect of the Invention

In the present disclosure, eIF4E is identified as a novel therapeutic target for intractable epilepsy as demonstrated by pharmacological or genetic inhibition, and epilepsy can be inhibited using an eIF4E repressor or an eIF4E inhibitor.

BRIEF DESCRIPTION OF THE DRAWINGS

FIGS. 9*c* and 9*d* shows decreased eIF4E expression in the brain tissues at postnatal day 21 from animal models established in Examples 1-6 and 2-1 using pCIG-MTOR mutant-IRES-GFP; mU6-sheIF4E vector of Example 2-1.

FIG. 20*a* shows a distribution of ASO through the fluorescence of Cy3 that was labeled to the ASO, in a normal mouse; and FIG. 20*b* shows the penetration of ASO labeled with Cy3 (red) into the mutant-expressing cells (GFP labeled) of the p.C1483Y and p.L2427P mice in Example 1.

DETAILED DESCRIPTION

Figure 1:
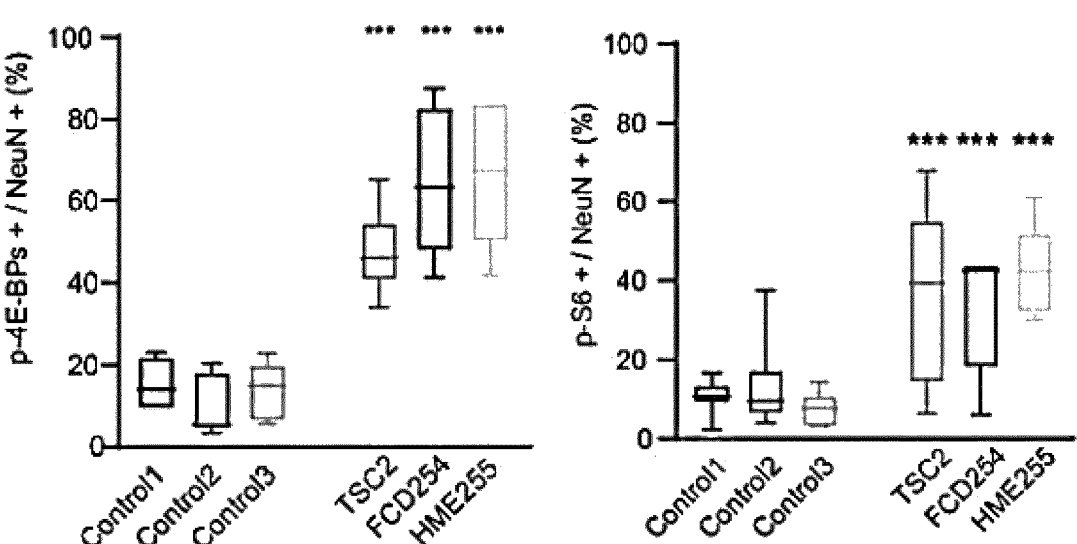
FIG. 1 shows increased expression levels of phosphorylated 4E-BP1/2/3(4E-BPs) and S6 in brain tissues from TSC, FCD, and HME patients, as measured by immunofluorescence analysis, wherein control 1 refers to the postmortem brain tissues of UMB5309, control 2 to the postmortem brain tissue of UMB5408, and control 3 to an unaffected brain tissue of FCD247.

A better understanding of the present disclosure may be obtained in light of following examples which are set forth to illustrate, but are not to be construed to limit, the present disclosure.

<Example 1> Imaging Analysis of Protein Expression in FMCD Patients' Brain Tissues with Mutations in mTOR 1-1: Selection of Subject Individuals diagnosed with HME, FCD, or TSC who had undergone epilepsy surgery at the Severance Children's Hospital since 2004 were identified. Enrolled individuals met the study entry criteria for FCDII and underwent extensive presurgical evaluations, including video-EEG monitoring, high-resolution MRI, fluorodeoxyglucose proton emission tomography, and subtraction ictal single-photon emission computed tomography, coregistered to MRI, to localize anatomic lesions. Complete resection was defined as resection of all areas of seizure-onset and irritative zones on intracranial EEG.

Pathological diagnoses of studied individuals with HME, FCD, or TSC were reconfirmed for the present disclosure according to the recent consensus classification by the International League Against Epilepsy Diagnostic Methods Commission. The study was performed and all human tissues were obtained in accordance with protocols approved by Severance Children's Hospital and the Korea Advanced Institute of Science and Technology (KAIST) Institutional Review Board and Committee on Human Research. Informed consent was obtained from the parents of individuals with HME, FCD, and TSC. Healthy adult, control brain samples were obtained from the University of Maryland Brain and Tissue Bank: brain tissues of individuals without neurological disease were obtained.

Specifically, clinical information of the patients for the samples used in this test is given in Table 3, below. In this table, the UMB groups stand for healthy adult control brain samples that were obtained from the University of Maryland Brain and Tissue Bank.

TABLE 3

| Patient ID | Age | Sex | Age at first seizure | Age at surgery | Seizure frequency | Tissue region | Etc |
|---|---|---|---|---|---|---|---|
| UMB1712 | 20 Y | male | — | — | — | Frontal | Post-mortem tissues |
| UMB4917 | 22 Y | male | — | — | — | Frontal | Post-mortem tissues |
| UMB5309 | 14 Y | female | — | — | — | Temporal | Post-mortem tissues |
| UMB5408 | 6 Y | male | — | — | — | Temporal | Post-mortem tissues |
| FCD56 | 10 Y | female | 2 Y | 6 Y | 3/day | Frontal | — |
| FCD247 | 11 Y | female | 1 Y | 9 Y | N.A. | Temporal | — |
| FCD254 | 12 Y | male | 4 Y | 9 Y | 10/day | Frontal | — |
| FCD348 | 6 Y | male | 4 Y | 5 Y | N.A. | Frontal | — |
| HME20 | 5 Y | female | 2 M | 9 M | 10/day | Frontal | — |
| HME255 | 20 Y | female | 8 Y | 17 Y | 3/day | Temporal | — |
| HME338 | 17 Y | female | 5 Y | 15 Y | N.A. | Temporal | — |
| TSC2 | 8 Y | female | 2 Y | 4 Y | N.A. | Temporal | — |
| TSC264 | 2 Y | female | 1 Y | 1 Y | 6/day | Frontal | — |
| TSC357 | 20 Y | male | 1 Y | 1 Y | N.A. | Frontal | — |

1-2: Mutation Test

For the patients TSC2, FCD254, HME255, TSC264, and TSC357 in Table 4 of Example 1-1, mutation information was confirmed by WES (whole exome sequencing), panel sequencing, and amplicon sequencing. Concrete analysis results are summarized in Table 4, below. From the patients, selection was made of patients diagnosed with tuberous sclerosis (TSC), focal cortical dysplasia (FCD), and hemimegalencephaly (HME). The selected TSC, FCD, and HME patients are indicated by TSC2, FCD254, and HME255, respectively.

TABLE 4

| Patient ID | Sequencing | Mutation type | Mutated gene | Nucleotide changes | Protein change | Frequency (%) |
|---|---|---|---|---|---|---|
| TSC2 | Whole exome sequencing | Germline | TSC2 | c.3355C > T | p.Gln1119* | 36.75 |
| FCD254 | Targeted hybrid capture sequencing | Somatic | MTOR | c.4376C > A | p.Ala1459Asp | 3.29 |
| HME255 | Targeted hybrid capture sequencing | Somatic | MTOR | c.4448G > A | p.Cys1483Tyr | 9.43 |
| TSC264 | Targeted hybrid capture sequencing | Germline | TSC2 | c.3007delG | p.Ala1003fs | 10.86 |
| TSC357 | Targeted hybrid capture sequencing | Germline | TSC2 | c.5153A > C | p.His1718Pro | 31.99 |

1-3: Expression Levels of Phosphorylated 4E-BP1/2/3 (4E-BPs) and S6 in Patient Samples Using immunofluorescence staining, the FMCD epilepsy patients (TSC2, FCD254, and HME255) in Example 1-1 were identified to increase in the phosphorylation of 4E-BPs and increase in the phosphorylation of S6 (FIG. 1). The same pattern was observed in an animal model characterized by increased eIF4E activity induced by the phosphorylated proteins.

In brief, samples were obtained by resecting lesion tissues from the TSC2, FCD254, and HME255 patients selected in Example 1-1 and subjected to immunofluorescence staining. Samples were obtained by resecting lesion tissues from patients suffering from the diseases and subjected to immunofluorescence staining. The immunofluorescence-stained tissues were quantitated for p-4E-BPs-positive or p-S6-positive cells among NeuN-positive neuronal cells in the average of 2-5 cortical regions, and the measurements are expressed as percentages in FIG. 1.

For mouse brain blocks, a brain tissue was harvested at the time of investigation and fixed in freshly prepared phosphate-buffered 4% paraformaldehyde for 2 hours, cryo-protected overnight in 30% buffered sucrose, frozen in OCT on thy ice, and stored at −80° C. Cryostat-cut sections (20-μm thick) were collected and placed on glass slides.

Tissue sections were blocked in phosphate buffered saline (PBS)-GT (0.2% gelatin and 0.2% Triton X-100 in PBS) for 1 hour at room temperature, incubated in a diluted primary antibody in blocking buffer at 4° C. overnight, and washed in PBS (3×5 minutes), followed by reaction with a diluted secondary antibody in blocking buffer for 1 hour at room temperature. After an additional round of washing, the coverslips were mounted onto a mounting solution containing DAPI (P36931, Life Technologies).

Among the antibodies used, there were antibodies against phosphorylated S6 (Ser240/244) (Cell signaling, 5364, 1:800), phosphorylated 4E-BP (Thr37/46) (Cell Signaling, 2855, 1:200), and NeuN (Millipore, MAB377, 1:100). The samples were washed with PBS and stained with the following secondary antibodies: Alexa Fluor® 594-conjugated goat anti-rabbit antibody (1:200 diluted, A11012, Thermo scientific) and Alexa Fluor® 488-conjugated goat anti-rabbit antibody (1:200 diluted; A11001, Thermo scientific). A mounting solution containing DAPI (P36931, Life Technology) was used for nuclear staining. Confocal images were obtained with a Zeiss LSM780 or LSM800 (Carl Zeiss) confocal microscope with sequential acquisition set at a resolution of 2048×2048 pixels.

Cells positive for NeuN, phosphorylated S6 (Ser240/244), and phosphorylated 4E-BP (Thr37/46) were counted using a ×10 or ×20 objective lens. Four or five fields were acquired per a subject.

FIG. 1 shows increased expression levels of phosphorylated 4E-BP1/2/3(4E-BPs) and S6 in brain tissues from the selected TSC2, FCD254, and HME255 patients, as measured by immunofluorescence analysis. In the box plots of FIG. 1, control 1 refers to the postmortem brain tissues of UMB5309, control 2 to the postmortem brain tissue of UMB5408, and control 3 to an unaffected brain tissue of FCD247. The selected TSC2, FCD254, and HME255 patients were all observed to have increased levels of phosphorylated 4E-BP and S6, indicating that mTOR activation occurs in the brain lesions of all of the corresponding patients. Increased phosphorylation of 4E-BP and S6 leads to an increase in the activity of the eIF4F complex including eIF4E.

When activated, mTOR, which is a kinase targeting 4E-BP1/2/3(4E-BPs) and S6K, induces the phosphorylation of 4E-BP1/2/3 and S6. When phosphorylated, 4E-BP1/2/3 is inactivated, leading to the activation of eIF4E on which 4E-BP1/2/3(4E-BPs) acts as a repressor. Meanwhile, eIF4B is activated to help the function of eIF4E. S6K phosphorylates S6 and eIF4B which, in turn, increases the activity of eIF4E. eIF4B increases the activity of the eIF4F complex which includes eIF4E as a key component.

1-4: Western Blot Analysis for Expression of ADK, CREB1, and IRSp53 in Patient Sample eIF4E hyperactivation resulted in an increase in the expression of the eIF4E activation-sensitive genes ADK, CREB1, and IRSp53 in the FMCD epilepsy patients of Example 1-1, as measured by translatome profiling analysis (FIG. 2).

A translatome is composed of all mRNA fragments that are translated in a moment or condition in a single cell. Usually, a translatome profiling or ribosome profiling technique is used to acquire the translatome information. Tranlsatome profiling is a technique for analyzing the translation of mRNA into proteins at the genomic level.

Figure 2:
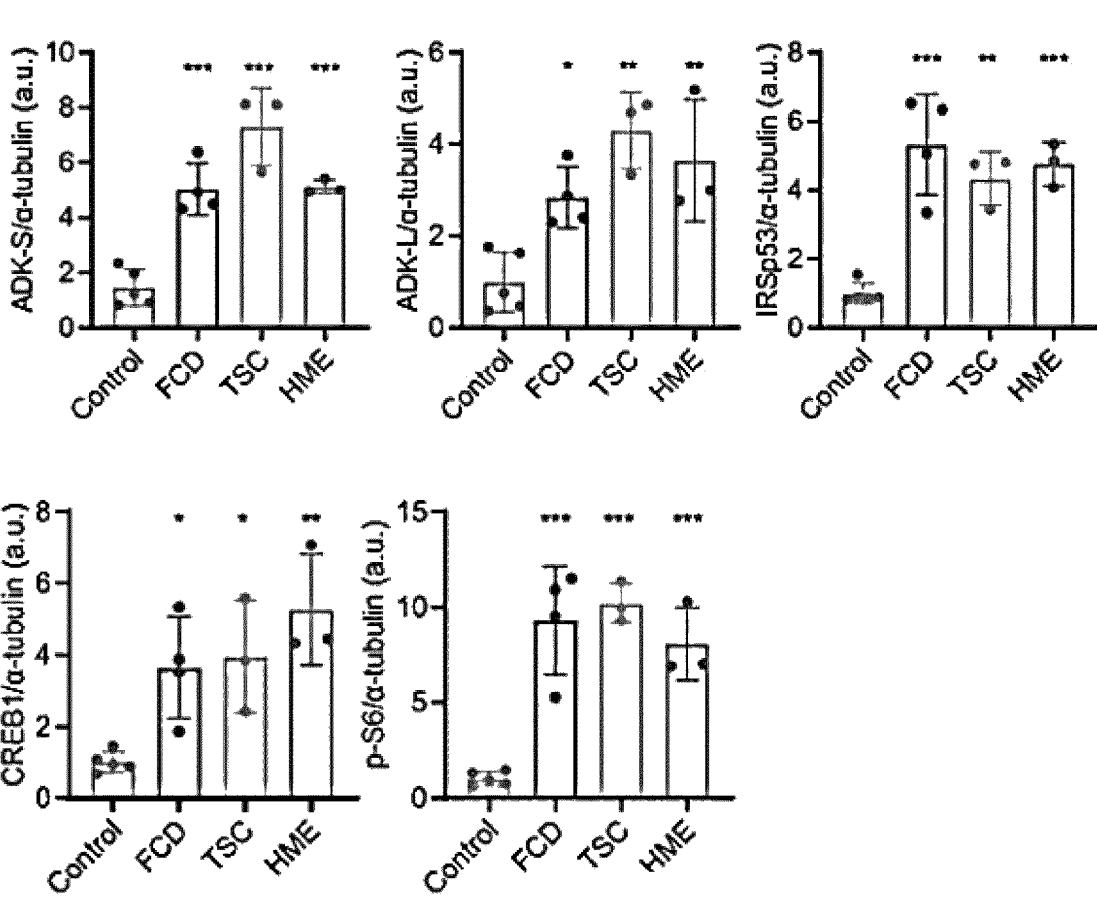
FIG. 2 shows increased expression levels of ADK, IRSp53, CREB1, and p-S6 in protein solutions obtained from brain tissues of TSC, FCD, and HME patients, as measured by western blot analysis, wherein α-tubulin was used as a loading control, and control 1 refers to the postmortem brain tissues of UMB5309, control 2 to the postmortem brain tissue of UMB5408, control 3 to an unaffected brain tissue of FCD247, control 4 to the postmortem brain tissue of UMB1712, and control 5 to the postmortem brain tissue of UMB4917.

FIG. 2 shows bar graphs in which mTOR activity is identified by western blot analysis for proteins extracted from brain tissues of the FMCD patients and expression levels of ADK, IRSp53, CREB1, and p-S6 are quantitated and presented as percentage changes relative to the average of control samples (* P<0.05,  P<0.01, and * P<0.001 (one-way analysis of variance with Bonferroni post-hoc test). Mean±s.e.m.). In FIG. 2, α-tubulin was used as a loading control.

Antibodies used in this analysis included antibodies against ADK (Human atlas, HPA038409, 1:500), IRSp53 (Novus, NBP1-88711, 1:1000), CREB1 (Cell signaling, 9197, 1:1000), and phosphorylated S6 (Ser240/244) (Cell signaling, 5364, 1:1000).

In FMCD epilepsy patients, eIF4E hyperactivation was observed to increase expression levels of the eIF4E hyper-activation-sensitive genes ADK, CREB1, and IRSp53 as analyzed by translatome profiling (FIG. 2). In this regard, experiments of Example 12 conducted on wild-type ADK-S, CREB1, and IRSp53 and their variants having the motif-deleted 5'-UTR showed that when the specific motifs were deleted from the mTOR hyperactivation-sensitive genes the translation of which is regulated by eIF4E, the expression upregulation of the genes by mTOR mutation and eIF4E hyperactivation disappeared. The data implicate that ADK, CREB1, and IRSp53 have a common motif which plays a role in upregulating the expression of the genes by eIF4E activation. The expression upregulation of ADK, CREB1, and IRSp53 in the patient samples is accounted for by eIF4E activation.

Figure 3:
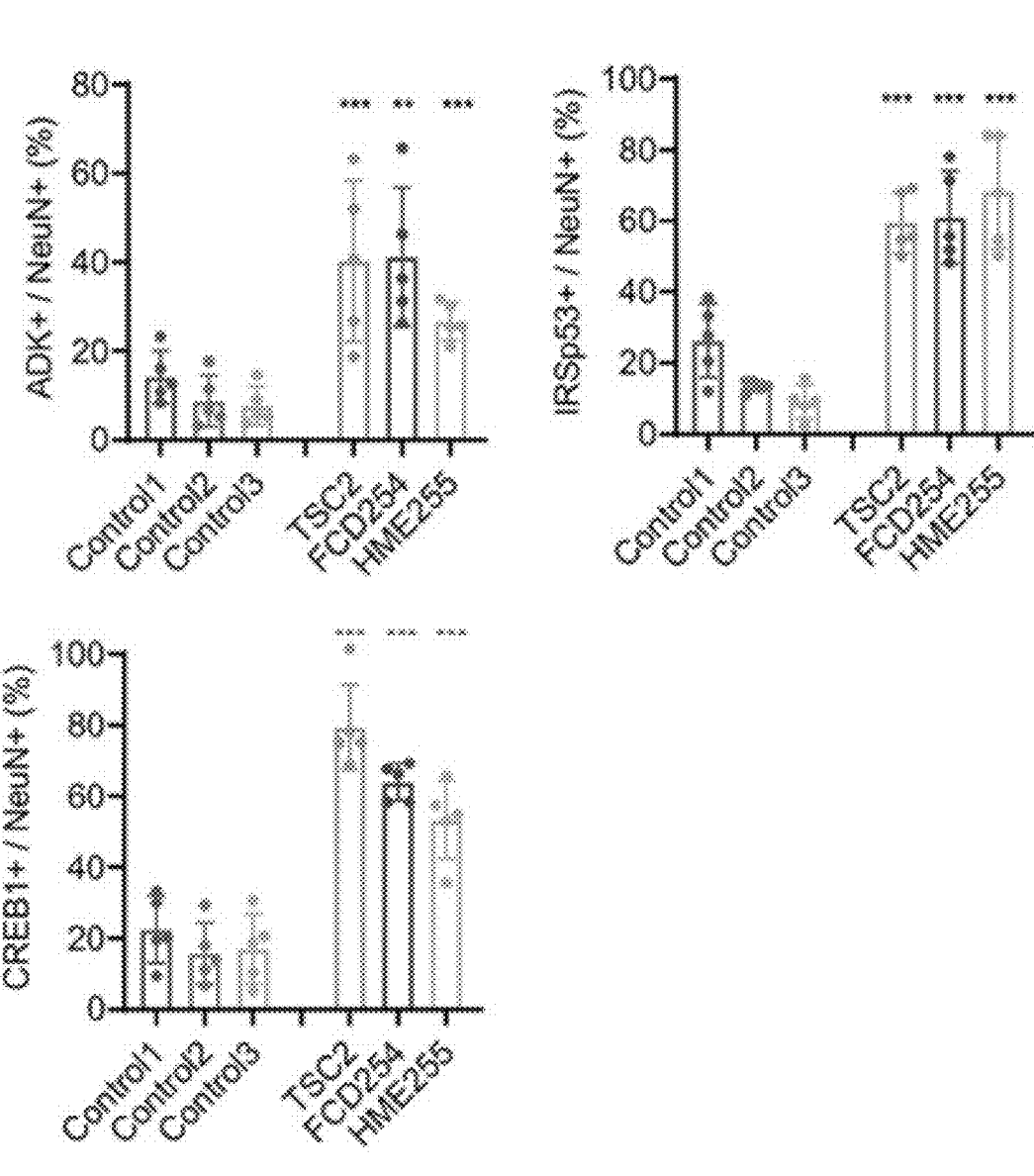
FIG. 3 shows increased expression levels of ADK, IRSp53, and CREB1 in lesion tissues of TSC, FCD, and HME patients, as measured by immunofluorescence analysis wherein control 1 refers to the postmortem brain tissues of UMB5309, control 2 to the postmortem brain tissue of UMB5408, and control 3 to an unaffected brain tissue of FCD247.

1-5: Immunofluorescence Analysis for Expression of ADK, CREB1, and IRSp53 in Patient Sample Using immunofluorescence staining, the FMCD epilepsy patients (TSC2, FCD254, and HME255) in Example 1-1 were identified to increase in the expression of ADK, IRSp53, and CREB (FIG. 3). The same protein expression pattern was observed in an animal model characterized by increased eIF4E activity induced by the phosphorylated proteins.

Samples were obtained by resecting lesion tissues from the TSC2, FCD254, and HME255 patients selected in Example 1-1 and subjected to immunofluorescence staining in the same manner as in Example 1-3. Samples were obtained by resecting lesion tissues from patients suffering from the diseases and subjected to immunofluorescence staining. The immunofluorescence-stained tissues were quantitated for ADK-, IRSp53-, or CREB1-positive cells among NeuN-positive neuronal cells in the average of 2-5 cortical regions, and the measurements are expressed as percentages in FIG. 3.

Among the antibodies used, there were antibodies against NeuN (Millipore, MAB377, 1:100), ADK (Human atlas, HPA038409, 1:200), CREB1 (Cell signaling, 9197, 1:800), and IRSp53 (Novus, NBP1-88711, 1:100). Cells positive for NeuN, ADK, CREB1, and IRSp53 were counted using a ×10 or ×20 objective lens. Four or five fields were acquired per subject.

In FIG. 3, control 1 refers to the postmortem brain tissues of UMB5309, control 2 to the postmortem brain tissue of UMB5408, and control 3 to an unaffected brain tissue of FCD247. As shown in FIG. 3, the neuronal cells of the TSC, FCD, and HME patients were observed to increase in the expression of ADK, IRSp53, and CREB1, compared to controls 1 to 3.

1-6: Comparison Between Patients and Animal Models

U.S. Pat. No. 9,629,346 discloses that FCD type II animal models having brain somatic mutations in mTOR (C1483Y or L2427P) exhibited mTOR hyperactivation through the phosphorylation of S6 protein.

Figure 4:
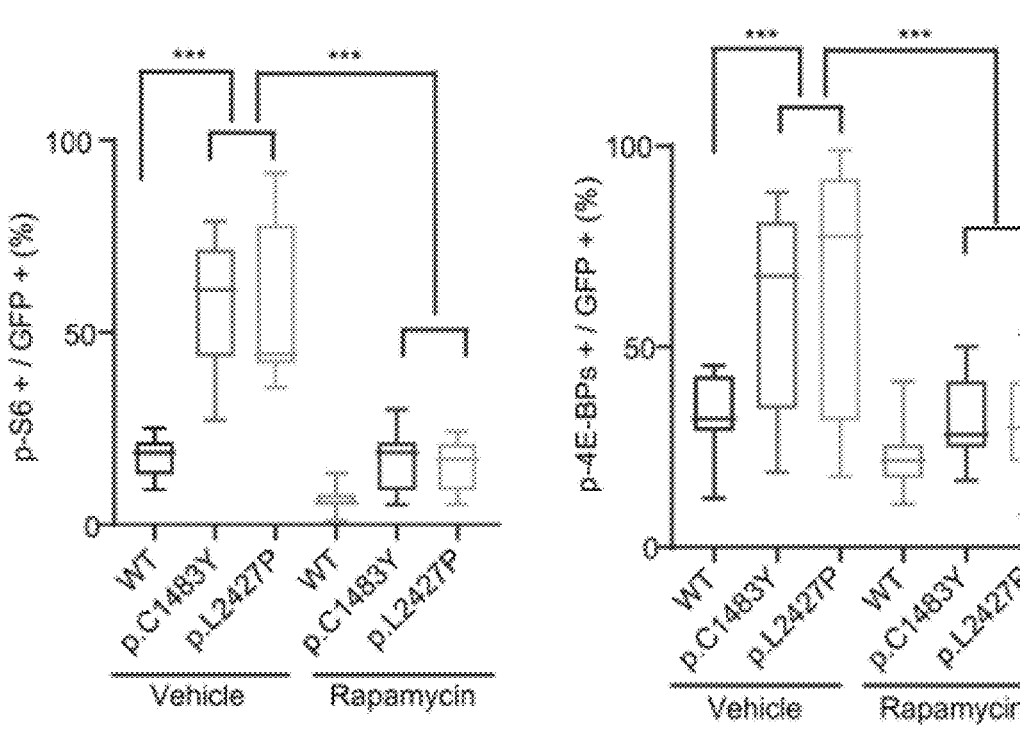
FIG. 4 shows the phosphorylation of 4E-BPs and the activation of S6K in the FMCD animal models (embryonic day 18), wherein the phosphorylation of 4E-BPs and the activation of S6K lead to increasing the activity of eIF4F including eIF4E.
Figure 5:
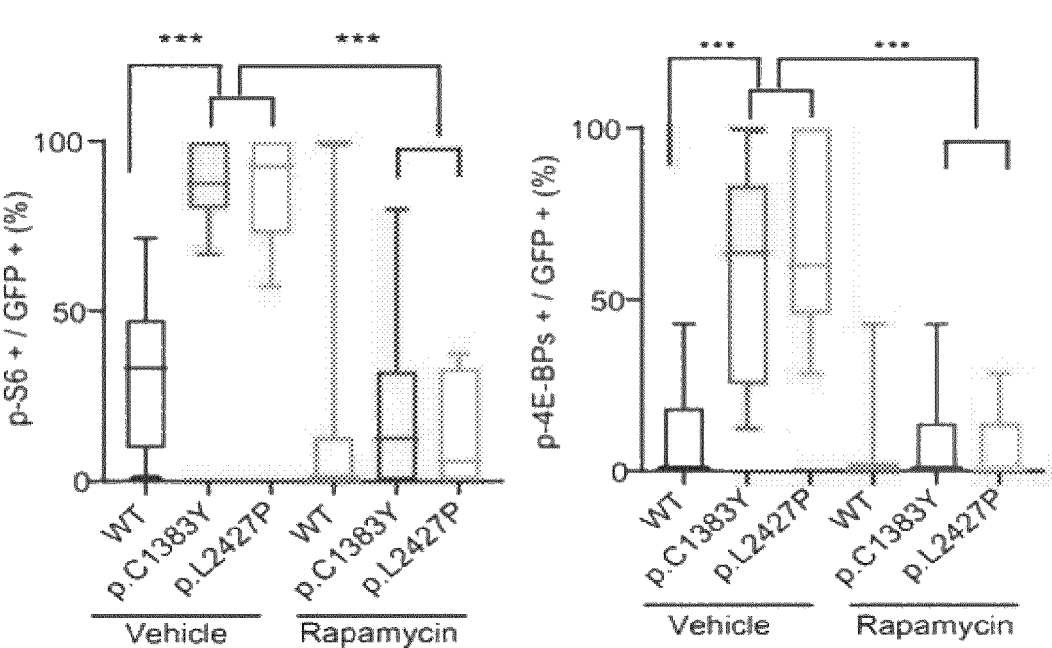
FIG. 5 shows the phosphorylation of 4E-BPs and the activation of S6K in the FMCD animal models (adult—at postnatal day 56 and 120), wherein the phosphorylation of 4E-BPs and the activation of S6K lead to increasing the activity of eIF4F including eIF4E.
Figure 6:
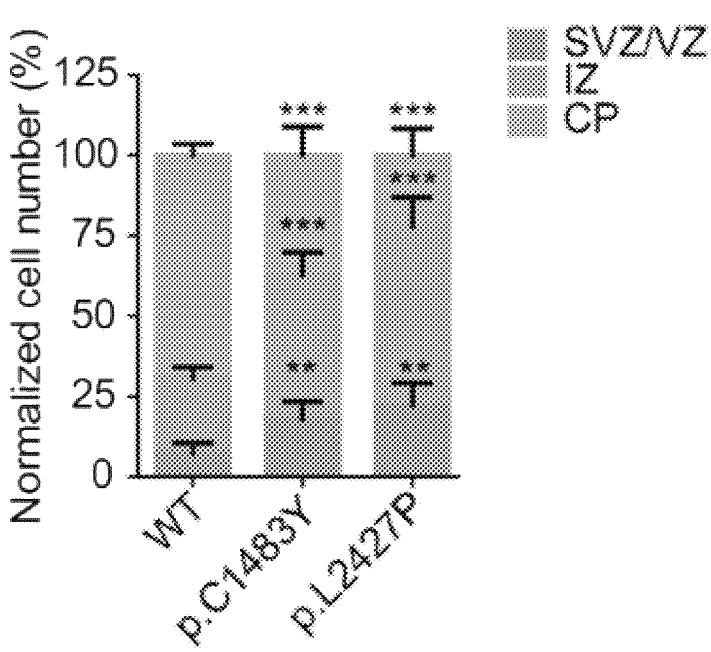
FIGS. 6 to 8 show the generation of cerebral cortical dysplasia, epilepsy, and cellular hypertrophy in FMCD animal models according to Example 1-6.

The results, obtained in Example 1-3, for the phosphorylation of 4E-BPs and the activation of S6K in the tissues of the FMCD patients (FIG. 1) were coincident with the phosphorylation of 4E-BPs and the activation of S6K in the FMCD animal models of FIGS. 4 and 5, in more detail, the FCD type II animal models in which mTOR was hyperactivated by introducing an mTOR mutant (C1483Y or L2427P). FIG. 4 shows the phosphorylation of 4E-BPs and the activation of S6K in the FMCD animal models (embryonic day 18) and FIG. 5 shows the phosphorylation of 4E-BPs and the activation of S6K in the FMCD animal models (adult—at postnatal day 56 and 120). The phosphorylation of 4E-BPs and the activation of S6K increased the activity of the eIF4F complex containing eIF4E.

In mice at embryonic day 18 (E18) and at postnatal days 56 to 120 (P56-P120), which had undergone in-utero electroporation at embryonic day 14 (E14), the mTOR hyperactivation due to mTOR mutation greatly increased levels of phosphorylated S6 protein and phosphorylated 4E-BP protein (FIGS. 4 and 5). Through this experiment, it was observed that in vivo mutation in mTOR causes mTOR hyperactivation, interrupting with normal cortical development.

Figure 7:
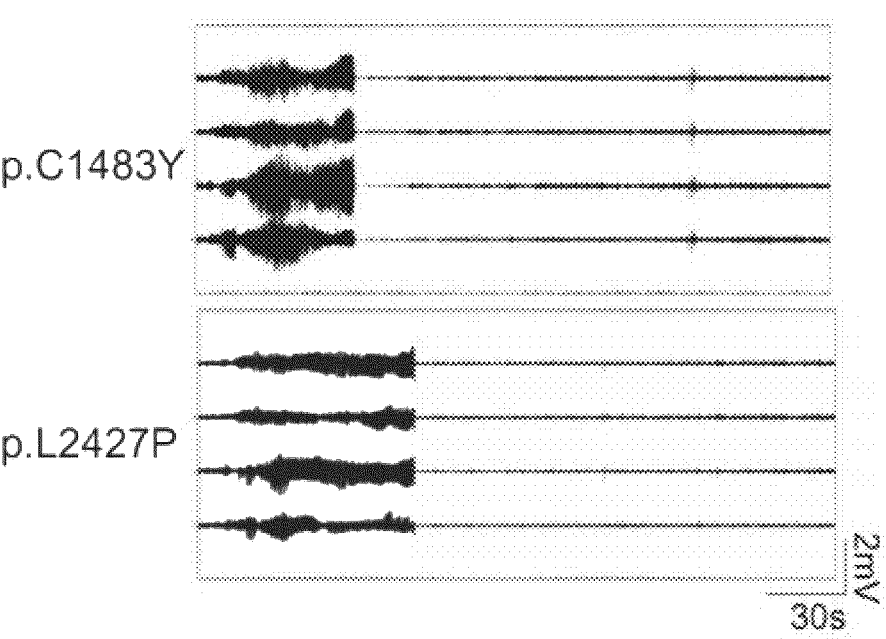

Video-Electroencephalography monitoring was carried out on the animal models. EEG signals from epidural electrodes positioned on the frontal lobes (AP 2.8 mm, ML±1.5 mm) and temporal lobes (anterior to posterior—2.4 mm, medial to lateral ±2.4 mm) were recorded using the cerebellum as a reference. After more than 10 days of recovery from the surgery, EEG signals were recorded for more than 2 days (12 hours per day) (FIG. 7). As a result, significantly defective neuronal migration was observed in the cerebral cortex of the mice and the animal models exhibited a typical seizure in the same pattern as in patients. In contrast, mice having a wild-type mTOR gene inserted thereinto did not show seizure. The significantly defective neuronal migration in the cerebral cortex indicates the disruption of cortical radial neuronal migration. The experimental results in the animal models are summarized in Table 5 below.

TABLE 5

| Group | No. of GFP + pups | No. of mice with seizure | % |
|---|---|---|---|
| Wild type | 8 | 0 | 0 |
| p.Cys1483Tyr | 15 | 14 | 93.3 |
| p.Leu2427Pro | 23 | 21 | 91.3 |

Figure 8:
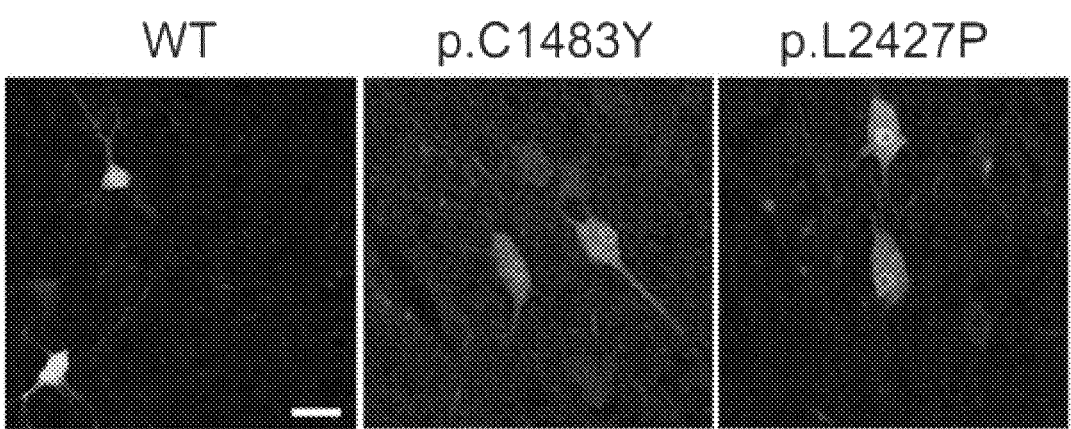

As can be seen in FIG. 8, the size of neurons from mice which had been electroporated with a plasmid carrying an mTOR mutant gene according to the present disclosure was significantly increased than that of normal neurons, whereas the size of neurons from mice having a wild-type mTOR gene introduced thereinto did not significantly changed. These results are consistent with the pattern of dysmorphic neuron in patients with malformations of cortical development, suggesting that epilepsy animal models can be generated using the mTOR mutants. The mice electroporated with a plasmid carrying an mTOR mutant gene significantly decreased in the number of dendritic branches, compared to normal neurons whereas the mice with wild-type mTOR gene were observed to remain unchanged in the number of synaptic spine.

<Example 2> Prevention of Epilepsy Onset
Through eIF4E Downregulation with sheIF4E
(Genetic Inhibition of eIF4E)

2-1: Preparation of eIF4E-Downregulated Animal Model Using sheIF4E

An examination was made to see whether the translation dysregulation mediated by eIF4F activating mutation induces the major phenotypes of FMCD, including epilepsy, cytomegalic dysmorphic neurons, and cortical dyslamination.

Figure 9A:
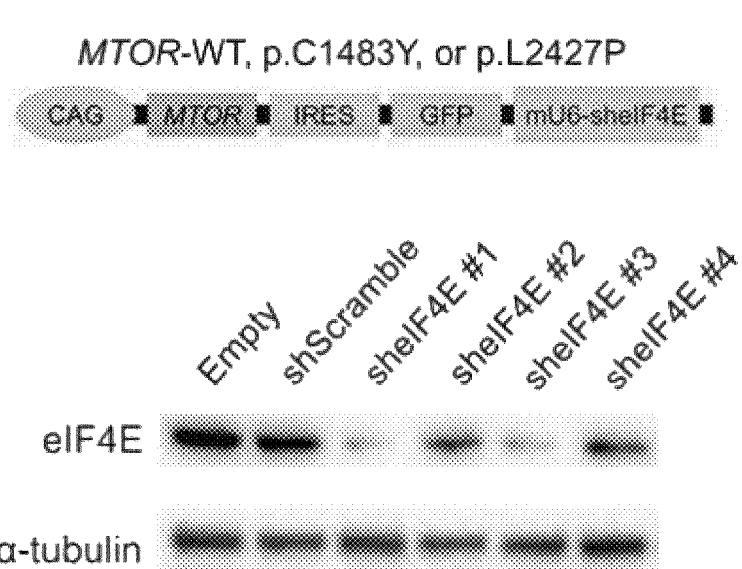
FIGS. 9*a* and 9*b* show pCIG-MTOR mutant-IRES-GFP; mU6-shScramble or pCIG-MTOR mutant-IRES-GFP; and mU6-sheIF4E vector construction according to Example 2 and inhibitory activity of sheIF4E against eIF4E, as measured by western blotting.
Figure 9B:
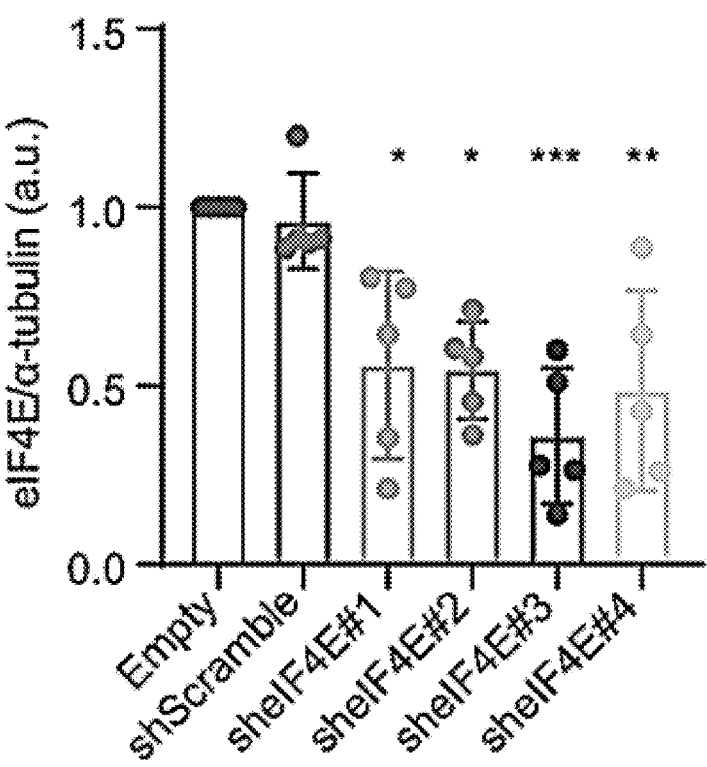

To this end, in vivo knockdown of eIF4E, which is a key component of the eIF4F complex, was performed to reduce eIF4F activity in FMCD mice via in utero electroporation of mTOR mutant or wild-type constructs co-expressing scrambled shRNAs (shScramble) or shRNAs against eIF4E (FIGS. 9a and 9b).

In brief, an FMCD epilepsy animal model for use in evaluating a therapeutic effect was prepared using a vector carrying mTOR mutation (C1483Y or L2427P) in the same manner in the disclosure of U.S. Pat. No. 9,629,346 on the FCD type II animal model of brain somatic mutation, wherein an shRNA sequence responsible for the translational downregulation of eIF4E was inserted into the pCIG-mTOR mutant-IRES-EGFP vector to construct a recombinant vector (pCIG-mTOR mutant-IRES-EGFP; mU6-sheIF4E).

In detail, for use in preparing a FCD type II animal model, a recombinant vector was constructed by adding a sheIF4E sequence to the backside sequence of pCIG-mTOR-IRES-EGFP plasmid. shScramble or sheIF4E sequence was obtained with pSicoR vector. pSicoR vector was digested with restriction enzymes HpaI and XhoI. The sequence of shRNA used is as follows. For comparison with shRNA, shScramble was expressed. An RNA transcript from a sense strand is required in order for shRNA to function. Thus, an anti-sense strand is incorporated upon construction of a vector to give double-stranded sequence from which the sense strand is expressed. The sequences are listed in Table 6, below.

The sheIF4E consists of a sense sequence (SEQ ID NO: 203) including CGATTGATCTCTAAGTTTGAT (SEQ ID NO: 202), which binds complementarily with a target region, and an antisense sequence (SEQ ID NO: 204). The shScramble sequence consists of a sense sequence (SEQ ID NO: 206) including GGAATCTCATTCGATGCAT (SEQ ID NO: 205), which binds complementarily to a target region, and an antisense sequence (SEQ ID NO: 207).

TABLE 6

| SEQ ID NO | name | Nucleotide sequence (5'->3') |
|---|---|---|
| 202 | SheIF4E | CGATTGATCTCTAAGTTTGAT |
| 203 | sheIF4E sense strand | T-CGATTGATCTCTAAGTTTGAT-TTCAAGAGA-ATCAAACTTAGAGATCAATCG-TTTTTTCTCGA |
| 204 | sheIF4E anti-sense strand | TCGAGAAAAAA-CGATTGATCTCTAAGTTTGAT-TCTCTTGAA-ATCAAACTTAGAGATCAATCG-A |
| 205 | shScramble | GGAATCTCATTCGATGCAT |

TABLE 6 -continued

| SEQ ID NO | name | Nucleotide sequence (5'->3') |
|---|---|---|
| 206 | shScramble sense strand | T-GGAATCTCATTCGATGCAT-TTCAAGAGA-ATGCATCGAATGAGATTCC-TTTTTTCTCGA |
| 207 | shScramble anti-sense strand | TCGAGAAAAAA-GGAATCTCATTCGATGCAT-TCTCTTGAA-ATGCATCGAATGAGATTCC-A |

The pSicoR vector digested with HpaI and XhoI restriction enzymes was ligated with the shScramble or the sheIF4E sequence in the presence of ligase to construct pSicoR-shScramble and pSicoR-sheIF4E vectors, respectively. Neuro2A cells were cultured and transfected with pSicoR to evaluate the translational downregulation of eIF4E in the same manner as in Example 1.2.

From the pSicoR-shScramble vector and the pSicoR-sheIF4E vector, shScramble and sheIF4E were respectively amplified, together with the mU6 promoter, by PCR using the following primers:

```
Forward primer (SEQ ID NO: 208):
ggccgaggcctcctgggcccgctctagagatccgac

Reverse primer (SEQ ID NO: 209):
cgagtactaggatccattaggcgg
```

The PCR products (shScramble and sheIF4E sequences), each including the mU6 promoter, were digested with SfiI restriction enzyme. pCIG-mTOR mutant-IRES-EGFP vector was cut with PsiI and SfiI restriction enzymes. The digested pCIG-mTOR mutant-IRES- as ligated with the digested shScramble or sheIF4E each including the mU6 promoter, using a ligase. The sheIF4E sequence-added vector pCIG-mTOR mutant-IRES-EGFP; mU6-sheIF4E plasmid was constructed using the method described above.

As will be explained below, FIGS. 9a to 9f provide data showing that the eIF4E-downregulated animal model established using sheIF4E according to Example 2 can be prevented from being affected by epilepsy.

2-2: Efficient Knockdown of eIF4E and Effect of In-Vivo Knockdown of eIF4E on Expression of ADK, IRSp53, and CREB1

For the animal model, prepared in Example 2-1, in which eIF4E was knock-downed using sheIF4E, after embryos that had been electroporated with a plasmid carrying an mTOR mutant gene at embryonic day 14 (E14), in the same manner as in U.S. Pat. No. 9,629,346, were born, the mice expressing fluorescence were screened by flashlight (Electron Microscopy Science, USA).

In this regard, immunofluorescence staining for eIF4E was performed on the mice, showing a reduced expression level of eIF4E and demonstrating the function of the model (FIGS. 9a to 9d).

In detail, efficient knockdown of eIF4E by sheIF4E was validated by Western blot analysis in substantially the same manner as in Example 1 (FIGS. 9a and 9b). Construction of pCIG-MTOR mutant-IRES-GFP; mU6-shScramble or pCIG-MTOR mutant-IRES-GFP; mU6-sheIF4E vector and the inhibitory activity of sheIF4E against eIF4E were identified by western blot analysis using cell lysates.

Figure 9C:
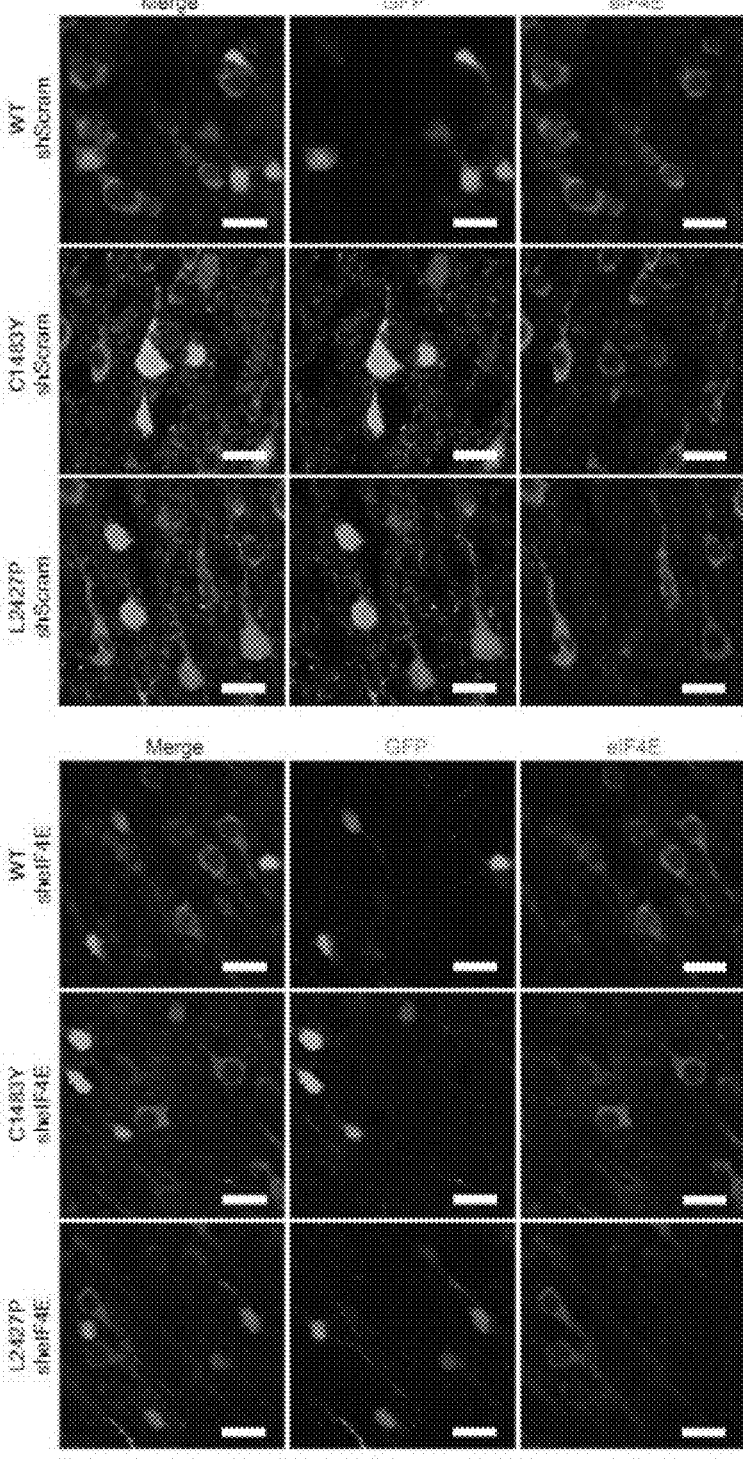
Figure 9D:
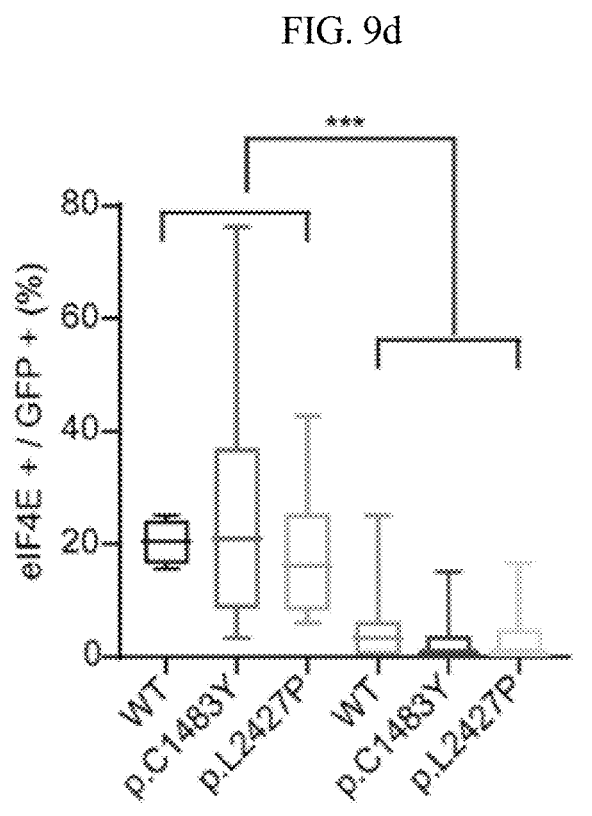

Immunostaining for eIF4E was performed in substantially the same manner as in Example 1 on the mice, showing that eIF4E expression was significantly reduced in sheIF4E-expressing neurons (FIGS. 9c and 9d). From the animal models established using pCIG-MTOR mutant-IRES-GFP; mU6-sheIF4E vector in the same manner as in Examples 1-6 and 2-1, the brain tissues at postnatal day 21 exhibited reduced expression levels of eIF4E.

Figure 9E:
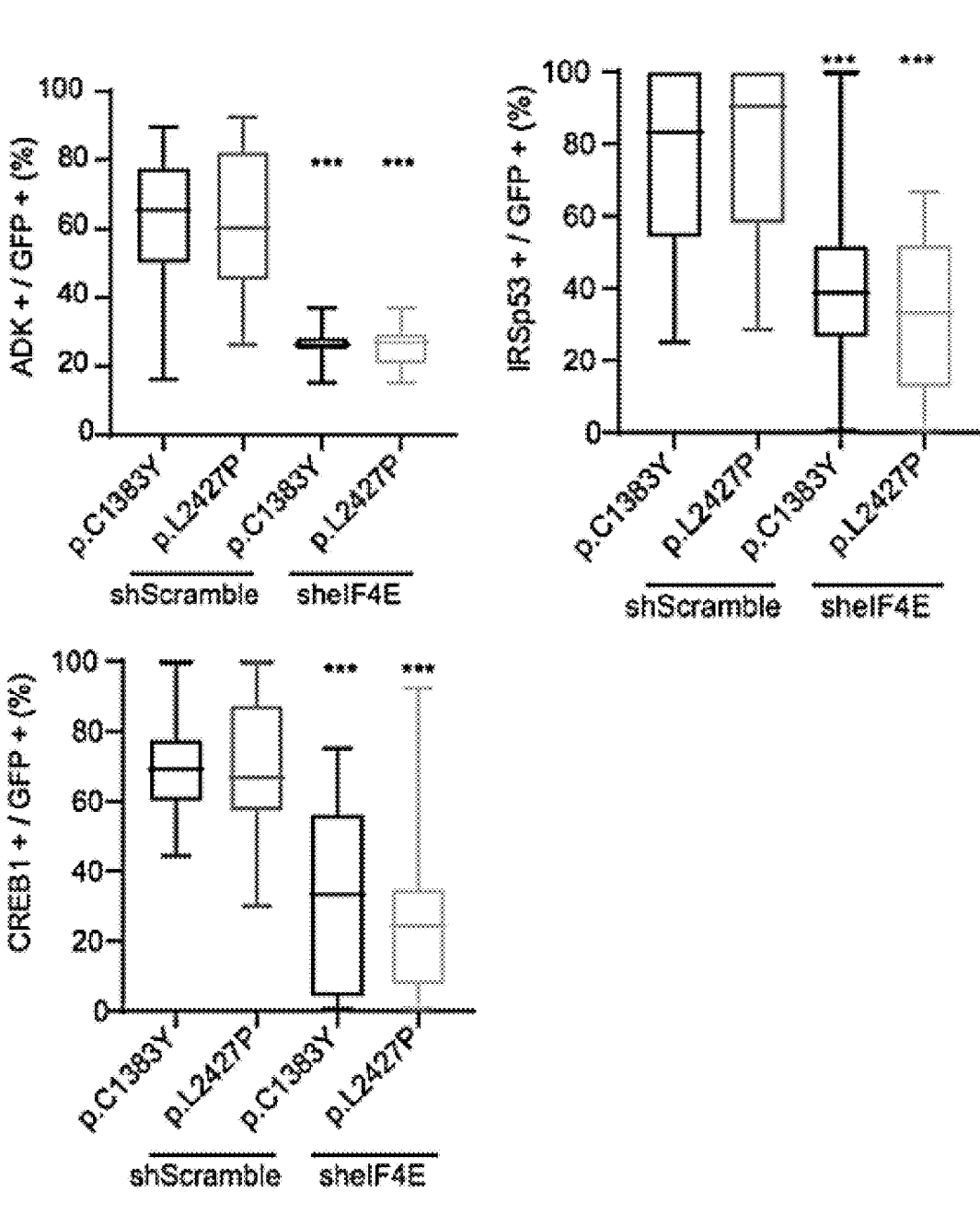
FIG. 9*e* shows decreased expression of ADK, IRSp53, and CREB1 in the brain tissues at postnatal day 21 from animal models established in Examples 1-6 and 2-1 using pCIG-MTOR mutant-IRES-GFP; mU6-sheIF4E vector of Example 2-1, with the decrease of eIF4E expression therein.

Therefore, the present inventors performed additional immunostaining in order to investigate in vivo knockdown effect on the expression of ADK, IRSp53, and CREB1 in the FMCD mice, and confirmed significant reduced expression of the genes (FIG. 9e). In the brain tissues at postnatal day 21 from the animal models established using pCIG-MTOR mutant-IRES-GFP; mU6-sheIF4E vector in the same manner as in Examples 1-3 and 3-1, the expression of ADK, IRSp53, and CREB1 was decreased with decreasing of eIF4E expression. The eIF4E knockdown by sheIF4E significantly reduced the expression of the eIF4E sensitive genes ADK, IRSp53, and CREB1 in both mTOR p.Cys1483Tyr and p.Leu2427Pro mice, compared to shScramble mice, as analyzed by immunohistochemistry.

2-3: Incidence of Epilepsy Onset in Animal Model Expressing shScramble

In FMCD animal models, the onset of epilepsy starts at postnatal day 21 on average and has been completed within postnatal day 50. Video EGG monitoring was conducted from 3 weeks after birth. EGG signals were recorded for 12 hours per day three times in a week from postnatal day 21 to postnatal day 120. From the 12-hour video recordings, the number and length of seizures were measured.

Figure 9F:
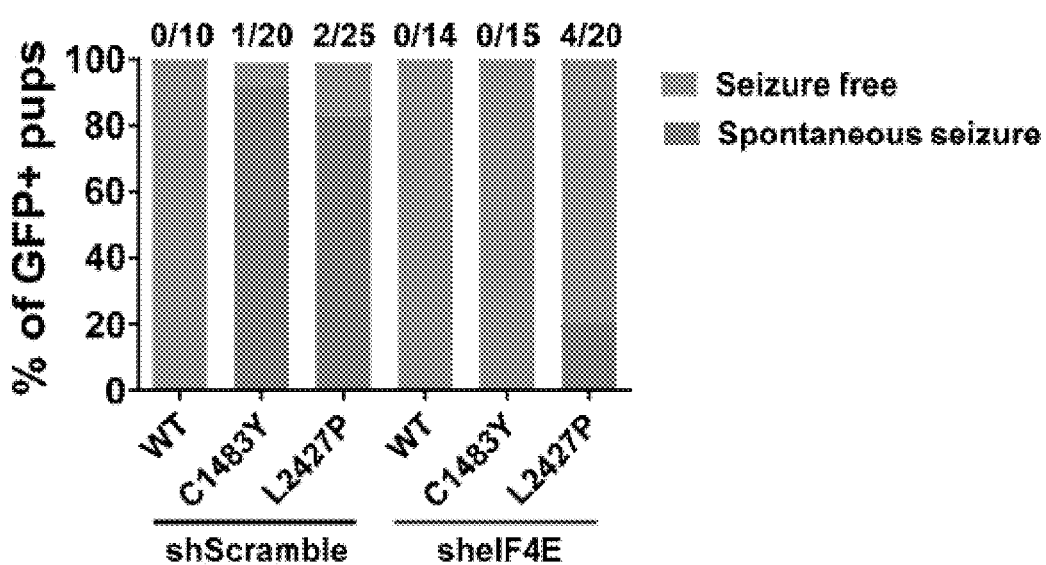
FIG. 9*f* shows remarkable epilepsy reduction in animal models established using the CIG-MTOR mutant-IRES-GFP; mU6-sheIF4E vector and animal models having sheIF4E-mediated downregulation of eIF4E expression in Example 2.

For this experiment, the animal models expressing shScramble, established in Example 2-1, were used. Seizure was detected in 19 of 20 models having mTOR p.C1483Y mutation and in 23 of 25 models having mTOR p.L2427P mutation. Seizure was observed from the 12-hours video recordings taken from postnatal day 21 to postnatal day 120 (FIG. 9f).

2-4: Prevention of Epilepsy Incidence in Animal Model with sheIF4E-Mediated Knockdown Against eIF4E Therein (Seizure Measurement)

The eIF4E-downregulated animal models established in Example 2-1 were video recorded for 12 hours a day three times in a week from postnatal day 21 to postnatal day 120, using a lifecam. From the 12-hours video recordings, the number and length of seizures were measured (FIG. 10).

Figure 10:
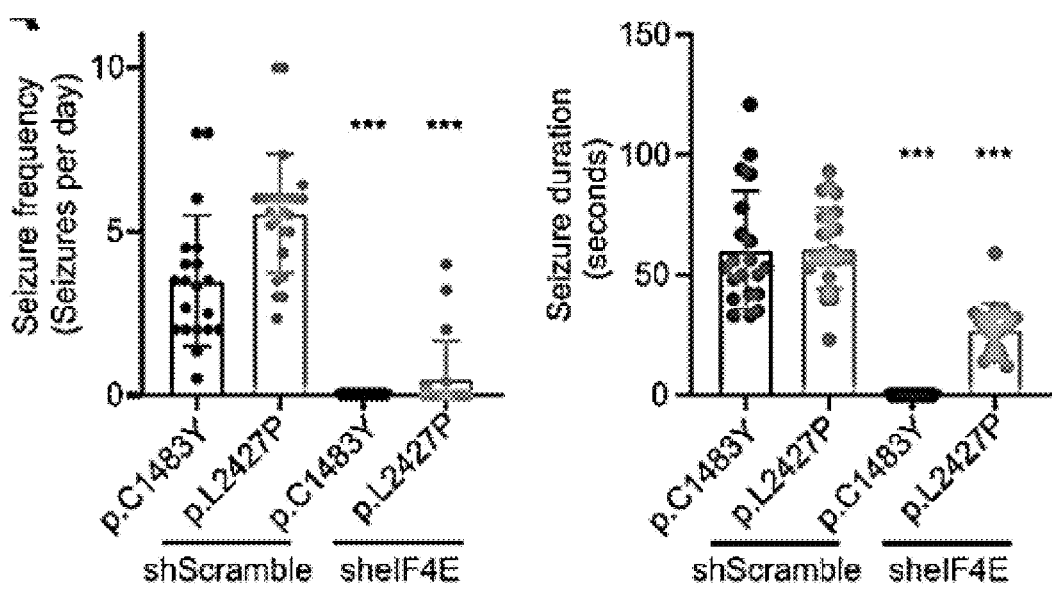
FIG. 10 shows seizure frequency and duration upon onset of seizures in animal models having eIF4E expression downregulated therein according to Example 2.

From the video recordings taken until postnatal day 120 for animal models with sheIF4E-mediated knockdown of eIF4E, as shown in FIG. 10, seizure was observed in none of 15 animals of mTOR p.C1483Y mutation and only in five of 20 animals of mTOR p.L2427P mutation. Thus, the animal models with sheIF4E-mediated downregulation of eIF4E were prevented from being affected with epilepsy. In consideration of the fact that epilepsy in FMCD mouse models generally starts within postnatal day 21 to postnatal day 56, the absence of epilepsy onset until postnatal day 120 verified the prevention of incidence of epilepsy.

Although epilepsy was generated, the frequency and time of seizure were remarkably decreased. In the FMCD animal models, intractable epilepsy significantly decreased in seizure frequency and time when eIF4E-targeting shRNA was expressed to reduce the expression of eIF4E in mTOR mutant-expressing cells. In the FMCD epilepsy animal models, intractable epilepsy significantly decreased in seizure frequency and time when eIF4E-targeting shRNA was expressed to reduce the expression of eIF4E in mTOR mutant-expressing cells.

2-5: Analysis for Cortical Dysplasia, Neuron Size, and Synaptic Spine Density in Animal Model with sheIF4E-Mediated Downregulation of eIF4E Animal models generated with pCIG-mTOR mutant-IRES-EGFP; mU6 sheIF4E vector in Example 2-1 had mTOR mutant-expressing neurons in which the expression of eIF4E protein was downregulated.

Then, mice born following the electroporation of Example 1-6 were analyzed for neuronal cell size and synaptic spine density. Neuronal cell size was measured in ImageJ software (http://rsbweb.nih.gov/ij/). Synaptic spines were counted using a 63× objective lens. Ten basal dendrites were acquired per subject, and measured in electroporated cells expressing a GFP reporter, using manual counting. For neuronal cell size (FIG. 12), mouse brain tissues at postnatal day 21 were acquired and the size of GFP (green)-positive mutant cells (shScramble or sheIF4E expressed) was measured. For synaptic spine density (FIG. 13), mouse brain tissues at postnatal day 21 were acquired and synaptic spines of basal dendrites were counted in GFP (green)-positive mutant cells (shScramble or sheIF4E expressed).

In addition, for cortical dysplasia (FIG. 11), mouse brain tissues at postnatal day 7 of Example 2-1 were acquired and distributions of GFP (green)-positive mutant cells (shScramble or sheIF4E expressed) in the cortex were detected (n=5 in each case. Scale bar=100 µm. Mean±SEM). As shown in FIGS. 9a and 9b, cortical dysplasia was remarkably reduced in the FMCD epilepsy animal models when eIF4E-targeting shRNA was expressed to reduce the expression of eIF4E in mTOR mutant-expression cells.

Therefore, it was observed that the expression downregulation of eIF4E could reduce cortical dysplasia caused by the mTOR pathway activating mutation found in intractable epilepsy patients and the expression regulation of eIF4E could be a therapeutic target for cortical dysplasia.

2-6: Effect of In Vivo Knockdown of eIF4E

This experiment was conducted to examine whether the sheIF4E-mediated in-vivo knockdown of eIF4E in Example 2-1 could alleviate the major phenotypes of FMCD. sheIF4E-mediated eIF4E knockdown was found to successfully rescue all of the pathological phenotypes in both mTOR p.Cys1483Tyr and p.Leu2427Pro mice, compared to the shScramble mice (FIGS. 10, 11, 12, and 13).

Figure 11:
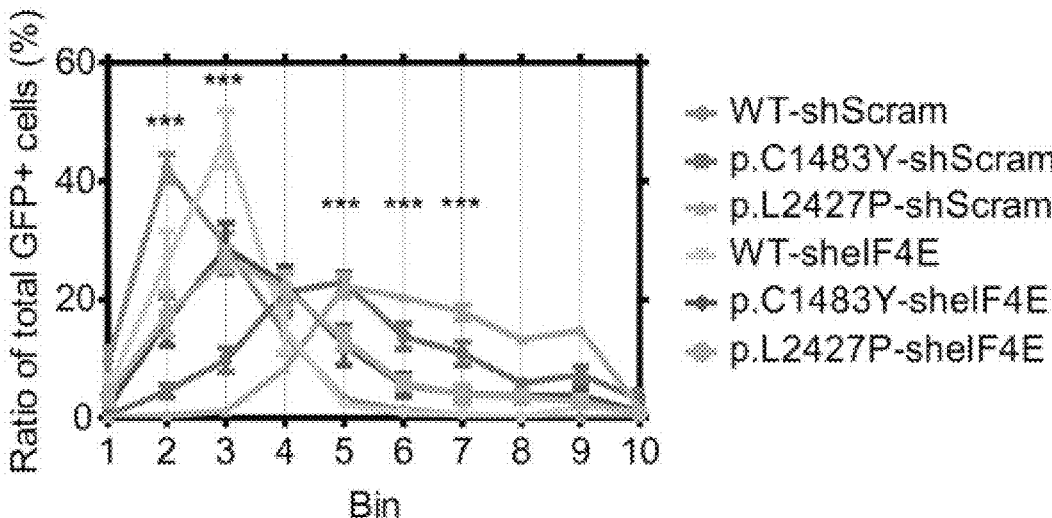
FIG. 11 shows a remarkable decrease in cortical dysplasia in the FMCD epilepsy animal model in which eIF4E expression is reduced by shRNA targeting eIF4E according to Example 2 (*** P<0.001 (n=5 in each case, one-way ANOVA with Bonferroni post-hoc test). Scale bar=100 um. Mean±s.e.m.)
Figure 12:
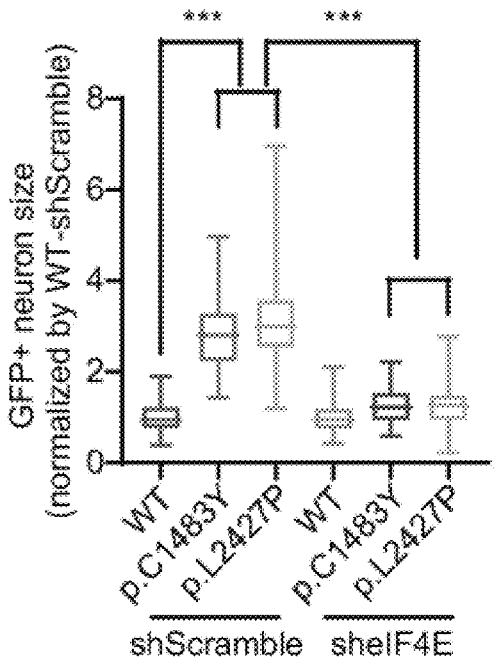
FIG. 12 shows a remarkable decrease in hypertrophic soma size by mTOR mutation when eIF4E expression is downregulated by shRNA targeting eIF4E in mTOR mutant-expressing cells of the FMCD epilepsy animal models of Example 2, wherein comparison is made of therapeutic effects in terms of sizes of cells from layers 2/3 in the cerebral cortex of the FMCD epilepsy animal models at postnatal day 21.
Figure 13:
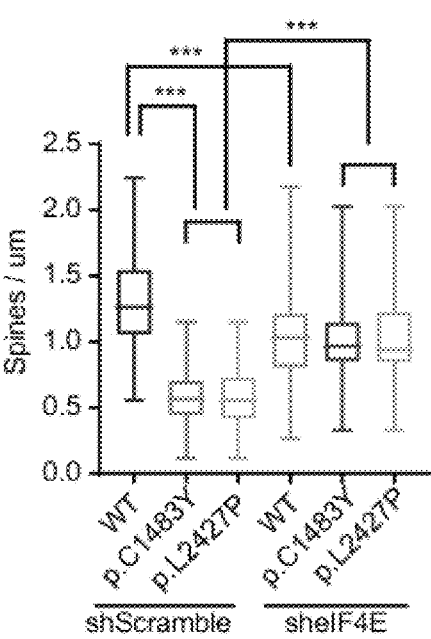
FIG. 13 shows therapy for epilepsy in terms of synaptic spine density in animal models according to Example 2. In the FMCD epilepsy animal models at postnatal day 21, mTOR mutation-mediated reduction of synaptic spine density was reverted in the mTOR mutant-expressing cells when eIF4E expression is downregulated by shRNA targeting eIF4E. *** P<0.001 (n=10 branches, 5 mice per condition, one-way ANOVA with Bonferroni post-hoc test). Scale bar=2 urn. Mean±s.e.m.).

In detail, it was found that eIF4E knockdown almost completely rescued spontaneous seizures observed in the FMCD epilepsy mice (FIG. 10). In addition, eIF4E knockdown rescued hypertrophic soma and decreased spine density, which are representative morphologies of dysmorphic neurons found in FMCD (FIGS. 12 and 13). Moreover, eIF4E knockdown significantly alleviated defective neuronal migration in mTOR mutant mice (FIG. 11).

2-7: Rescuing Effect of sheIF4E-Mediated In-Vivo Knockdown of eIF4E

In the FMCD animal models established with the pCIG-mTOR mutant-IRES-EGFP; mU6 sheIF4E vector of Example 2-1, neuronal cells exhibited a downregulated expression level of eIF4E protein. In order to examine whether sheIF4E-mediated in-vivo knockdown of eIF4E led to the expression downregulation of eIF4E-sensitive genes, expression of eIF4E-sensitive genes was analyzed by immunofluorescence. The immunofluorescence results are depicted in FIG. 9e. The animal models with the sheIF4E-mediated eIF4E knockdown characteristic and the shScramble mice were substantially the same as in Example 2-1.

As shown in FIG. 9e, sheIF4E-mediated eIF4E knockdown significantly reduced the expression of the eIF4E-sensitive genes ADK, IRSp53, and CREB1 in both mTOR p.Cys1483Tyr and p.Leu2427Pro mice, compared to the shScramble mice, as analyzed by immunohistochemical staining.

<Example 3> Treatment of Epilepsy with Drug in Animal Model (Pharmacological Inhibition of eIF4E)

Figure 14:
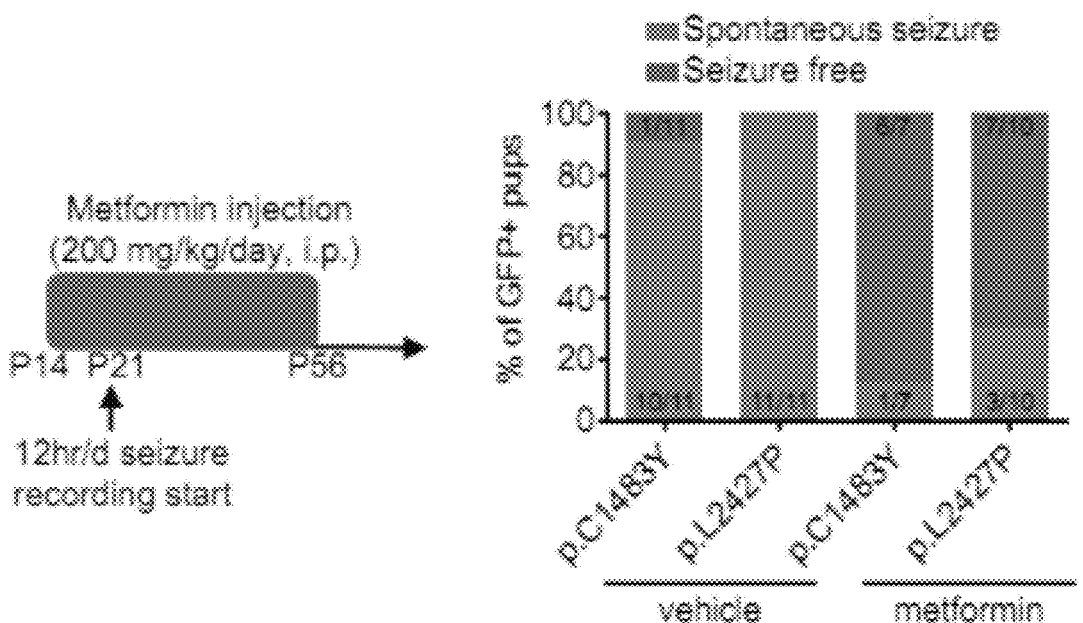
FIGS. 14 and 15 show metformin-mediated reduction of seizure frequency and duration in the epilepsy animal models suffering from epilepsy among those in which eIF4E activity is reduced by metformin according to Example 3 ( P<0.01 and * P<0.001 (p.C1483Y-shScramble: n=20, p.L2427P-shScramble: n=25, p.C1483Y-sheIF4E: n=15, p.L2427P-sheIF4E: n=20, 10 mice for condition in FIG. 14, 5 mice for condition in FIG. 15, one-way ANOVA with Bonferroni post-hoc test). Mean±s.e.m).
Figure 15:
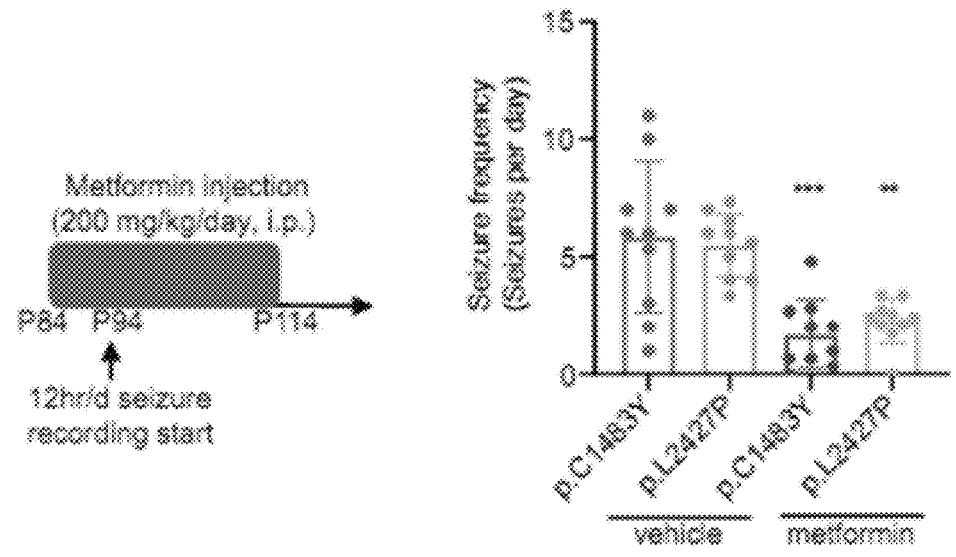

In this experiment, metformin was intraperitoneally injected at a dose of 200 m/kg into the FMCD animal models of Example 1 from P14 to P56 for early treatment and from P84 to P114 for late treatment. Thereafter, 12-hour recording and video-EEG analysis demonstrated that the early treatment with metformin prevented seizure onset and the late treatment suppressed seizure frequency in the FMCD mice (FIGS. 14 and 15).

Accordingly, these results showed that the increased activity of eIF4F leads to the phenotypes of FMCD via the increased translation of the mTOR activation-sensitive genes (e.g., ADK, IRSp53, and CREB1) and that epileptic seizures could be prevented through eIF4E inhibition by metformin.

<Example 4> In Vitro Assay for Efficacy of eIF4E Inhibitor 4-1: ASO Design and Construction ASO sequences that effectuate prophylactic or therapeutic effects on the epilepsy caused by upregulated eIF4E expression, activity, or level were acquired by in-vitro screening. Selection was made of ASO therapeutic sequences highly inhibitory of eIF4E expression.

In this regard, 16- to 20-mer ASO sequences capable binding complementarily to pre-mRNA including the UTR, intron, and exon of human eIF4E gene, using the BLAST program.

Briefly, candidate ASO sequences each had a phosphorothioate bond for every inter-nucleoside bond. For 20-mer ASO, each of the nucleotides at positions 1 to 5 and 16 to 20 in the 5' to 3' translation direction had the 2'-O-(2-methoxyethyl) sugar while the nucleotides at positions 6 to 15 were each modified into 2'-deoxynucleotide, with 5-methylcytosine being employed instead of all cytosine residues. The 16-mer ASO was substantially the same as the 20-mer ASO, with the exception that nucleotides at positions 1 to 3 and 14 to 16 in the 5' to 3' direction had 2'-O-(2-methoxyethyl) sugar. In addition, the phosphodiester linkage was chemically modified into a phosphothioester bond.

4-2: ASO Screening by Western Blot Analysis

The designed eIF4E inhibiting ASO was constructed by Integrated DNA Technologies (IDT) and purified through HPLC and Na+ exchange purification.

Figure 16A:
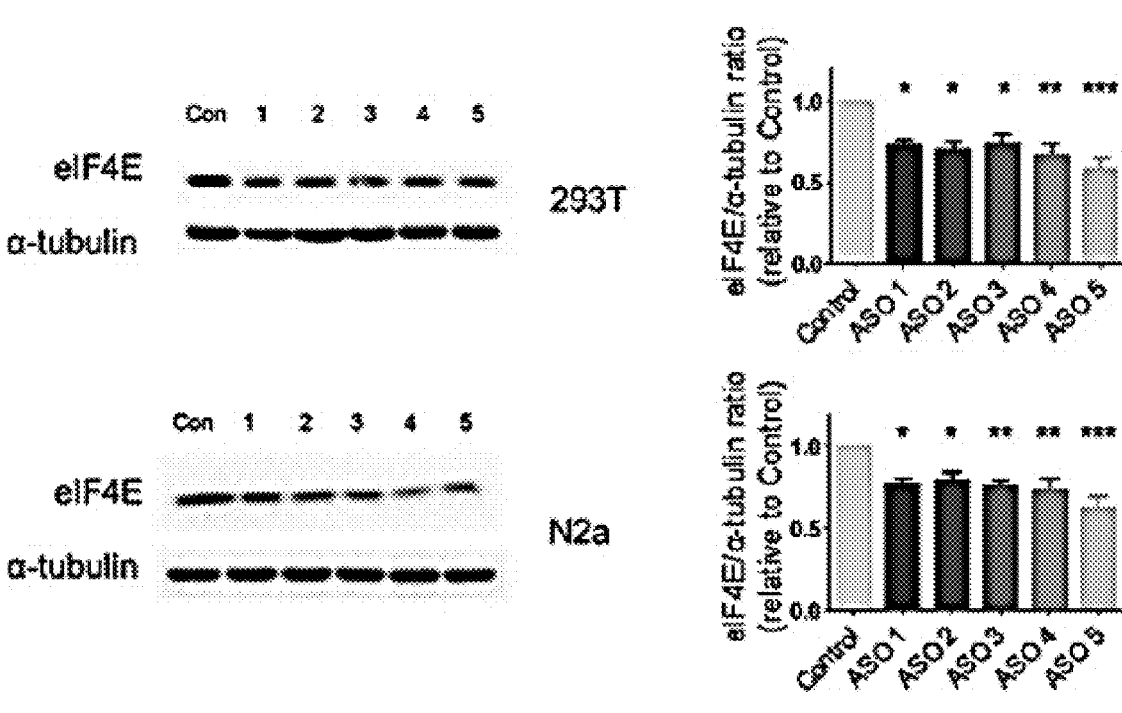
FIG. 16*a* shows ASO-mediated expression downregulation of eIF4E in cells treated with ASO candidates according to an embodiment of the present disclosure, as analyzed by western blotting.
Figure 16B:
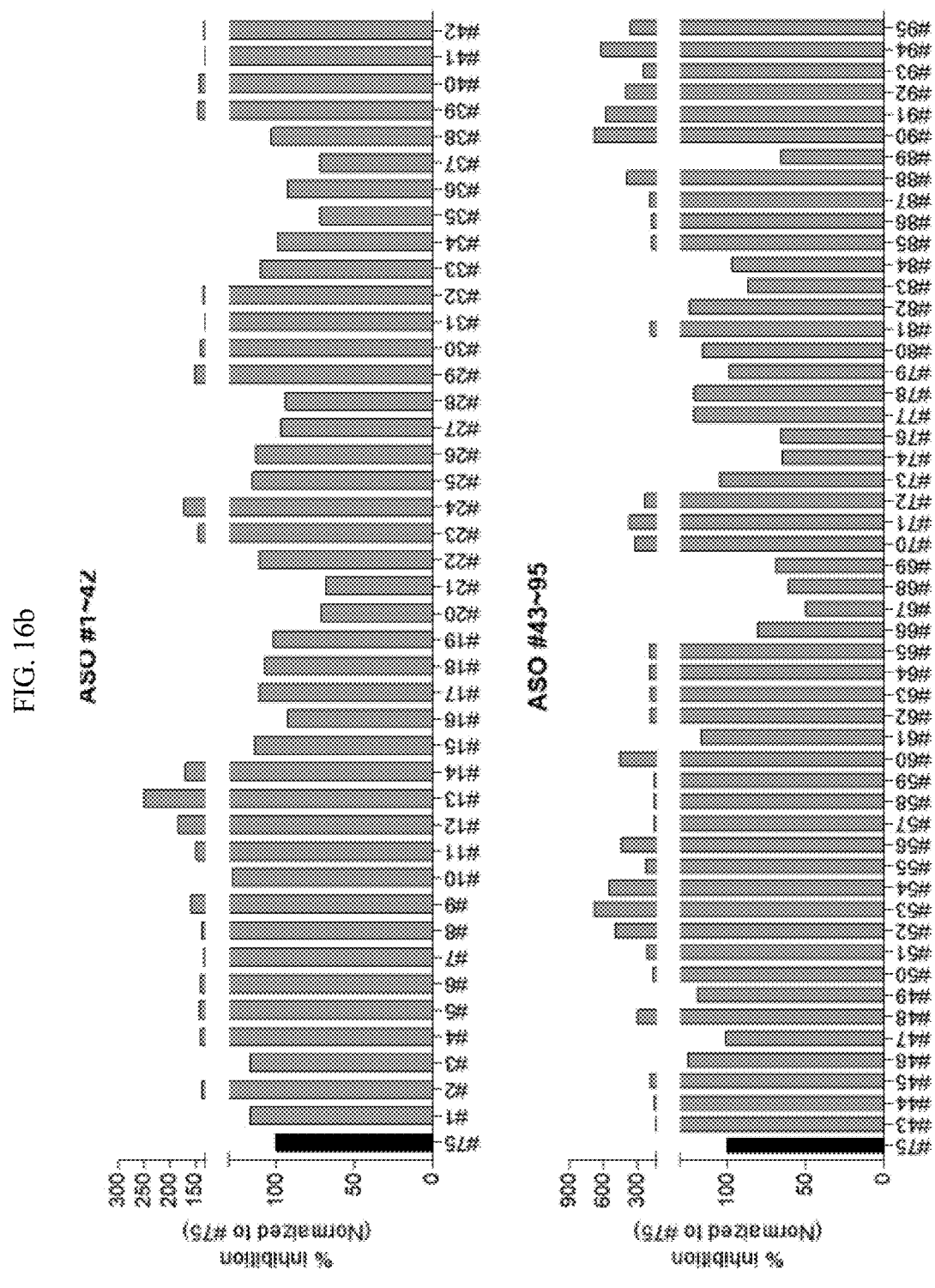
FIGS. 16*b* and 16*c* are graphs in which relative eIF4E mRNA expression levels are quantitatively expressed in cells treated with MO candidates according to an embodiment.
Figure 16C:
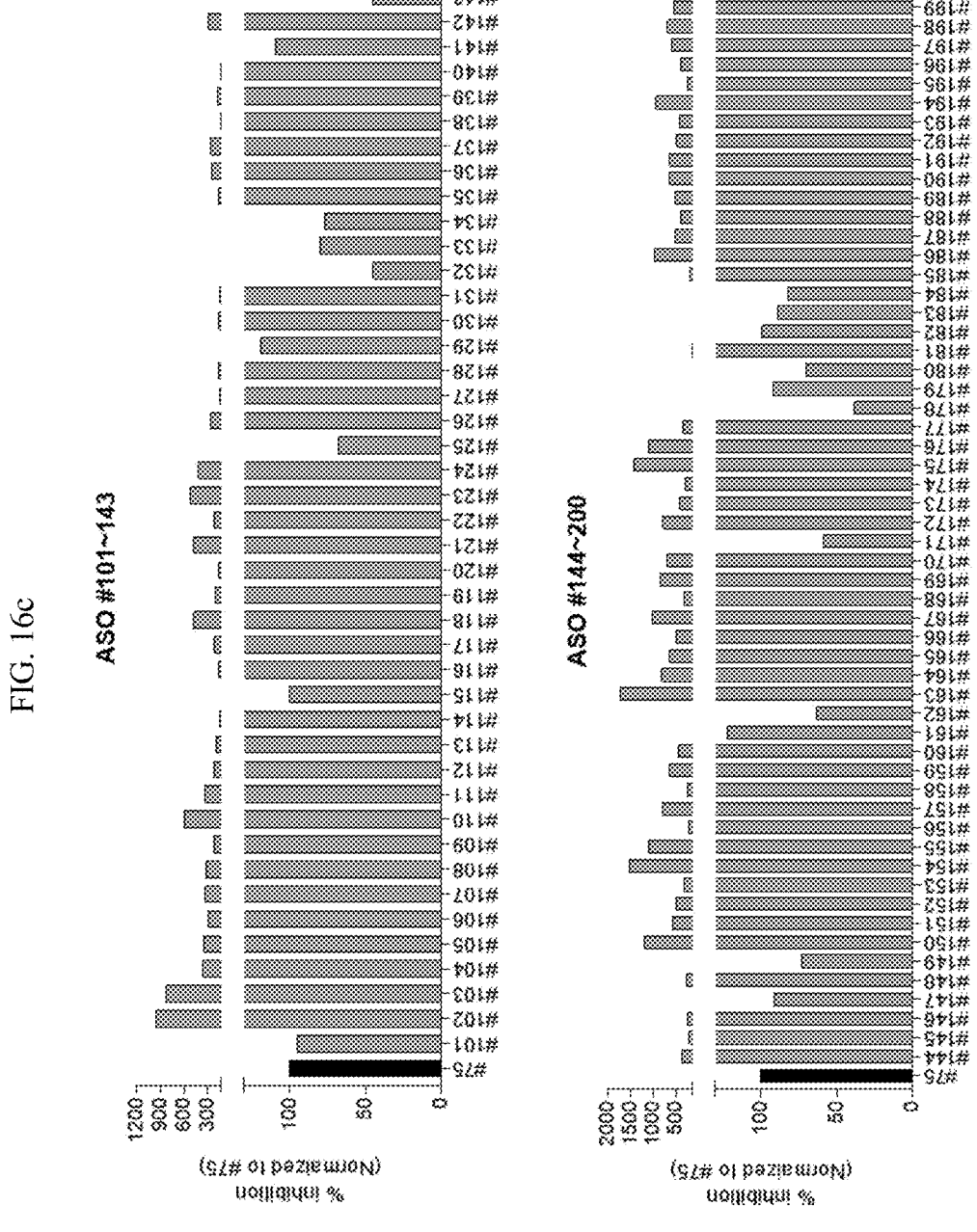

For ASO screening, first, MO candidates were transfected into the human cell lines HEK293T (Human) or the mouse cell line Neuro2A (mouse) with the aid of Lipofectamine 2000. The cells were harvested 72 hours after ASO transfection and then lysed to extract proteins which were analyzed for eIF4E expression by western blotting. Efficient ASO sequences that regulate eIF4E were identified by in-vitro screening. eIF4E protein expression levels in each cell line were normalized to α-tubulin and quantified relative to the control (scrambled ASO-1: CTCAGTAACAGTGACACCAG (SEQ ID NO: 201). Expression levels of eIF4E relative to the control are depicted (FIG. 16a). In FIGS. 16a, 16b, and 16c, the scrambled ASO was employed as the control.

For the western blots of FIG. 16a, ASO candidates with p-value less than 0.05 in One ANOVA test were determined as eIF4E inhibitors having therapeutic activity for epilepsy. Compared to the control, ASO #75 to #79 corresponding respectively to the nucleotide sequences of SEQ ID NO: 75 to 79 were all proven to reduce the expression level of eIF4E in both HEK293T and Neuro2A cells, with statistical significance.

4-3: ASO Screening by Real-Time PCR

In Example 4-2, proteins extracted from cells were analyzed for eIF4E expression by western blotting to screen ASO that regulates eIF4E expression. In this Example, RNA was extracted from cells and analyzed for eIF4E mRNA transcription by real-time PCR so as to screen ASO that regulates eIF4E expression.

In an alternative approach for screening the designed ASO candidates, the human cell line HEK293T cells (human) were cultured on 96-well culture plates for 24 hours and then transfected with ASO candidates with the aid of iN-fect™ transfection reagent (INTRON, 15081). Twenty four hours after transfection, the cells were harvested and subjected to lysis and RNA extraction using SuperPrep™ II Cell Lysis & RT Kit reagent (Toyobo, SCQ-401). From the RNA thus obtained, cDNA was synthesized by reverse transcription PCR. Real-time PCR was performed in CXF384 Touch™ Real-Time System (Bio-Rad) with SYBR® green real-time PCR master mix (Toyobo, QPK-201). Forward and reverse PCR primer sequences for eIF4E and GAPDH are as follows:

```
EIF4E forward primer (SEQ ID NO: 210):
TGGCGACTGTCGAACCG

EIF4E reverse primer (SEQ ID NO: 211):
AGATTCCGTTTTCTCCTCTTCTGTAG

GAPDH forward primer (SEQ ID NO: 212):
GAAGGTGAAGGTCGGAGTCAACG

GAPDH forward primer (SEQ ID NO: 213):
GAAGATGGTGATGGGATTTCC
```

The real-time PCR conditions in the CXF384_Touch™ Real-Time System were as follows: 95° C. for 1 min, then 95° C. for 15 sec, 59.5° C. for 20 sec, and 72° C. for 30 sec for 39 cycles. Each sample was analyzed in triplicates. Relative mRNA expression was normalized to the expression level using GAPDH as an internal control and was evaluated using the 2-44Cq method. eIF4E expression levels are expressed as relative ratios compared with the control scrambled ASO-1 (CTCAGTAACAGTGACACCAG: (SEQ ID NO: 201)) in FIGS. 16b and 16c. FIGS. 16b and 16c are graphs in which relative eIF4E expression levels are quantitatively expressed as ratios compared to the GAPDH expression level in HEK293T cells treated with ASO candidates.

Through the screening method, ASO sequences that exhibited high inhibitory activity against eIF4E expression, compared to the control scrambled ASO-1 (CTCAGTAACAGTGACACCAG; SEQ ID NO: 201), were selected. The selected ASO sequences are given in Table 2.

4-4: Secondary Selection of ASO

From the primarily selected ASO as eIF4E inhibitors in Table 2, selection was made of ASO that reduced eIF4E expression to the degree as great as or greater than that of SEQ ID NO: 75 (ASO-1), for example, ASO that allowed eIF4E mRNA expression in a quantitatively predetermined range relative to the eIF4E expression level of ASO #75

(ASO-1), (e.g., eIF4E mRNA expression level of 125% or less, 120% or less, 115% or less, 110% or less, or 100% or less relative to that of ASO #75). Moreover, more preferable ASO was selected on the basis of additional criteria such as off-target and/or mismatch base pairing, and the results are given in Table 7, below.

In Table 7, the number of off-target genes was the number of target genes other than eIF4E, which are coincident except for differing by 1, 2, or 3 nucleotides on the corresponding ASO sequences when an in-silico method was performed on each of the selected ASO sequences; and the eIF4E expression represents the mRNA expression level measured by real-time PCR in the same manner as in Example 4-3 as % inhibition of each ASO relative to ASO #75.

TABLE 7

| SEQ | Number of gene in the Off target | | | Expression level of eIF4E(%) |
|---|---|---|---|---|
| ID No | 1 bp | 2 bp | 3 bp | compared to ASO#75 |
| #16 | 0 | 2 | 59 | 93% |
| #20 | 0 | 5 | 70 | 71% |
| #21 | 0 | 6 | 78 | 68% |
| #27 | 0 | 1 | 64 | 97% |
| #28 | 2 | 9 | 132 | 94% |
| #35 | 0 | 1 | 18 | 72% |
| #75 | 0 | 4 | 67 | 100% |
| #77 | 0 | 2 | 48 | 121% |
| #89 | 4 | N/D | N/D | 65% |
| #132 | 2 | 14 | 5 | 45% |
| #143 | 0 | 3 | 27 | 45% |
| #147 | 0 | 5 | 18 | 91% |
| #149 | 0 | 3 | 29 | 73% |
| #161 | 2 | 5 | 24 | 122% |
| #162 | 2 | 4 | 25 | 63% |
| #171 | 0 | 8 | 25 | 59% |
| #178 | 0 | 7 | 40 | 38% |
| #179 | 0 | 5 | 34 | 92% |
| #180 | 1 | 4 | 31 | 70% |
| #182 | 0 | 0 | 37 | 99% |
| #183 | 0 | 4 | 9 | 89% |
| #184 | 0 | 3 | 27 | 82% |

4-5: Common Motif of ASO Sequences

For the sequences listed in Table 2, Multiple Em for motif elicitation (MEME, http://meme-suite.org/tools/meme) was performed using MEME browser application program (version 5.1.1) to analyze the ASO sequences highly inhibitory of eIF4E expression for common motifs (Bailey T L, Elkan C. Fitting a mixture model by expectation maximization to discover motifs in biopolymers. Proc. Second Int. Conf. Intell. Syst. Mol. Biol. 1994; 28-36).

Through the multiple Em for motif elicitation (MEME) analysis for some of the selected ASO sequences in Example 4-4, it was found that a specific common motif was enriched with statistical significance.

Figure 16D:
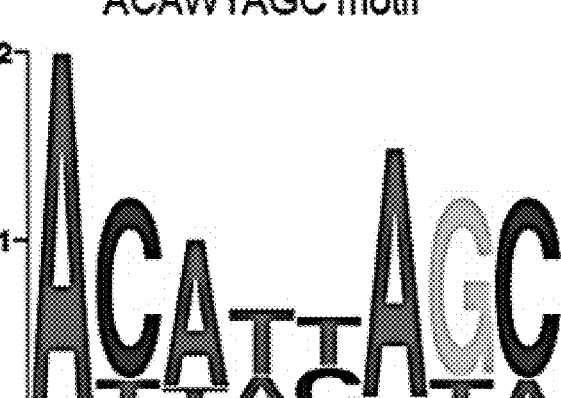
FIG. 16*d* shows a common motif in ASO sequences selected according to an embodiment of the present disclosure.
Figure 16D:

FIG. 16d shows ACAWYAGC (SEQ ID NO: 96) as a common motif located on the ASO sequences including ASO #27, ASO #28, ASO #35, ASO #147, ASO #178, ASO #179, ASO #180, and ASO #182 in Table 2. In FIG. 16d, the occupancy ratios of the four nucleotides A, G, T, and C in the motif are depicted, with a single nucleotide contributing 0 bit to 2 bits of information content. Locations of the common ACAWYAGC motif are expressed as red lines on the 20-mer ASO sequences. In the common motif, Y refers to a pyridine T or C and W refers to A or T.

4-6: Inhibitory Concentration (IC$_{50}$) Against eIF4E mRNA (Real-Time PCR)

The ASO sequences, acquired by the in-vitro screening method, which effectively inhibit eIF4E expression, that is, ASO #21, ASO #27, ASO #35, ASO #75 (ASO-1), ASO #77 (ASO-3), and ASO #182 were analyzed for inhibitory concentration (IC$_{50}$) against eIF4E mRNA expression.

In order to calculate IC$_{50}$ values for ASO sequences, ASO candidates are transfected at different concentrations (20 nM, 80 nM, 320 nM) into the human cell line HEK293T (human) with the aid of iN-fect™ in vitro transfection reagent (15081, iNtRON, Republic of Korea). Twenty four hours after ASO transfection, the cells were harvested and analyzed for eIF4E mRNA expression reduction by real-time PCR. Relative eIF4E mRNA expression was normalized to the expression level using GAPDH as an internal control and was evaluated using the $2^{-\Delta\Delta Cq}$ method.

Figure 16E:
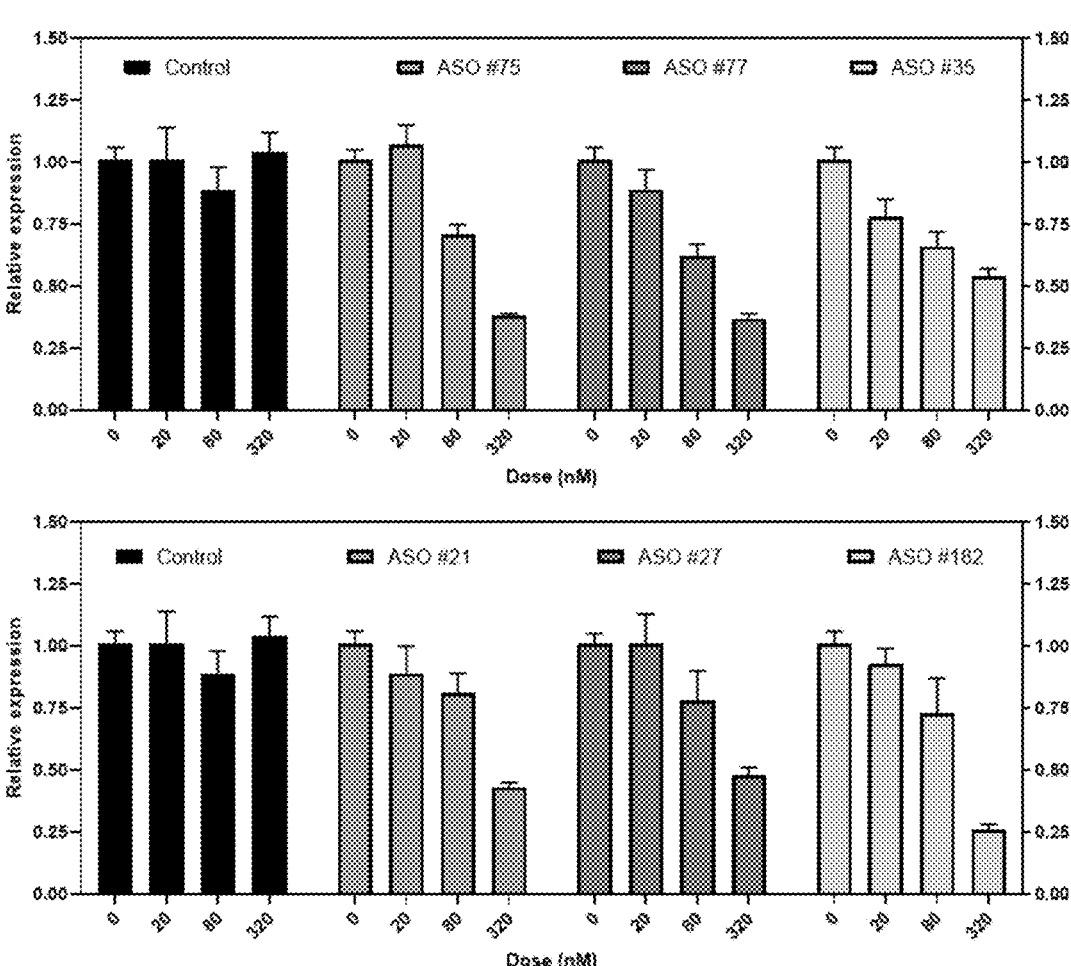
FIG. 16*e* shows mRNA expression levels and $IC_{50}$ values of ASO sequences selected according to an embodiment of the present disclosure.

As an analysis result for the HEK293T cells, eIF4E mRNA expression was inhibited by ASO #75, ASO #77, ASO #21, ASO #27, and ASO #35 at all of the doses, compared to the mismatch ASO: GATCCTTTGTTAATGT-TACA (SEQ ID NO: 214), which is the same as ASO #77 with the exception that bases CACC at positions 8-9-10-11 was changed to TGTT. For comparison of inhibitory concentrations (IC$_{50}$) among ASO candidates, a dose-response curve was derived by normalized nonlinear regression using Prism8 program (GraphPad Software, USA) (FIG. 16e).

The data of IC$_{50}$ showed that the inhibitory potency against eIF4E mRNA expression in HEK293T cells was decreased in the order of ASO #35 (IC$_{50}$=22.77 nM), ASO #77 (IC$_{50}$=53.82 nM), ASO #21 (IC$_{50=86.69}$ nM), ASO #182 (IC$_{50=91.07}$ nM), ASO #27 (IC$_{50=92.45}$ nM), and ASO #75 (IC$_{50}$=93.93 nM).

4-7: Expression Level of Off-Target Gene

This experiment was conducted to examine whether ASO #35 and ASO #75 in Table 2 had inhibitory activity against the expression of off-target genes.

In Silico analysis identified the following off-target genes: one off-target gene (ERBB4) with two nucleotide mismatches with ASO #35; and four off-target genes (TNFAIP8L3, STK32A, TTPA, TTC28) with two nucleotide mismatches with ASO #75. Off-target gene analysis was performed on ERBB4 to ASO #35 and TTC28 (Tetratrico-peptide repeat domain 28) to ASO #75.

Briefly, ASO #35 or ASO #1 were transfected at various doses (5 nM, 20 nM, 80 nM, 320 nM, and 1280 nM) into HEK293T cells (human), with the aid of iN-fect™ in vitro transfection reagent (15081, iNtRON, Republic of Korea). Twenty four hours after ASO transfection, the cells were harvested and subjected to lysis and RNA extraction using SuperPrep™ II Cell Lysis & RT Kit reagent (Toyobo, SCQ-401). Then, real-time PCR for ERBB4 and TTC28 mRNA expression was performed in CXF384 Touch™ Real-Time PCR Detection System (Bio-Rad, USA) with SYBR® Green Realtime PCR Master Mix (QPK-201, TOYOBO, Japan). Real-time PCR conditions using CXF384 Touch™ Real-Time PCR Detection System were as follows: 95° C. for 1 min, followed by 40 cycles of 95° C. for 15 sec, 59.5° C. for 20 sec, and 72° C. for 30 sec. Each sample was analyzed in triplicates. Relative mRNA expression of ERBB4 and TTC28 was normalized to the expression level using GAPDH as an internal control and was evaluated using the $2^{-\Delta\Delta Cq}$ method. eIF4E and GAPDH primers for real-time PCR were the same as in Example 4-3. Forward and reverse primers for ERBB4 and TTC28 genes were as follows:

```
ERBB4 forward primer (SEQ ID NO: 215):
CAGTCAGTGTGTGCAGGAAC

ERBB4 reverse primer (SEQ ID NO: 216):
AGCCTGTGACTTCTCGAACA

TTC28 forward primer (SEQ ID NO: 217):
CTCATGGGAATCTGGGCTCT

TTC28 reverse primer (SEQ ID NO: 218):
TGATGAAGCTGCCTCTCGAT
```

Figure 16F:
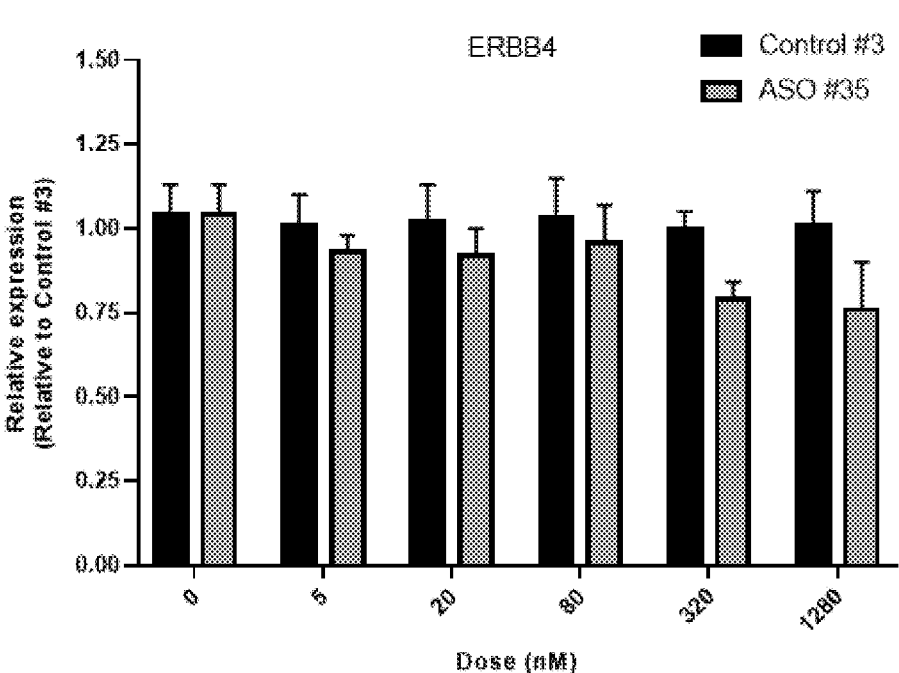
FIGS. 16*f* and 16*g* show off-target expression levels of ASO sequences according to an embodiment of the present disclosure.
Figure 16G:
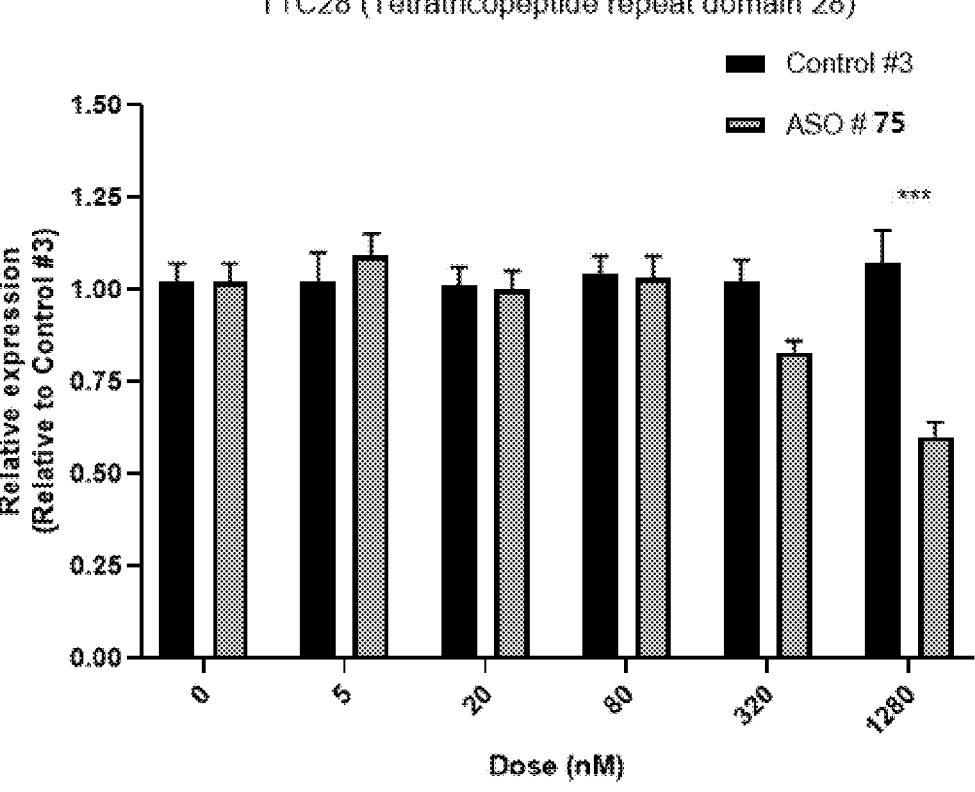

In FIGS. 16f and 16g, relative expression ratios were depicted, compared to Scrambled ASO-2 (TAAGGCTAT-GAAGAGATACG, SEQ ID NO: 219). From two-way ANOVA analysis for the real-time PCR products, it was observed that ASO #35 had no influences on the mRNA expression of the off-target gene ERBB4 whereas when applied at a concentration of 1280 nM, ASO #1 inhibited the expression of the off-target gene TTC28. The dose-response curve derived through normalized nonlinear regression showed that ASO #1 had an $IC_{50}$ of 400.6 nM for the off-target gene TTC28, which is about fivefold higher than the $IC_{50}$ value of 83.72 nM for eIF4E.

4-8: Chemical Modification (cEt/LNA)

ASO with constrained ethyl (cEt) nucleotide modification is generally termed 2.5 ASO. A cEt-modified sugar refers to bicyclic sugar moiety comprising a bridge between 4'-carbon and 2'-carbon (4'-CH(CH_3)—O-2'). In addition, for a chemically modified structure, locked nucleic acid (LNA), which is termed third generation analogue for MO, comprises a ribose having a modified structure locked by an extra bridge between 4' carbon and 2' oxygen in the nucleotide. LNA is known as an RNA analogue enhancing Watson-Crick base pairing intensity.

eIF4E inhibiting ASOs modified to have cEt nucleotides at positions 1-5 and 16-20 and a phosphothioate bond for every internucleoside linkage with respect to ASO sequences #21, #35, and #78 of Example 4-1 were synthesized by Bio-Synthesis. eIF4E inhibiting ASOs modified to have LNA nucleotides at positions 1-5 and 16-20 and a phosphothioate bond for every inter-nucleoside linkage with respect to ASO sequences #77, #27, and #35 were synthesized by IDT. All of the ASOs synthesized were purified by HPLC and Na+ exchange purification. The mismatch control (MM) accounts for the control ASO of GATCCTTTGT-TAATGTTACA (SEQ ID NO: 214) in a 2' MOE gapmer structure having TGT instead of the bases CAC at positions 8-9-10 on the sequence of ASO #77.

Figure 16H:
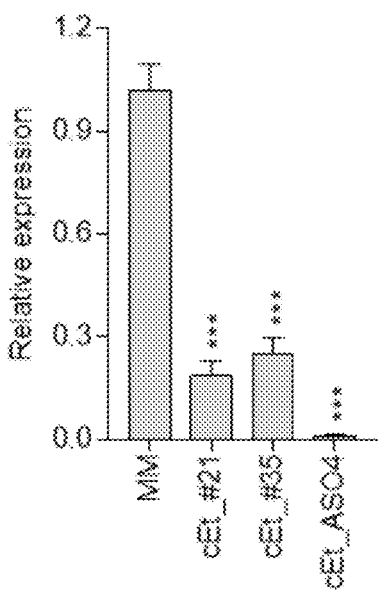
FIG. 16*h* shows inhibitory efficiencies of chemical variants of ASO according to an embodiment of the present disclosure against eIF4E expression.
Figure 16H:
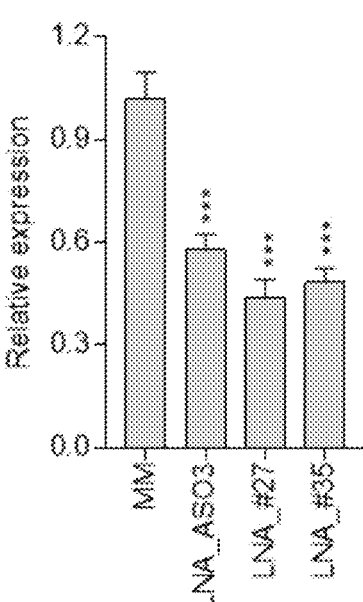

As eIF4E inhibitors, ASOs chemically modified with cEt or LNA were analyzed for inhibitory activity against eIF4E expression. In this regard, ASO candidates were transfected into the human cell line HEK293T (human), using iNfect transfection reagent (iNtRON, 15081). Twenty four hours after transfection, the cells were harvested and analyzed for inhibitory activity against eIF4E expression by real-time PCR Relative expression levels are quantitatively expressed as ratios, compared to the control ASO having 3 nucleotide mismatches with eIF4E (FIG. 16h). For the real-time PCR products, the ASOs showed downregulated expression levels of eIF4E mRNA in HEK293T cells, compared to the control eIF4E mismatch ASO, as analyzed by One ANOVA test, with statistical significance (p-value≤0.05). Mismatch control (MM) was the same as ASO #77 with the exception that TGT is substituted for CAC at positions 8-9-10 in the 5' to 3' direction.

<Example 5> Treatment of FMCD Epilepsy Animal Model with ASO 5-1: Treatment of Epilepsy Through eIF4E Expression Reduction in Animal Model (Seizure Monitoring)

ASO #75 and ASO #77 of Table 2, constructed in Example 4-1, were observed to reduce eIF4E expression in animal models.

For this experiment, animal models established using pCIG-mTOR p.C1483Y-IRES-EGFP and pCIG-mTOR p.L2427P-IRES-EGFP of Example 1 were used while animal models established with pCIG-mTOR (WT)-IRES-EGFP (mTOR p.C1483Y or mTOR p.L2427P) served as a control. The ASOs were each intracerebroventricularly injected (ICV injection) at a dose of 100-500 μg to the brains of the mice that had been identified to undergo epileptic seizure. From day 3 after ASO injection to up to day 70, 12-hour video were recorded for seizure monitoring 2-3 times a week per mouse.

From the experiment result, it was found that the injection of ASO #75 (ASO-1) or ASO #77 (ASO-3) remarkably reduced seizure frequency in the epilepsy models (mTOR p.C1483Y or mTOR p.L2427P)).

Figure 17:
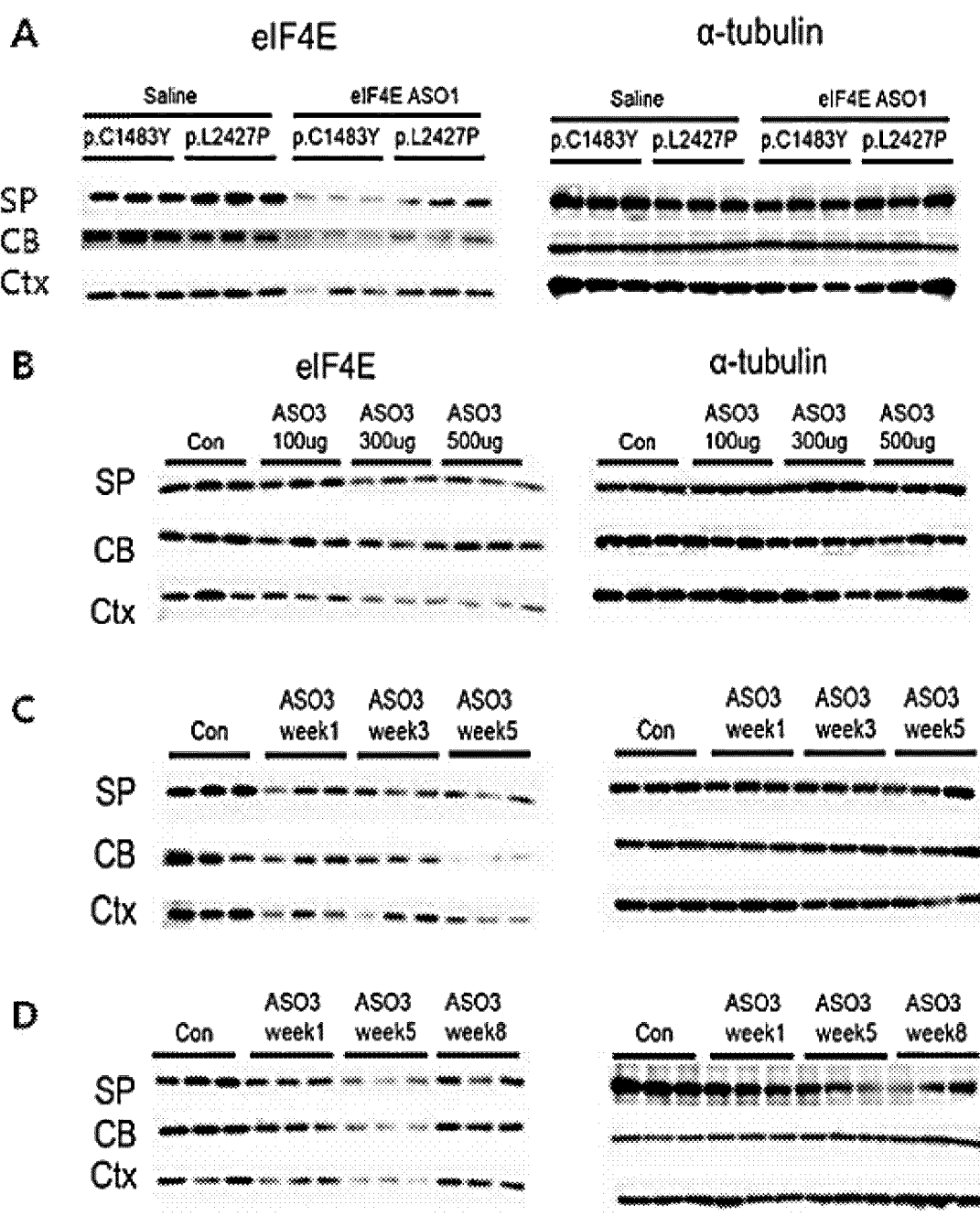
FIGS. 17 to 19 shows that intracerebroventricular injection of the ASO candidates according to an embodiment of the present disclosure to normal mice reduced eIF4E expression in the cerebral cortex, the cerebellum, and the spinal cord and thus lowered seizure frequency, wherein the FMCD animal models of Examples 1-6 decreased in seizure frequency after intracerebroventricular injection of ASO candidates. Each of panels B to D of FIG. 17 and panels E and F of FIG. 18 represents "normal mice", whereas panel A of FIG. 17 and panels G and H of FIG. 18 represents "FMCD animal models."
Figure 18:
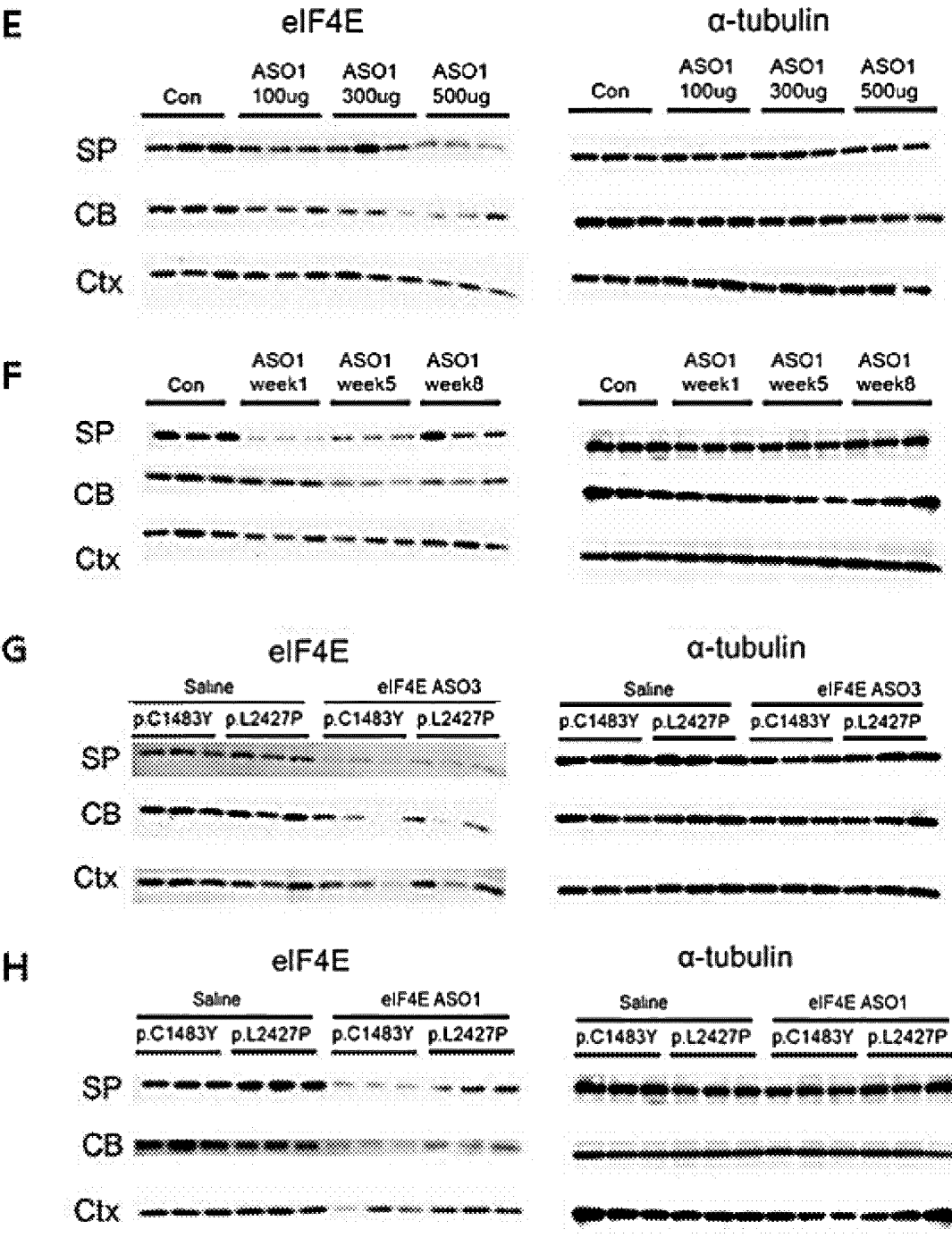
Figure 19:
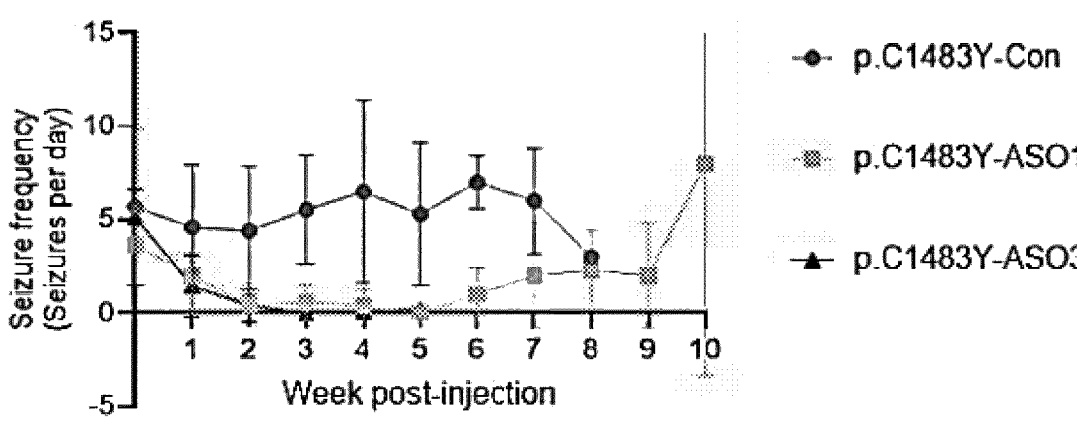
Figure 19:
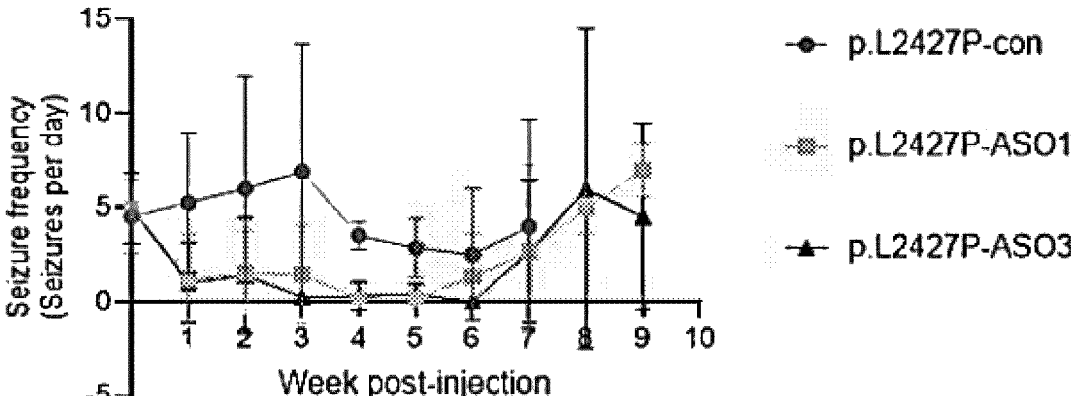

After intraventricular injection of the ASO candidates to the animal models, eIF4E expression was reduced in the cerebral cortex, the cerebellum, and the spinal cord, with the consequent reduction in seizure frequency. FIGS. 17 to 19 shows that intraventricular injection of the ASO candidates to the animal models reduced eIF4E expression in the cerebral cortex, the cerebellum, and the spinal cord and thus lowered seizure frequency. Results are depicted for ASO-1 in panel (A) of FIG. 17 (A) and panels (E), (F) and (G) of FIG. 18, for ASO-3 in panels (B), (C), and (D) of FIG. 17 and panel (H) of FIG. 18 (H), and for ASO #75 (ASO-1) and ASO #77 (ASO-3) in FIG. 19.

5-2: Distribution of ASO in Brain Cells

In order to examine whether brain cells uptook ASO in practice, cy3 (fluorescent dye)-labeled ASO (cy3-ASO) was intracerebroventricularly injected and analyzed for cellular distribution.

Mice (C57BL/6J) (Damul Science) or the animal models established with pCIG-mTOR mutant-IRES-EGFP in Example 1 were anesthetized with isoflurane (0.4 L/min of oxygen and isoflurane vaporizer gauge 2 during surgery operation). Surgical incision was made from the dorsal neck to the glabella. The cranium thus exposed was wiped with a cotton swab.

A steam-sterilized 26G syringe was sterilized three times with 70% ethanol and additionally once with distilled water. The syringe needle was positioned at the site AP −0.3 mm from the bregma and ML +1.0 mm. The syringe needle was inserted DL −3.0 mm from the bregma and positioned at the lateral ventricle. Three minutes after needle positioning, ASO was injected at a rate of 0.5 μl/sec. The syringe was left for 3 min after injection and then removed. A cotton swab was pressed for 1 min against the injected site and the skin was sutured.

Figure 20A:
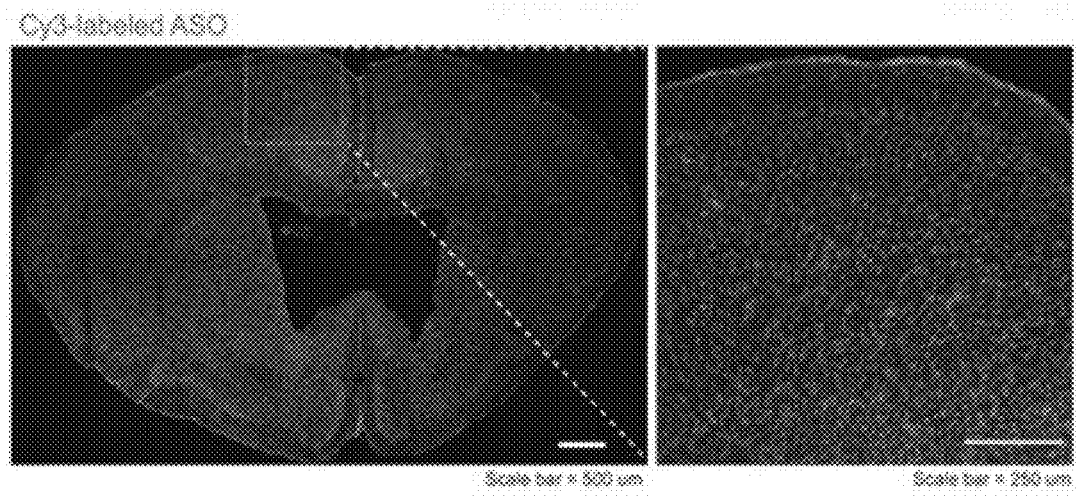
FIGS. 20*a* and 20*b* show distributions of control ASO in brain cells after intracerebroventricular injection.
Figure 20B:
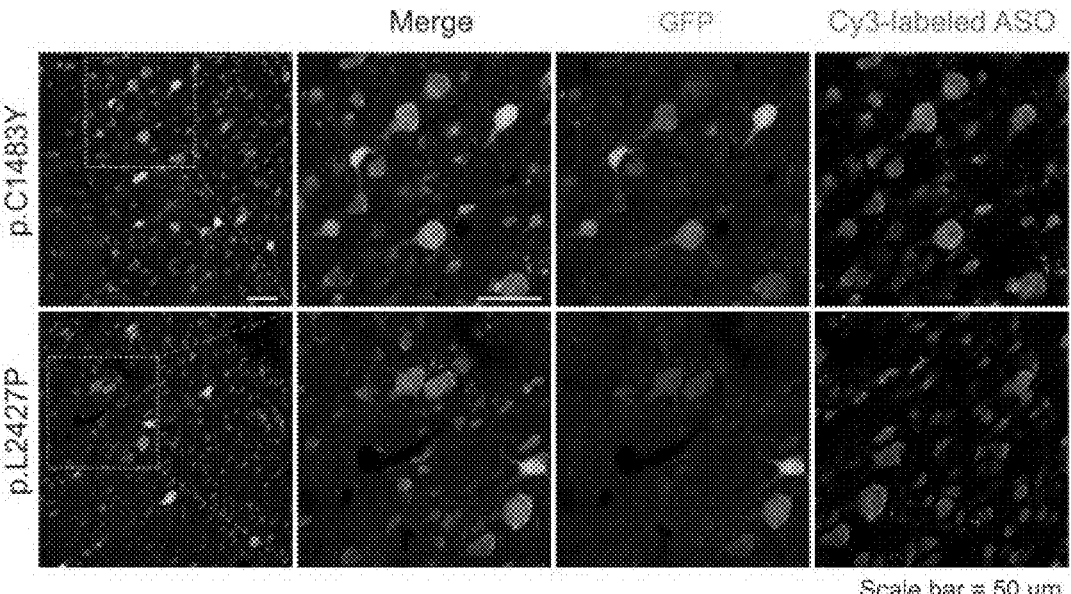

Results of intracerebroventricular injection of ASO to mice are depicted in FIGS. 20a and 20b for a normal mouse and the FMCD epilepsy animal model of Example 1-5, respectively.

FIGS. 20a and 20b show distributions of control ASO in brain cells after intracerebroventricular injection. FIG. 20a shows a distribution of ASO through the fluorescence of Cy3 that was labeled to the ASO, in a normal mouse. FIG. 20b shows the penetration of ASO labeled with Cy3 into the mutant-expressing cells (GFP labeled) of the p.C1483Y and p.L2427P mice as the FMCD epilepsy animal models described in Example 1-5.

5-3 Expression Recovery of ADK, IRSp53, and CREB1 and Reduction of Intracellular eIF4E Expression in Animal Model by ASO Injection Week 4-5 after intracerebroventricular injection of ASO into the animal models established using pCIG-mTOR mutant-IRES-EGFP vector of Example 1, the brain was removed, fixed, sectioned, and immunostained.

Immunostaining with antibodies against ADK, CREB1, IRSp53, and eIF4E and Imaging with fluorescence were conducted in the same manner as in Example 2.

Figure 21A:
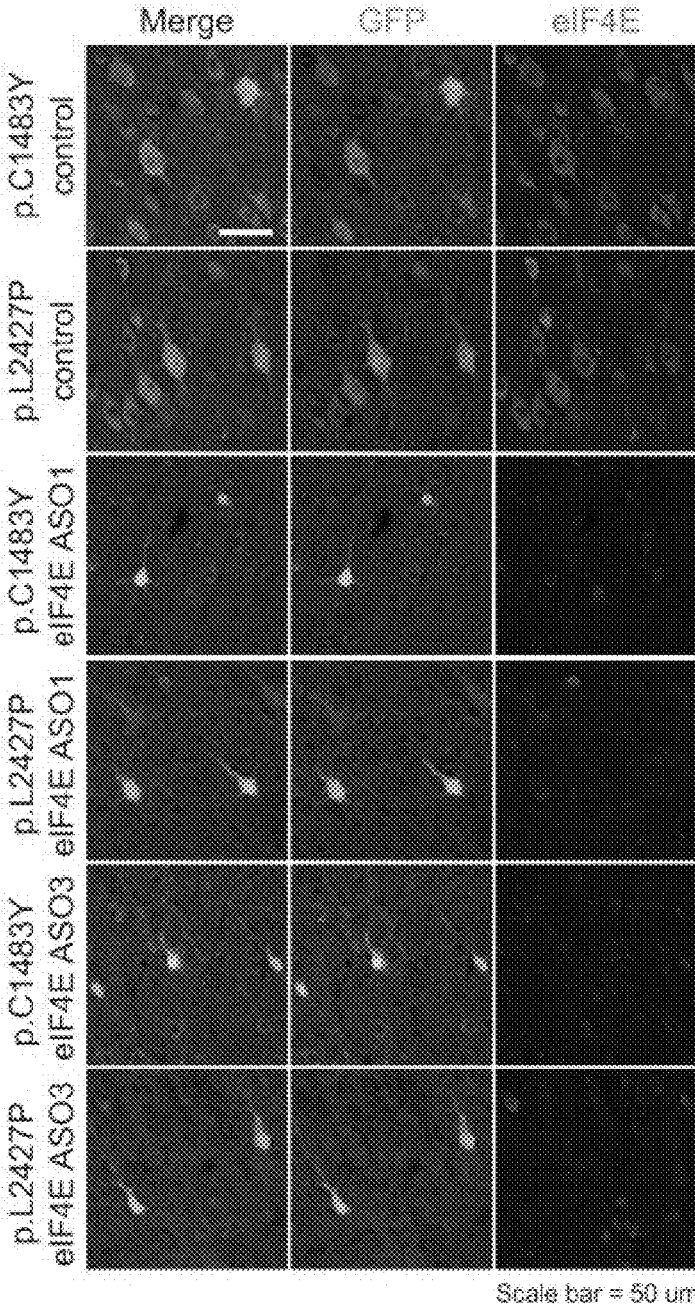
FIG. 21*a* shows the reduction of eIF4E expression in brain cells by ASO injection as analyzed by immunofluorescence analysis.

FIG. 21a shows the reduction of eIF4E expression in brain cells by ASO #75 (ASO-1) and MO #77 (ASO-3) injection as analyzed by immunofluorescence. As can be seen, ASO 1 and ASO 3 (red labeled) were effectively delivered into mutant-expressing cells (GFP labeled) in the brain tissue of the epilepsy mouse models.

Figure 21B:
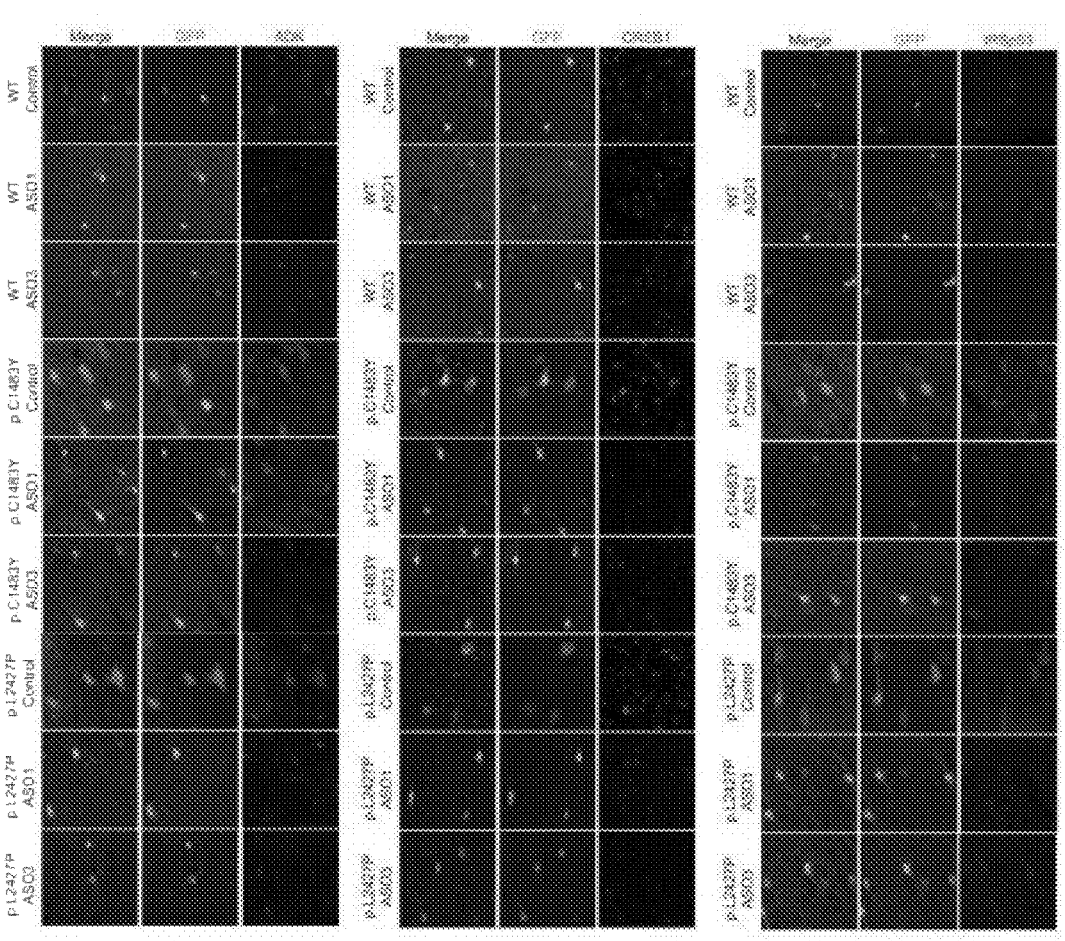
FIG. 21*b* shows rescue of the expression of ADK, IRSp53, and CREB1 to a normal level after injection of ASOs according to Example 5.

FIG. 21b shows rescue of the expression of ADK, IRSp53, and CREB1 to a normal level in the mutation cells after injection of ASO #75 (ASO-1) and ASO #77 (ASO-3). ADK, IRSp53, and CREB1 are mTOR activation-sensitive genes the translation levels of which are increased by the mTOR activating mutation-mediated upregulation of eIF4E activity. Suppression of eIF4E expression by ASO in the mutant cells rescues the expression of ADK, IRSp53, and CREB1 to normal levels.

5-4: Analysis of Cortical Dysplasia and Neuronal Cell Size in Animal Model with eIF4E Expression Reduced by ICV Injection of ASO Week 4-5 after intracerebroventricular injection of ASO into the FMCD animal models established using pCIG-mTOR mutant-IRES-EGFP vector of Example 1, the brain was removed, fixed, sectioned, and immunostained. For neuronal cell size (FIG. 22), GFP (green)-labeled mutant cells (ASO control or ASO eIF4E) were measured for size in the obtained mouse brain tissues.

Figure 22:
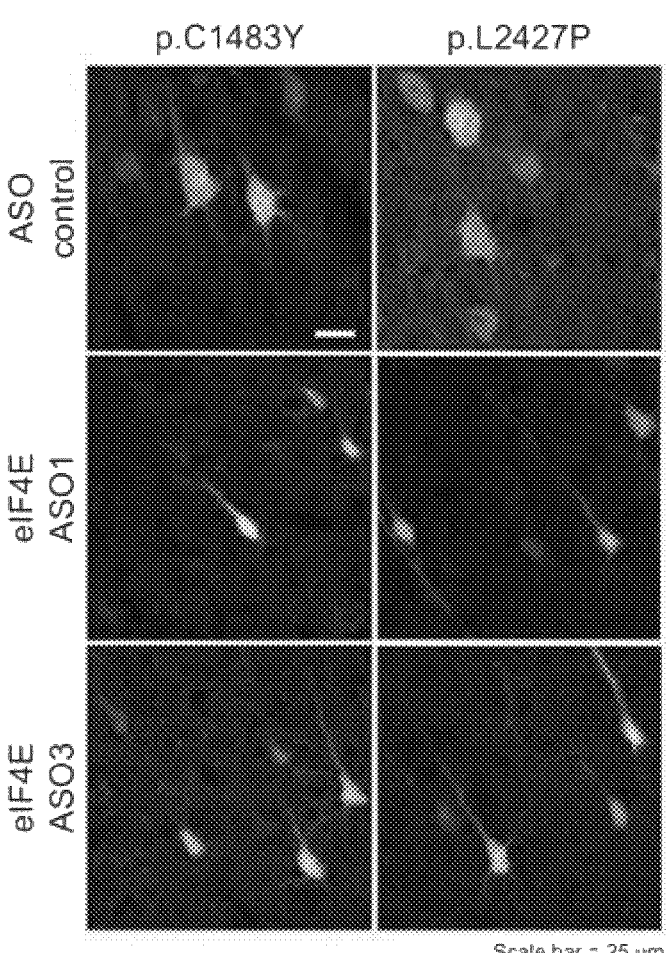
FIG. 22 shows the therapeutic effects of ASOs according to Example 5 in terms of mutant cell size.

FIG. 22 shows the therapeutic effects of ASO #75(ASO-1) and ASO #77 (ASO-3) in intractable epilepsy models in terms of mutant cell size. Suppression of eIF4E expression by ASO can revert the increased neuronal cell size mediated by mTOR pathway activating mutation in intractable epilepsy patients.

<Example 6> Behavioral Assay of Normal Animal According to ASO Injection 6-1: Experimental Mouse and ASO A therapeutic effect on behavioral abnormality that occurred in control normal models (C57BL/6J mice) upon ASO injection was examined. In this regard, ASO was administered by ICV injection. The ASO used in this experiment was ASO #77.

The ASO-injected control animal model was evaluated for behavioral abnormality in the manners as in Examples 6-2 and 6-10. The results of behavioral abnormality assay according to ASO injection to the mice are depicted in FIGS. 23 to 24.

6-2: Body Weight and Temperature Measurement

Mice weighed every week after ASO injection.

The body temperature was measured after anesthesia of the mice. Briefly, mice were placed within an anesthesia induction chamber. Anesthesia was induced and maintained for 2 min with 0.4 L/min of oxygen and isoflurane. During anesthetic maintenance, rectal temperatures were measured using rodent warmer xl (STOELTING). The rectal temperature probe was inserted 2 cm into rectum, 10 seconds after which temperatures were measured.

Figure 23A:
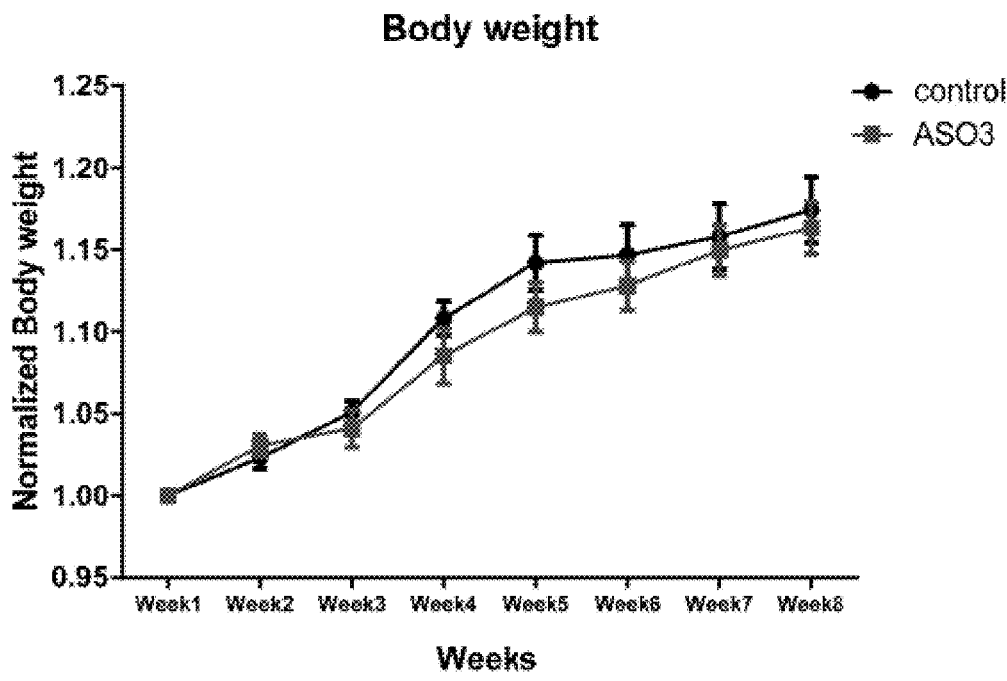
FIGS. 23*a* to 23*c* show a few side effects (body temperature, weight, and neuropsychiatric effect) of ASOs according to Example 6.
Figure 23B:
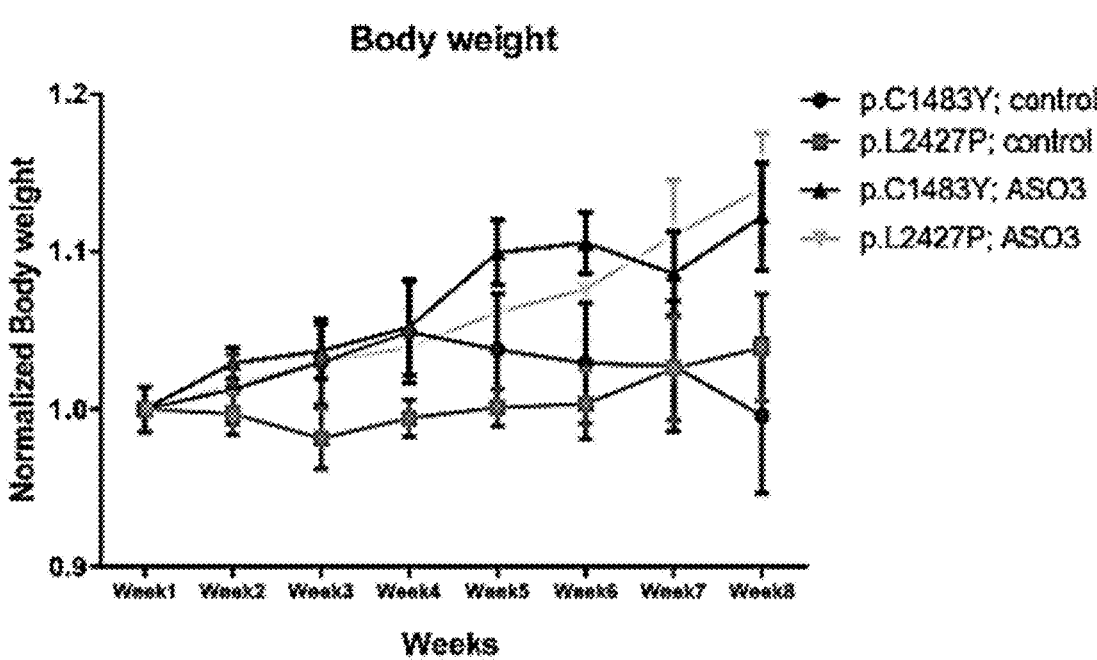
Figure 23C:
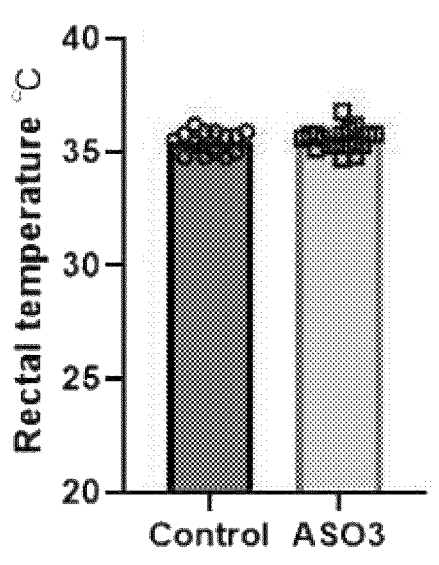
Figure 23C:
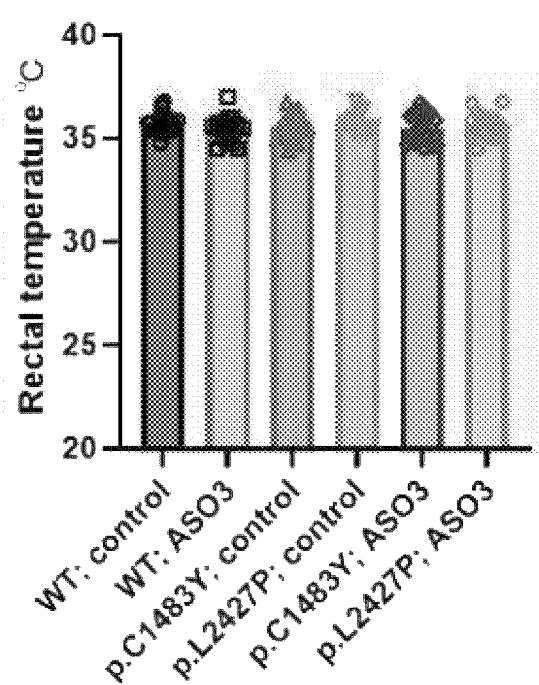
Figure 24:
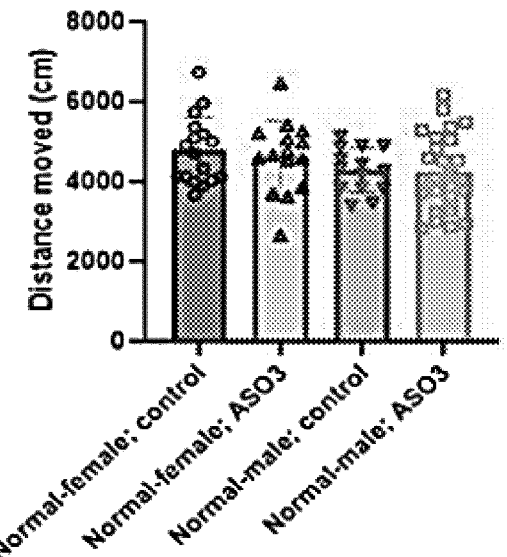
FIGS. 24 to 25 show effects of ASOs on neuropsychiatric disorders which the control animal model accompanies according to Example 6.
Figure 24:
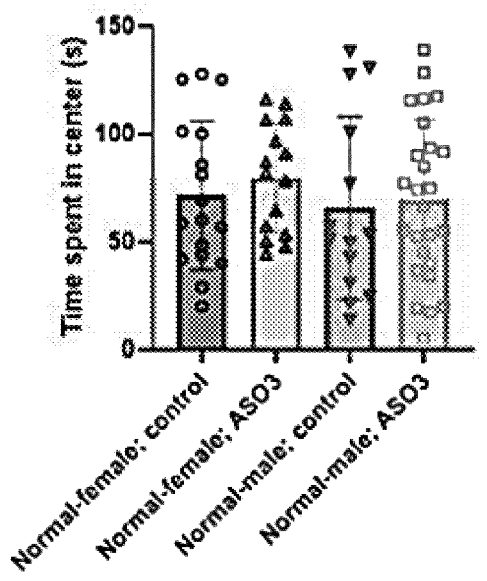
Figure 24:
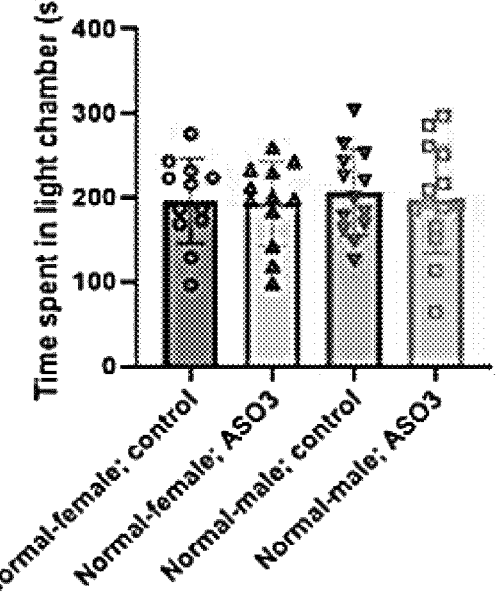
Figure 24:
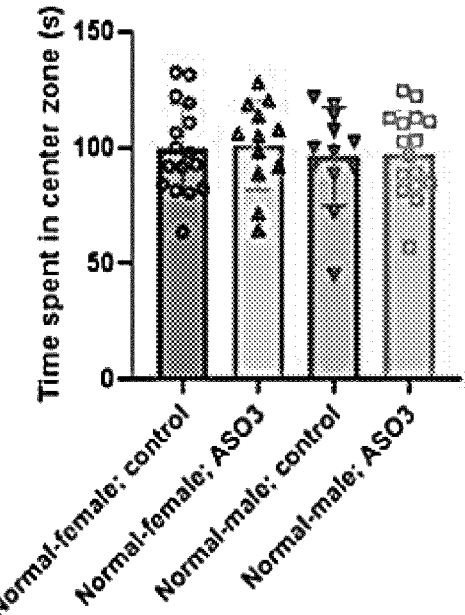

FIG. 23a shows weight measurements over 8 weeks after ASO injection into 8-week-old C57BL/6J mice, with no weight changes occurring due to ASO injection. FIG. 23b shows weight measurements over 8 weeks after ASO injection into 8-week-old mTOR mutation C57BL/6J mice, with body weights recovered to normal conditions by ASO injection. FIG. 23c (A) shows body temperatures at day 21 after ASO injection into the C57BL/6J mice, with no body temperature changes caused by ASO injection. In panel (A) of FIG. 23c, measurements of body temperatures of intractable epilepsy mouse models (mTOR-p.C1483Y, mTOR-p.L2427P) and control (mTOR-WT) at day 21 after ASO injection was given, indicating that the body temperature was not changed by ASO injection 6-3: Mouse Handling Mouse handling was performed for 10 min at the same time every day for 5 days before behavioral test so that the mice were allowed to feel secure with the handler. In order for the mice to receive minimal stress, a one day interval was posed between different behavioral tests. All of the behavioral tests were analyzed in double-blind trials.

6-4: Open Field Test

Before behavioral tests, mice underwent a habituation procedure for 10 min in the test space. The mouse was placed in a box with a dimension of 40×40 (cm), allowed to freely move therein, and measured for open field activity for 10 min. Behaviors were recorded and analyzed using EthoVision XT (Noldus). The mice were returned back to their home cages and the experiment apparatus was washed with 70% EtOH.

FIG. 24 (A) shows results of the behavior test conducted from day 21 after ASO injection into C57BL/6J mice, exhibiting that there was no dyskinesia caused by ASO injection. FIG. 24 (B) shows results of the open field test, demonstrating the safety of ASO in the nervous system as the time spent in center, which is an index of anxiety, was not changed in normal mice injected with ASO.

6-5: Light & Dark Box Test

Before each experiment, mice were subjected to a habituation procedure for 10 min in a test space. Each mouse was placed in a light & dark box with a dimension of 20×20 (cm) and allowed to freely move for 10 min therein. Behaviors were recorded and analyzed using EthoVision XT (Noldus). The mice were returned back to their home cages and the experiment apparatus was washed with 70% EtOH.

FIG. 24 (C) shows results of the light & dark box test, demonstrating the safety of ASO in the nervous system as the time spent in center (residence time within the light box), which is an index of anxiety, was not changed in normal mice injected with ASO.

6-6: Social Avoidance Test

A video tracking system was used to score approach-avoidance behaviors toward an unfamiliar social target. The arena was a black box (400×400 mm). Each experimental mouse was introduced into the black box and its trajectory was tracked for two consecutive sessions of 2.5 min. During the first session ("no target") the box contained an empty perforated cage (10×6.5 cm). During the second session ("target"), the conditions were identical except that a social target (an unfamiliar CD1 mouse) had been introduced into the cage. Between the 2 sessions, the experimental mouse was removed from the arena, and was placed back into its home cage for one min. The video tracking data from both the "no target" and "target" conditions were used to determine the time spent by the experimental mouse in the "interaction zone", which was a corridor surrounding the cage.

FIG. 24 (D) shows results of the social avoidance test, demonstrating the safety of ASO in the nervous system as the time spent in center (the time spent to interact with the stranger mouse), which is an index of sociality and depression, was not changed in normal mice injected with ASO.

6-7: 3-Chamber Test (Social Interaction Test)

The 3-Chamber test measures social interaction and preference for social novelty. This apparatus consisted of three chambers with dimensions of 12×20×26 cm for the center chamber and dimensions of 14×20×26 cm for the opposite side chambers. Each of the opposite side chambers included a plastic cage (11 cm in diameter, 2.15 cm in height) for an object or stranger mouse in a corner. This experiment consisted of three sessions of habituation (10 min), exploring object/mouse (10 min), and exploring familiar/new mouse (10 min). In the second session, a WT stranger mouse was randomly placed in a plastic cage while the opposite plastic cage was empty. The mouse was allowed to freely explore the whole apparatus. The time spent in each chamber was measured and then used for the subsequent social interaction test. In the last session, a new WT stranger was placed in the empty plastic cage.

Figure 25:
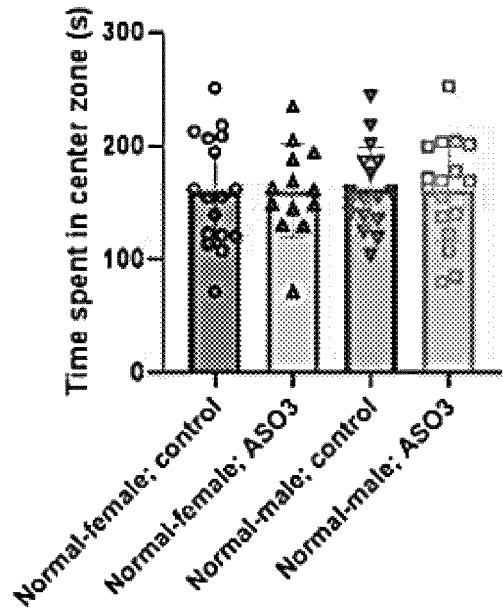
Figure 25:
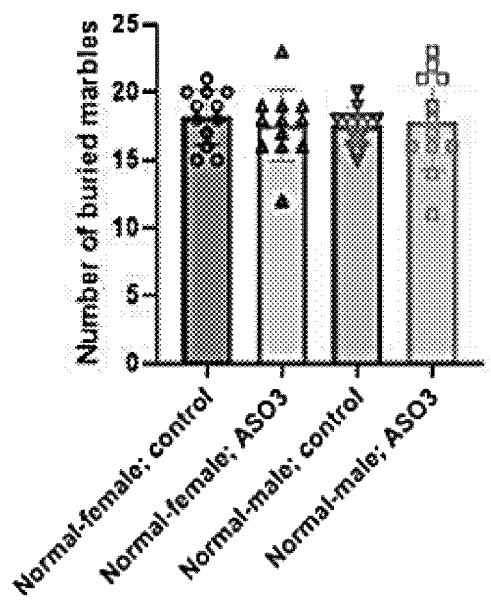
Figure 25:
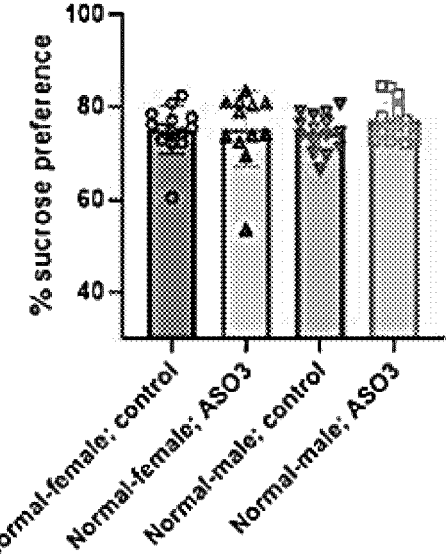

FIG. 25 (E) shows results of the 3-chamber test (Social interaction), demonstrating the safety of ASO in the nervous system as the time spent in sniffing zone (the time spent to interact with the stranger mouse), which is an index of sociality, was not changed in either male or female mice injected with MO.

6-8: Marble Burying Test

A general mouse cage covered with a filter-equipped lid was used. Fresh bedding free of mouse smells was evenly laid to the height of 5 cm in each cage. Glass marbles, each weighing 5 g with a diameter of 15 mm, were arranged in six rows of four on the bedding. The marbles were cleaned with a detergent and washed with deionized water. A mouse was placed in the cage. Twenty minutes after the cage was covered with the lid, buried marbles were counted. A marble was considered to be buried when half of its height was hidden in the bedding.

FIG. 25 (F) shows results of the marble burying test, demonstrating the safety of ASO in the nervous system as the number of buried marbles, which is an index of repetitive behavior, was not changed in either male or female mice injected with ASO.

6-9: Sucrose Preference Test

Each of mice was habituated for 3-5 days in a cage with two selectable water bottles presented. Thereafter, the mice were each placed in the same cage as the habituation cage at the day of experiment. The mice were presented with two dual bottles, one containing tap water and the other containing 1% sucrose solution. Water and sucrose solution intake was measured after 24 hours and sucrose preference was calculated according to volume of sucrose intake/total volume of fluid intake×100%.

FIG. 25 (G) shows results of the sucrose preference test, demonstrating the safety of ASO in the nervous system as % sucrose preference, which is an index of pleasure or compensation dysfunction, was not changed in either male or female mice injected with ASO.

<Example 7> Assay for Therapeutic Potential of eIF4E Inhibitor on Neuropsychiatric Disorder 7-1: Suitability Evaluation of FMCD Animal Model The FMCD animal models of Example 1 (mTOR-p.C1483Y, mTOR-p.L2427P) were evaluated for suitability for use in assaying neuropsychiatric disorders that accompany FMCD and epilepsy models.

The FMCD animal models with epilepsy were subjected to the substantially same behavioral abnormality assay according to FMCD as in Example 6. The results are depicted in FIGS. 26 and 27 for the epilepsy animal models that had not been treated with a therapeutic agent.

Figure 26:
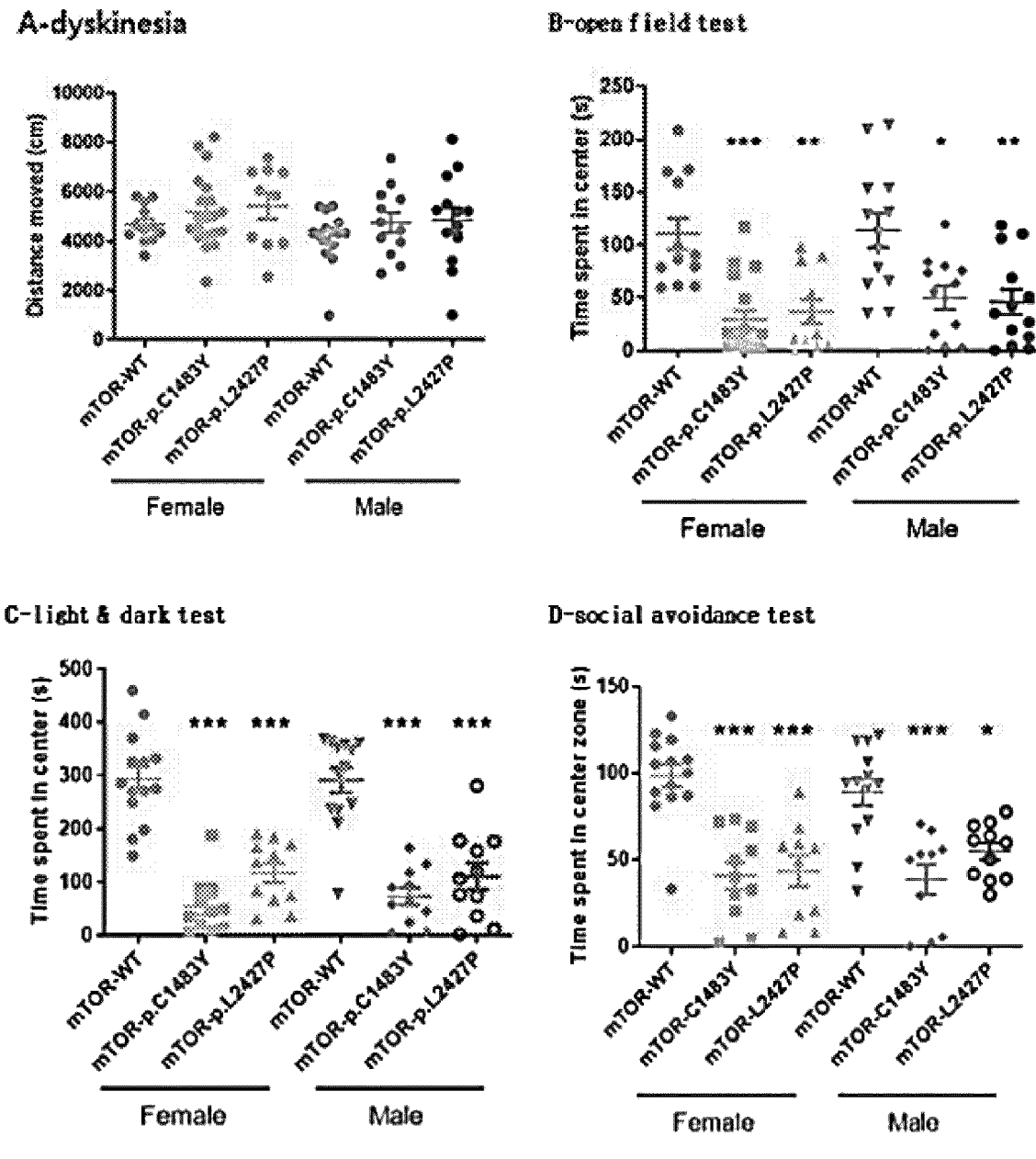
FIGS. 26 to 27 show neuropsychiatric disorders which the FMCD models according to Example 7.
Figure 27:
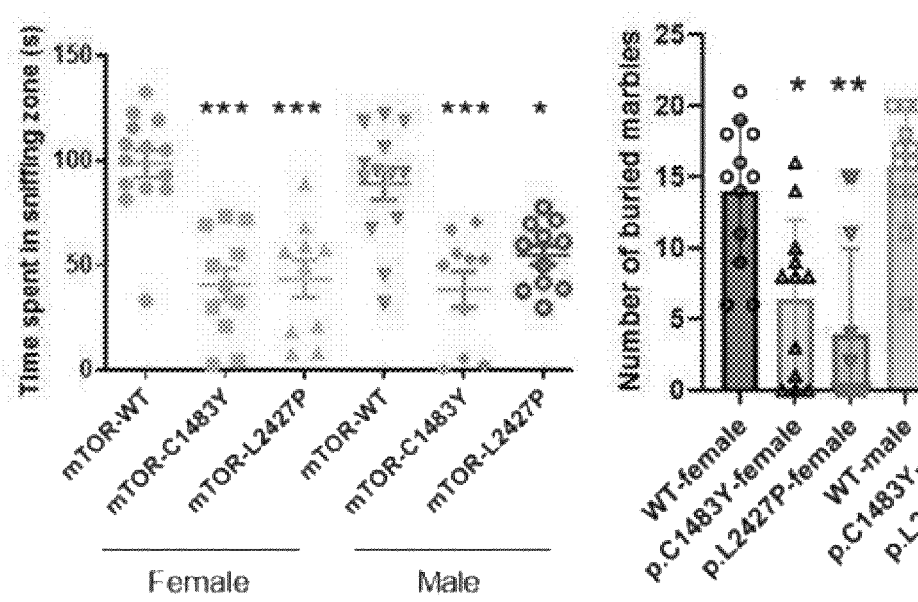
Figure 27:
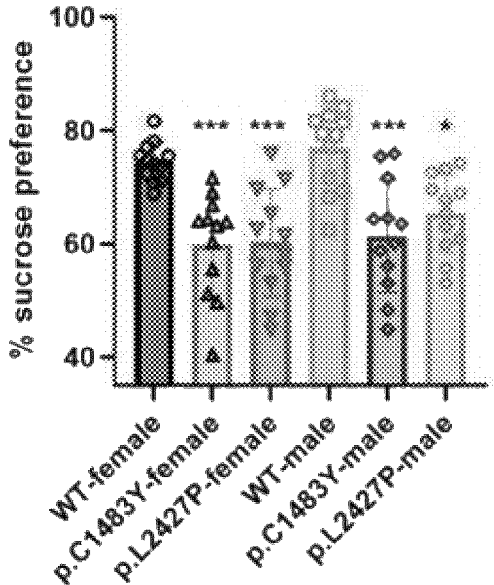

FIG. 26 (A) shows results of the behavior test, demonstrating that both the male and female intractable epilepsy models (mTOR-p.C1483Y, mTOR-p.L2427P) did not undergo dyskinesia.

FIG. 26 (B) shows results of the open field test, demonstrating an increased degree of anxiety as the time spent in center, which is an index of anxiety, was reduced in both the male and female intractable epilepsy models (mTOR-p.C1483Y, mTOR-p.L2427P).

FIG. 26 (C) shows results of the light & dark box test, demonstrating an increased degree of anxiety as the time spent in center (residence time within the light box), which is an index of anxiety, was reduced in both the male and female intractable epilepsy models (mTOR-p.C1483Y, mTOR-p.L2427P).

FIG. 26 (D) shows results of the social avoidance test, demonstrating decreased sociality and an increased degree of depression as the time spent in center (the time spent to interact with the stranger mouse), which is an index of sociality and depression, was reduced in both the male and female intractable epilepsy models (mTOR-p.C1483Y, mTOR-p.L2427P).

FIG. 27 (E) shows results of the 3-chamber test (Social interaction), demonstrating decreased sociality as the time spent in sniffing zone (the time spent to interact with the stranger mouse), which is an index of sociality, was reduced in both the male and female intractable epilepsy models (mTOR-p.C1483Y, mTOR-p.L2427P).

FIG. 27 (F) shows results of the marble burying test, demonstrating decreased repetitive behavior as the number of buried marbles, which is an index of repetitive behavior, was reduced in both the male and female intractable epilepsy models (mTOR-p.C1483Y, mTOR-p.L2427P). That is, both the male and female intractable epilepsy models (mTOR-p.C1483Y, mTOR-p.L2427P) were observed to have abnormality in repetitive behavior in light of the results of the marble burying test that the number of buried marbles, which is an index of repetitive behavior, reduced FIG. 27 (G) shows results of the sucrose preference test, demonstrating reduced pleasure or reward function as % sucrose preference, which is an index of pleasure or reward dysfunction, was reduced in both the male and female intractable epilepsy models (mTOR-p.C1483Y, mTOR-p.L2427P).

7-2: Assay for Therapeutic Potential of sheIF4E on Neuropsychiatric Disorder

Experiments were performed on the FMCD and epilepsy animal models (mTOR-p.C1483Y, mTOR-p.L2427P) of Example 7-1 and the control normal animal models (mTOR-WT). The same sheIF4E as that described in Example 2 was used. Week 2 after sheIF4E injection, the handling was performed in the animals. Week 3 after sheIF4E injection, the animals were subjected to the behavioral tests.

The epilepsy animal models were subjected to the substantially same behavioral abnormality assay as in Example 6. The results are depicted in FIGS. 28 and 29.

Figure 28:
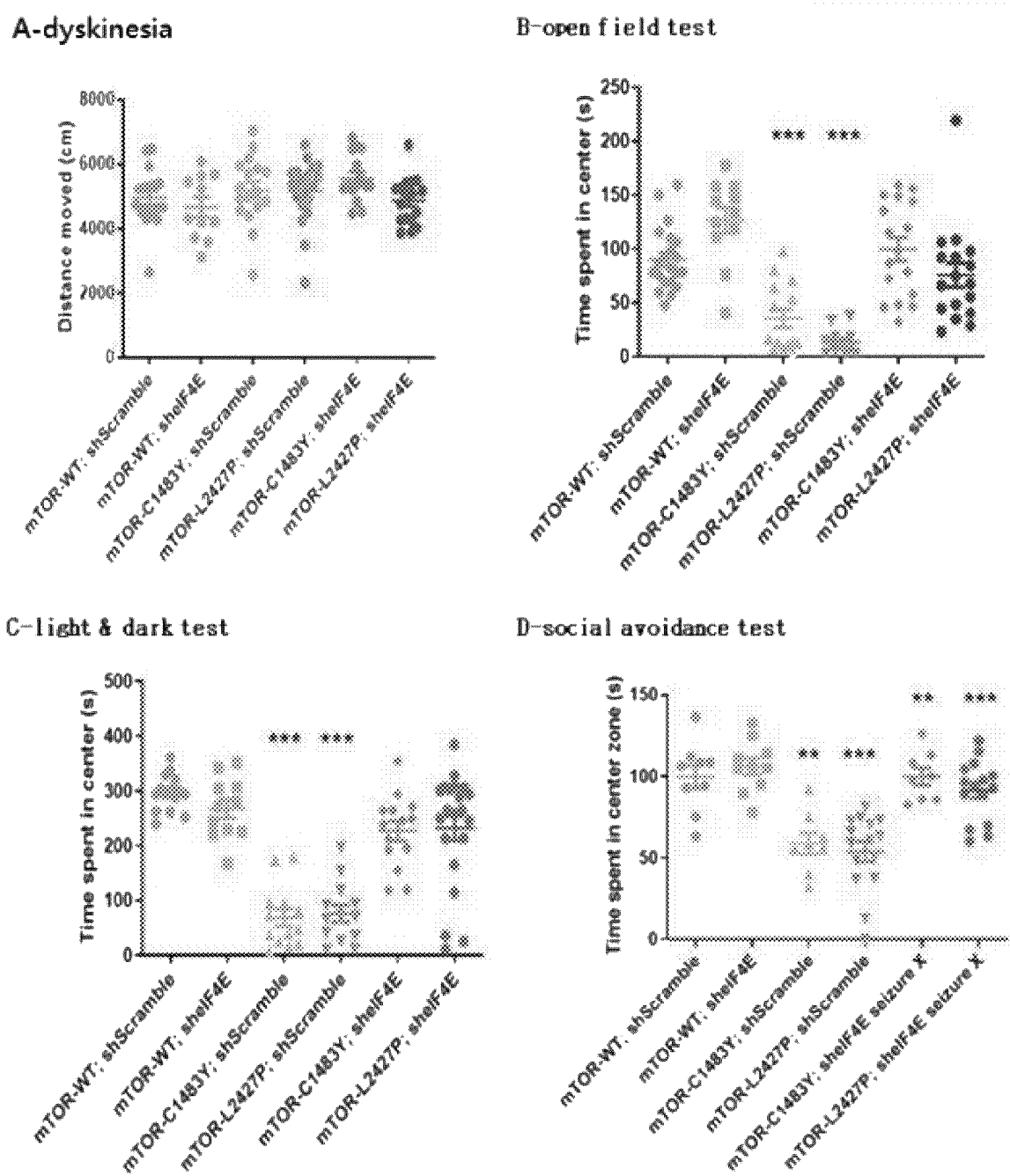
FIGS. 28 to 29 show therapeutic effects of sheIF4E on neuropsychiatric disorders in FMCD models according to Example 7.
Figure 29:
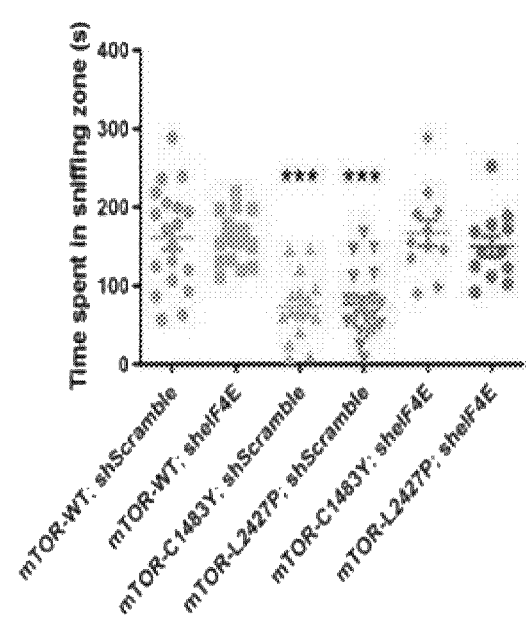
Figure 29:
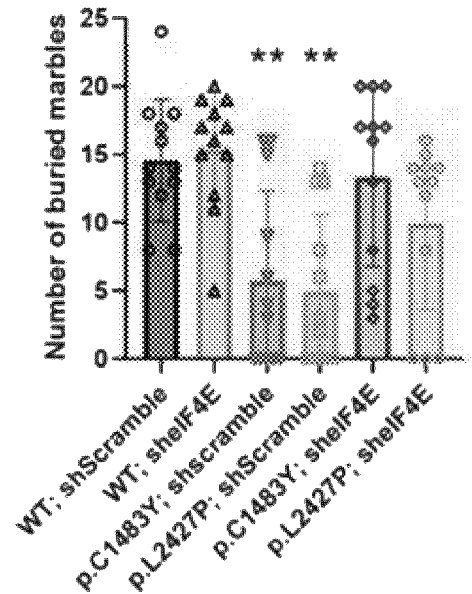
Figure 29:
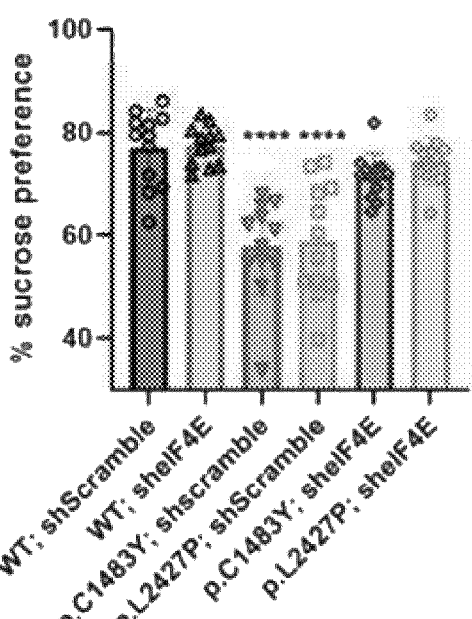

In FIGS. 28 and 29, therapeutic potentials of sheIF4E for neuropsychiatric disorders accompanying the intractable epilepsy model are explained.

FIG. 28 (A) shows results of the behavior test, demonstrating that there is no dyskinesia in the intractable epilepsy models having sheIF4E.

FIG. 28 (B) shows results of the open field test, demonstrating the therapeutic effect of shRNA on anxiety as the time spent in center, which is an index of a degree of anxiety, was increased in the intractable epilepsy models (mTOR-p.C1483Y;mU6-sheIF4E, mTOR-p.L2427P;mU6-sheIF4E) having shRNA-mediated downregulation of eIF4E expression, compared to the intractable epilepsy models (mTOR-p.C1483Y;mU6-shscramble, mTOR-p.L2427P;mU6-shscramble)

FIG. 28 (C) shows results of the light & dark box test, demonstrating the therapeutic effect of shRNA on anxiety as the time spent in center (residence time within the light box), which is an index of a degree of anxiety, was increased in the intractable epilepsy models (mTOR-p.C1483Y;mU6-sheIF4E, mTOR-p.L2427P;mU6-sheIF4E) having shRNA-mediated downregulation of eIF4E expression, compared to the intractable epilepsy models (mTOR-p.C1483Y;mU6-shscramble, mTOR-p.L2427P;mU6-shscramble).

FIG. 28 (D) shows results of the social avoidance test, demonstrating the therapeutic effect of shRNA on social ability and depression as the time spent in center (the time spent to interact with the stranger mouse), which is an index of social ability and depression, was increased in the intractable epilepsy models (mTOR-p.C1483Y;mU6-sheIF4E, mTOR-p.L2427P;mU6-sheIF4E) having shRNA-mediated downregulation of eIF4E expression, compared to the intractable epilepsy models (mTOR-p.C1483Y;mU6-shscramble, mTOR-p.L2427P;mU6-shscramble).

FIG. 29 (E) shows results of the 3-chamber test (Social interaction), demonstrating the therapeutic effect of shRNA on social ability as the time spent in sniffing zone (the time spent to interact with the stranger mouse), which is an index of social ability, was increased in the intractable epilepsy models (mTOR-p.C1483Y;mU6-sheIF4E, mTOR-p.L2427P;mU6-sheIF4E) having shRNA-mediated downregulation of eIF4E expression, compared to the intractable epilepsy models (mTOR-p.C1483Y;mU6-shscramble, mTOR-p.L2427P;mU6-shscramble).

FIG. 29 (F) shows results of the marble burying test, demonstrating the therapeutic effect of shRNA on repetitive behavior as the number of buried marbles, which is an index of repetitive behavior, was increased in the intractable epilepsy models (mTOR-p.C1483Y;mU6-sheIF4E, mTOR-p.L2427P;mU6-sheIF4E) having shRNA-mediated downregulation of eIF4E expression, compared to the intractable epilepsy models (mTOR-p.C1483Y;mU6-shscramble, mTOR-p.L2427P;mU6-shscramble).

FIG. 29 (G) shows results of the sucrose preference test, demonstrating the therapeutic effect of shRNA on pleasure or reward function as % sucrose preference, which is an index of pleasure or reward dysfunction, was increased in the intractable epilepsy models (mTOR-p.C1483Y;mU6-sheIF4E, mTOR-p.L2427P;mU6-sheIF4E) having shRNA-mediated downregulation of eIF4E expression, compared to the intractable epilepsy models (mTOR-p.C1483Y;mU6-shscramble, mTOR-p.L2427P;mU6-shscramble).

7-3: Assay for Therapeutic Potential of ASO on Neuropsychiatric Disorder

Experiments were performed on the FMCD and epilepsy animal models (mTOR-p.C1483Y, mTOR-p.L2427P) of Example 7-1 and the control normal animal models (mTOR- WT). ASO #77, which downregulates the expression of eIF4E, was employed in this experiment.

Briefly, ASO #77 was administered by ICV injection to the FMCD and epilepsy animal models were generated with the pCIG-mTOR mutant-IRES-EGFP of Example 1. ASO #77 was evaluated for therapeutic potential for neuropsychiatric disorder accompanying the FMCD epilepsy animal models in the substantially same manner as in Example 6.

Figure 30:
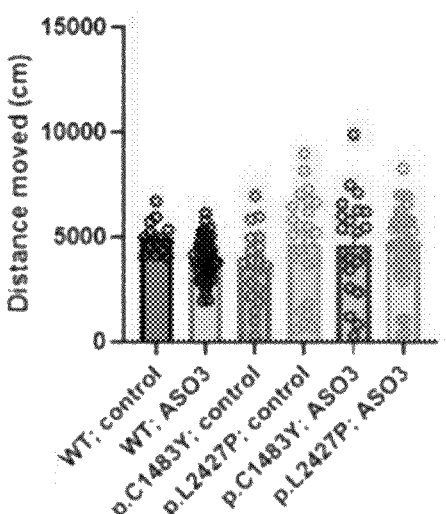
FIGS. 30 to 31 show therapeutic effects of ASO 3 on neuropsychiatric disorders in intractable epilepsy models according to Example 7.
Figure 30:
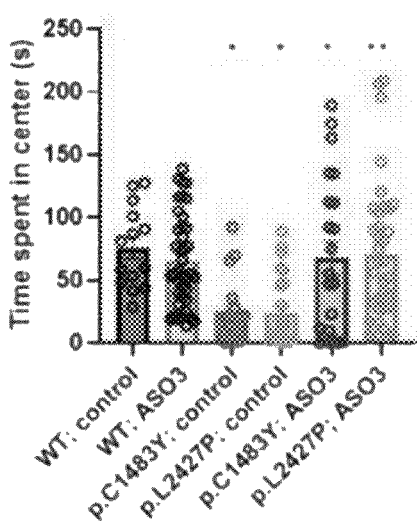
Figure 30:
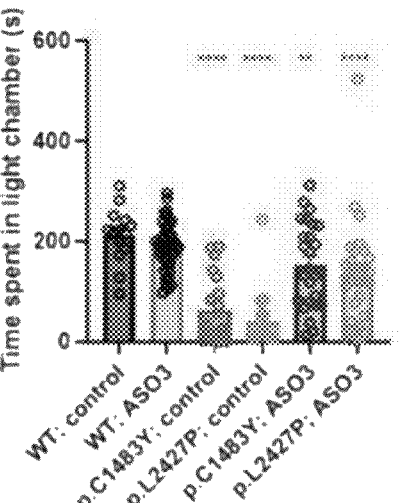
Figure 30:
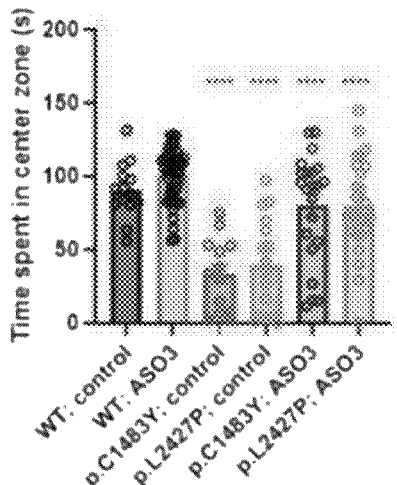
Figure 31:
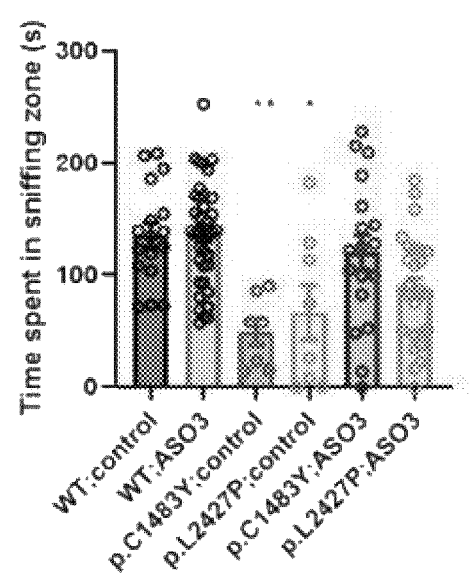
Figure 31:
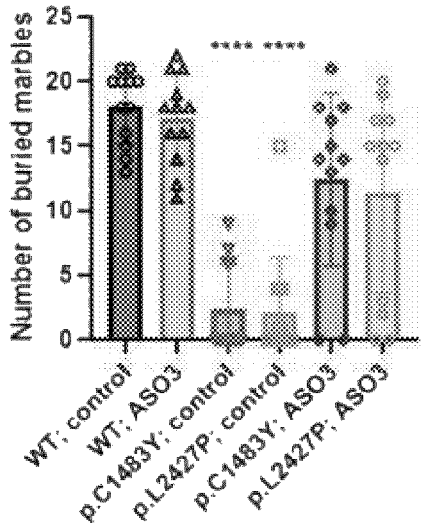
Figure 31:
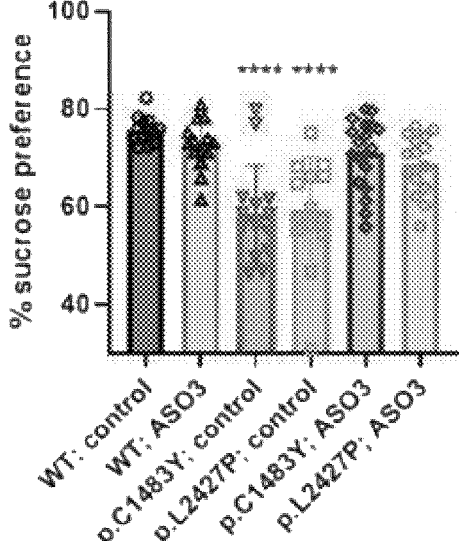

Results of the assay for therapeutic potential of ASO on neuropsychiatric disorders of the FMCD animal models according to MO-mediated eIF4E knockdown in the epilepsy model mice are depicted in FIGS. 30 to 31. FIGS. 30 and 31 show therapeutic effects of ASO #77 (ASO-3) on neuropsychiatric disorders accompanying the intractable epilepsy models.

FIG. 30 (A) shows results of the behavior test performed from day 21 after MO #77 (ASO-3) injection, demonstrating that there is no dyskinesia according to ASO injection.

FIG. 30 (B) shows results of the open field test, demonstrating the therapeutic effect of ASO #77 (ASO-3) on anxiety as the time spent in center, which is an index of a degree of anxiety, was increased in the FMCD and epilepsy models (mTOR-p.C1483Y;ASO-eIF4E, mTOR-p.L2427P; ASO-eIF4E) having ASO #77 (ASO-3)-mediated downregulation of eIF4E expression, compared to the intractable epilepsy models (mTOR-p.C1483Y;ASO-control, mTOR-p.L2427P;ASO-control).

FIG. 30 (C) shows results of the light & dark box test, demonstrating the therapeutic effect of ASO #77 (ASO-3) on anxiety as the time spent in center (residence time within the light box), which is an index of a degree of anxiety, was increased in the FMCD and epilepsy models (mTOR-p.C1483Y;ASO-eIF4E, mTOR-p.L2427P;ASO-eIF4E) having ASO #77 (ASO-3)-mediated downregulation of eIF4E expression, compared to the intractable epilepsy models (mTOR-p.C1483Y;ASO-control, mTOR-p.L2427P;ASO-control).

FIG. 30 (D) shows results of the social avoidance test, demonstrating the therapeutic effect of ASO on social ability and depression as the time spent in center (the time spent to interact with the stranger mouse), which is an index of social ability and depression, was increased in the FMCD and epilepsy models (mTOR-p.C1483Y;ASO-eIF4E, mTOR-p.L2427P;ASO-eIF4E) having ASO-mediated downregulation of eIF4E expression, compared to the intractable epilepsy models (mTOR-p.C1483Y;ASO-control, mTOR-p.L2427P;ASO-control).

FIG. 31 (E) shows results of the 3-chamber test (Social interaction), demonstrating the therapeutic effect of ASO on social ability as the time spent in sniffing zone (the time spent to interact with the stranger mouse), which is an index of social ability, was increased in the FMCD and epilepsy models (mTOR-p.C1483Y;ASO-eIF4E, mTOR-p.L2427P; ASO-eIF4E) having ASO-mediated downregulation of eIF4E expression, compared to the intractable epilepsy models (mTOR-p.C1483Y;ASO-control, mTOR-p.L2427P; ASO-control).

FIG. 31 (F) shows results of the marble burying test, demonstrating the therapeutic effect of ASO on repetitive behavior as the number of buried marbles, which is an index of repetitive behavior, was increased in the FMCD and epilepsy models (mTOR-p.C1483Y;ASO-eIF4E, mTOR-p.L2427P;ASO-eIF4E) having ASO-mediated downregulation of eIF4E expression, compared to the intractable epilepsy models (mTOR-p.C1483Y;ASO-control, mTOR-p.L2427P;ASO-control).

FIG. 31 (G) shows results of the sucrose preference test, demonstrating the therapeutic effect of ASO on pleasure or reward function as % sucrose preference, which is an index of pleasure or reward dysfunction, was increased in the FMCD and epilepsy models (mTOR-p.C1483Y;ASO-eIF4E, mTOR-p.L2427P;ASO-eIF4E) having ASO-mediated downregulation of eIF4E expression, compared to the intractable epilepsy models (mTOR-p.C1483Y;ASO-control, mTOR-p.L2427P;ASO-control).

<Example 8> Identification of eIF4E Hyperactivation-Sensitive Gene 8-1: Construction of Neuronal Cell Having mTOR Mutation Mutant cells in the FMCD animal models of Example 1 were labeled with GFP and the GFP-positive cells were sorted by fluorescence-activated cell sorting (FACS) to acquire mTOR mutant cells.

In brief, from in utero-electroporated mice, cortical neurons expressing MTOR-WT, MTOR-p.Cys1483Tyr, or MTOR-p.Leu2427Pro, along with GFP reporter, were dissected at E18.5 in Hank's balanced salt solution (Life Technologies) supplemented with 10 mM HEPES (Gibco, 15630-080) and Pen/Strep (Life Technologies, 15140-122). For analysis of protein expression regulation, the medium was added with 100 µg/mL cycloheximide (Millipore, 239763), which is a ribosome elongation inhibitor.

In order to discriminate mutation-expressing cells, GFP-positive cortical portions were identified from the electroporated regions and excised in Hibernate-E medium (Gibco, A12476-01) supplemented with GlutaMAX4 (Gibco, 35050-061) and B27 (Gibco, 17504-044). GFP-positive cortices were digested in dissection medium containing 0.05% trypsin (Life Technologies, 15090-046) for 30 minutes at 4° C. After digestion, pellets were centrifuged and resuspended three times in Hibernate-E medium supplemented with GlutaMAX-I and B27.

To dissociate cells, fire-polished Pasteur pipettes (Corning, CO-7095B-9) were used. Sequentially, 100-µm and 40-µm strainers were used to remove large debris. Cell sorting was performed with the BD FACSAria II Flow Cytometer (BD Biosciences) with FITC gating. Sorted cortical neurons were stored at −80° C. for up to 6 months.

8-2: Translatome Profiling Using mTOR Mutation-Expressing Cell

Translatome profiling identified genes that have mRNA translation upregulated by mTOR mutation. mRNA translation of the genes was increased by mTOR mutation. As seen in FIG. 2, ribosome profiling in intractable epilepsy mouse models with brain somatic mutations can reveal mTOR target genes contributing to FMCD. The genes that had an expression level increased by mTOR mutation were explained by the mTOR mutation-mediated increases of mRNA translation.

8-3: Preparation of Ribo-Seq and RNA-Seq Library (1) Ribosome Profiling (Ribo-Seq) and RNA Sequencing (RNA-Seq)

Cells were seeded in 10-cm dishes at 50% confluence. The cells had not reached maximum confluence by the following day. NIH 3T3 cells were treated with 200 nM Torin1 or vehicle, and CRISPR-edited mTOR (G4448A)-pC1483Y NIH 3T3 cells were treated with vehicle for 3 hours. The cells were washed once with ice-cold PBS supplemented with 100 µg/mL cycloheximide and lysed in mammalian polysome buffer (10 mM Tris-HCl at pH 7.4, 5 mM $MgCl_2$, 100 mM KCl, 2 mM DTT, 1% Triton X-100, 100 µg/mL cycloheximide supplemented with 1 µL, of protease inhibitor cocktail, 2 µL, of RNasin, and 2 µL, of SUPERase) to maintain binding between the ribosomes and mRNA. The samples were incubated for 20 minutes on a rotator to induce cell lysis. For FACS-sorted cortical neurons, the same treatments were applied. The cell lysates were separated into 2 tubes, 75% of the sample for Ribo-Seq and the rest for RNA-Seq, which were used to prepare Ribo-Seq and RNA-Seq libraries, respectively.

(2) Preparation of Ribo-Seq and RNA-Seq

For Ribo-seq, the prepared cell lysates were treated with RNase I (Ambion, AM2294) to remove the ribosome-unbound region of mRNA from the ribosome-mRNA complexes. Subsequently, the ribosome-mRNA complexes were purified using Sephacryl S-400 columns (GE Healthcare, 27-5140-01). RNA footprints (i.e., ribosome-bound region of mRNA) were extracted from the sample using TRIzol LS (Ambion, 10296-010). rRNA was removed from the sample using a Ribo-zero rRNA removal kit (Epicentre, RZH110424).

For RNA-seq, total RNA was purified from the cell lysates using TRIzol LS. Subsequently, the RNA sample was enriched using RNA Clean & Concentrator-5 or -25 (Zymo Research, R1015 or R1017). rRNA was removed using a Ribo-zero rRNA removal kit (Epicentre, RZH110424). After rRNA removal, the sample RNAs were fragmented via alkaline hydrolysis using the NEBNext Magnesium RNA Fragmentation Module (New England BioLabs, E6150S).

Ribosome footprints (30 nt in size) and RNA fragments (40-60 nt in size) were size-fractionated by Urea-PAGE and purified from the gel elutes.

(3) Antarctic Phosphatase and PNK Treatment

RNase I digestion and alkaline hydrolysis left a monophosphate group at the 3' end of each of the ribosome footprints and RNA fragments, respectively. After removal of the monophosphate group by Antarctic phosphatase (NEB, M0289S), the bare 3' end was connected to the 5' end of an adenylated 3' linker. To this end, the samples were incubated in 20 µl, of 1× reaction mixture containing 1 µL of Antarctic phosphatase for 1 hour at 37° C., and subsequently incubated for 5 minutes at 65° C. to inactivate the enzyme. Following the reaction, the RNAs were incubated in 45 µL of 1× reaction mixture containing 2 of PNK (Takara, 2021A) and 1 of [γ-$^{32}$P]-ATP (PerkinElmer, NEG502Z) for 5 minutes at 37° C. to label the RNA with $^{32}$P. Following the labeling, 5 µL of 1 mM ATP (NEB, P0756L) was added, and the samples were incubated for 10 minutes at 37° C. to phosphorylate the 5' end of the RNAs for subsequent 5' linker ligation. The ribosome footprints and RNA fragments were purified by acidic phenol-mediated RNA extraction and subsequently size-fractionated and purified using Urea-PAGE to remove free ATP.

(4) Linker Ligation, RT-PCR, and Sequencing

TruSeq small RNA kits (Illumina, RS-200-0012) were used for 3' linker, 5' linker, RT primer, 5' primer, and 3' primer ligation.

To ligate the 3' linker, 1.5 µL of T4 RNA ligase 2 (Epicentre, LR2D1132K), 1 µL of 10× buffer, 0.5 µL of 3' linker (RA3, TruSeq Small RNA kit), and 1 µL of SUPERase-In were added to each RNA sample and incubated for 4 hours at 22° C. The linker-ligated RNAs were size-fractionated by Urea-PAGE and then purified from gel elute to remove residual 3' linker.

Subsequently, to ligate the 5' linker, 1 µL of T4 RNA ligase, 1 µL of 10× buffer, 1 µL of 10 mM ATP, 0.5 µL of 5' linker (RA5, TruSeq Small RNA kit), and 1 µL of SUPERase-In were added to each sample and incubated for 16 hours at 22° C.

To construct cDNA libraries, the linker-ligated RNAs were reverse-transcribed in 20 μL of 1× reaction mixture containing 4 μL, of 2.5 mM dNTP, 1 μL of Superscript II RT enzyme, 4 μL, of 5× buffer, and 2 μL of 0.1 M DTT. To amplify the cDNA for Illumina DNA sequencing, 1 μL from a total of 20 of RT sample was mixed with 1 μL of Phusion HF polymerase (Thermo Fisher Scientific, F-530L), 5 μL of 5× buffer, 2.5 mM dNTP, 0.2 μL of 5' primer (TruSeq Small RNA kit), 0.2 μL of 3' primer (TruSeq Small RNA kit), and 33.6 μL of distilled water. This PCR mixture was run for 22-25 cycles of 98° C. for 10 seconds, 60° C. for 30 seconds, and 72° C. for 20 seconds on T1 Thermocycler. The amplified cDNA libraries were purified by Native-PAGE and from gel elute.

The purified cDNA libraries were sequenced using an Illumina HiSeq 2000 or HiSeq 2500 sequencing system. Translatome profiling led to detecting genes having mTOR mutation-mediated expression upregulation.

8-4: Sequencing Processing and Alignment of Ribo-Seq and RNA-Seq Libraries

Some first steps in the sequence analysis were conducted using FASTX-Toolkit of Assaf Gordon (http://hannon-lab.cshl.edu/fastx_toolkit/). The reads thus obtained were trimmed from the 3' end so that the remaining reads were 26 nt long. The reads were aligned with Bowtie (http://bowtie-bio.sourceforge.net/index.shtml) version 1.1.2 to UCSC mm10 assembly to remove rRNA and tRNA Then, the reads were aligned to UCSC mm10 genome sequences using TopHat (http://ccb.jhu.edu/software/tophat/index.shtml) version 2.1.1 with default options, except for no novel junctions.

8-5: mRNA Transcript Quantification and Normalization of Ribo-Seq and RNA-Seq Libraries To quantify ribosome footprint and mRNA abundance of individual genes, Ribo-Seq and RNA-Seq tags were counted per individual transcript after aligning with HTSeq (https://htseq.readthedocs.io/en/release 0.9.1/). Transcripts with low read counts in the Ribo-Seq and RNA-Seq libraries (i.e., FMCD mouse model <100 raw reads in all of the libraries) were excluded to reduce noise. Each read count per individual mRNA transcript was normalized to median values of the read counts in each library.

8-6: Quantification of Translation Efficiencies of Individual mRNA Transcripts

Translational efficiency (1 h) of mRNA transcripts for as many as 5,000 genes was calculated as the normalized read counts of an individual transcript in ribosome-protected mRNA fragments (RPFs) divided by the normalized RNA-Seq tag counts mapped to the coding sequence (CDS). The CDS-mapped RNA-Seq tag counts were also normalized to their medians in the RNA-Seq libraries. Fold changes in the translational efficiencies (TEs) of individual genes at each time point relative to the control were calculated in a log 2 scale.

8-7: Identification of eIF4E Hyperactivation-Sensitive Gene

From the distribution of fold changes in translational efficiencies (TEs) of individual genes at each time point relative to the control, 256 genes with z-score of 1.2 or more in both MTOR-C1483Y and MTOR-L2427P models relative to MTOR-WT model were selected for eIF4E activation-sensitive genes. The z-score of 1.2 or more in the distribution of TE fold changes meets the condition of log 2(TE [p.C1483Y]/[WT])≥2.142605598 and log 2(TE[p.L2427P]/ [WT])≥2.232171262. The 256 selected genes are given in Table 1.

<Example 9> Analysis of eIF4E
Hyperactivation-Sensitive Gene 9-1: Analysis of General 5'-UTR Features 5'-UTRs were obtained from the UCSC Genome Browser (GRCm38/mm10; https://genome.ucsc.edu/) for all genes present on the ribosome profiling. The longest 5'-UTR sequence of individual mRNAs annotated in RefSeq was selected for analysis.

mRNAs of the 256 mTOR hyperactivation-sensitive genes in FMCD mice in Table 1 were compared with all detected genes for GC content in 5'-UTR, length, and Gibbs free energy.

Minimum folding $\Delta G°$ was predicted for each sequence using QuikFold2 version 3.0 (http://mfold.ma.albany.edu/ ?q=DINAMelt/Quickfold) set with default parameters of RNA folding energy rules (Lee J H et al. De novo somatic mutations in components of the PI3K-AKT3-mTOR pathway cause hemimegalencephaly Nat. Genet. 2012; 44(8): 941-945).

9-2: Common Motif in eIF4E Hyperactivation-Sensitive Genes

Multiple Em for motif elicitation (MEME, http://meme-suite.org/tools/meme) was performed using the MEME browser application program (version 4.12.0) (Bailey T L, Elkan C. Fitting a mixture model by expectation maximization to discover motifs in biopolymers. Proc. Second Int. Conf. Intell. Syst. Mol. Biol. 1994; 28-36). 5'-UTRs were called from the UCSC Genome Browser (GRCm38/mm10), and RefSeq-annotated mRNAs with known 5'-UTRs were selected for further analysis. The longest 5'-UTR for each gene was compiled for input into MEME as a training set.

For eIF4E activation-sensitive genes in the FMCD models of Table 1, motif search parameters for a 12-nt sequence with any number of repeats using only a given strand was employed to identify guanine quartet (GGC)$_4$, CERT, A-rich, and U-rich motifs.

For the FMCD mice, eIF4E activation-sensitive genes in FMCD with RefSeq-annotated mRNAs containing known 5'-U IRs were evaluated for the presence of guanine quartet (GGC)$_4$, CERT, A-rich, and U-rich motifs using Find Individual Motif Occurrences (FIMO; http://meme-suite.org/ tools/fimo).

Figure 32:
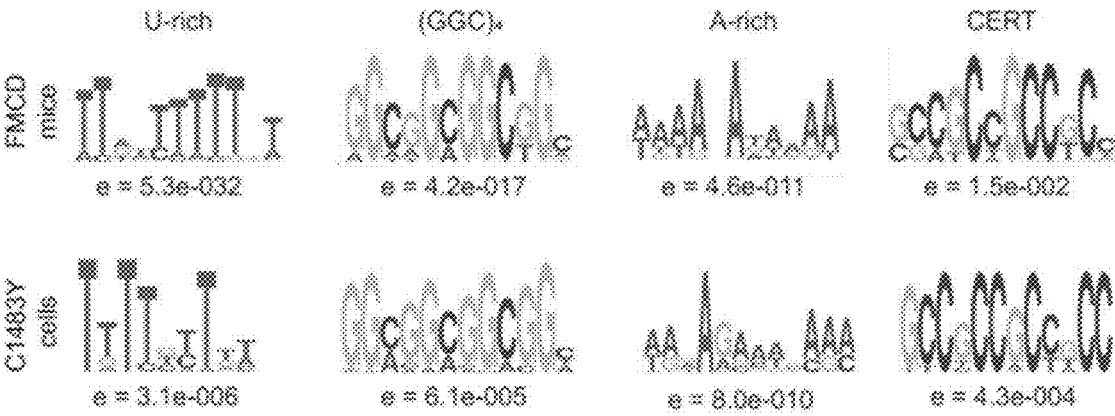
FIG. 32 shows 5'-UTR consensus sequences (motifs) in eIF4E activation-sensitive genes wherein U-rich, guanine quartet $(GGC)_4$, A-rich, and cytosine enriched regulator of translation (CERT) motifs are enriched in the eIF4E activation-sensitive genes, as analyzed by Multiple Em for motif elicitation (MEME) analysis, with statistical significance. Among all eIF4E activation-sensitive genes, percentages of genes containing U-rich, guanine quartet $(GGC)_4$, A-rich, and CERT motifs are given.
Figure 33:
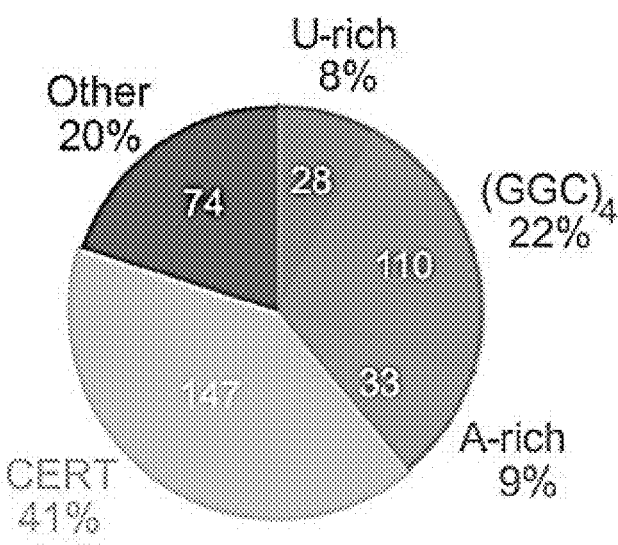
FIG. 33 is a diagram illustrating frequencies of mTOR activation-sensitive genes containing 5'-UTR motifs in FMCD mice according to an embodiment of the present disclosure.

The MEME analysis results indicate that the eIF4E hyperactivation-sensitive genes have 5'-UTR specific motifs in common (FIGS. 32 and 33).

As can be seen in FIG. 32, the eIF4E activation-sensitive genes provide novel mTOR-responsive 5'-UTR motifs with consensus sequences present in 5'-UTR Consensus sequence and enrichment values (E-values) of the U-rich, guanine quartet (GGC)$_4$, A-rich, and CERT motifs identified in 256 eIF4E activation-sensitive genes in FMCD mice of Table 1 were identified by MEME analysis.

FIG. 33 is a diagram illustrating frequencies of mTOR activation-sensitive genes containing U-rich, guanine quartet, A-rich, and CERT motifs in FMCD mice, wherein given to the same gene, two or more motifs were counted independently. As a result, genes with the 5'-UTR motifs accounted for 80% of mTOR hyperactivation-sensitive genes.

9-3: 5'-UTR Luciferase Reporter Assay

5'-UTRs were obtained from the UCSC Genome Browser (GRCm38/mm10). 5'-UTRs with WT, transversion, and deletion sequences were synthesized for each of ADK-S, CREB1, and IRSp53.

In Table 8, underlined letters in bold on the ADK-S wild-type (WT) sequence stand for guanine quartet (GGC)$_4$; the first and third marks in underlined letters in bold on the CREB1 wild-type sequence stands for A-rich and U-rich motifs, respectively; and the underlined letters in bold on the IRSp53 wild-type sequence stand for a U-rich motif. In the Type, Deletion indicates sequences resulting from deleting each motif from WT.

TABLE 8

| Gene/Type | Strand type (SEQ ID NO) | Sequence |
|---|---|---|
| ADK-S-WT | Sense (SEQ ID NO: 220) | GGGCCGCCCGCGCGCGGGGTGTGTAAGGACGAG CTCTCCGACGCTGAGTGCCAGAGCTAGGGAGCAG TTGCTGTGGTACCTACTGCTACCTGGGCAGACGC TGAGCATCGGACATCAGGCGCGGGGCGCTGCGG TGCGGGACGGGTAGGTGCAGTC |
| | Antisense (SEQ ID NO: 221) | GACTGCACCTACCCGTCCCGCACCGCAGCGCCCC GCGCCTGATGTCCGATGCTCAGCGTCTGCCCAGG TAGCAGTAGGTACCACAGCAACTGCTCCCTAGCT CTGGCACTCAGCGTCGGAGAGCTCGTCCTTACAC ACCCCGCGCGCGGGCGGCCC |
| ADK-S-Deletion | Sense (SEQ ID NO: 222) | GGGCCGCCCGCGCGCGGGGTGTGTAAGGACGAG CTCTCCGACGCTGAGTGCCAGAGCTAGGGAGCAG TTGCTGTGGTACCTACTGCTACCTGGGCAGACGC TGAGCATCCGCTGCTGCAGTC |
| | Antisense (SEQ ID NO: 223) | GACTGCAGCAGCGGATGCTCAGCGTCTGCCCAGG TAGCAGTAGGTACCACAGCAACTGCTCCCTAGCT CTGGCACTCAGCGTCGGAGAGCTCGTCCTTACAC ACCCCGCGCGCGGGCGGCCC |
| CREB1-WT | Sense (SEQ ID NO: 224) | TCGGCACTGGGCGGCGCTGGCTGGCTCCCTGG CTGCGGCTCCTCAGTCGGCGGCGGCTGCTGCTG CCTGTGGCCCGGGCGGCTGGGAGAAGCGGAGTG TTGGTGAGTGACGCGGCGGAGGTGTAGTTTGACG CGGTGTGTTACGTGGGGGAGAGAATAAAACTCC AGCGAGATCCGGGCCGCGAACGAAAGCAGTGAC GGAGGAGCTTGTACCACCGGTATCC |
| | Antisense (SEQ ID NO: 225) | GGATACCGGTGGTACAAGCTCCTCCGTCACTGCT TTCGTTCGCGGCCCGGATCTCGCTGGAGTTTTATT CTCTCCCCCACGTAACACACCGCGTCAAACTACA CCTCCGCCGCGTCACTCACCAACACTCCGCTTCTC CCAGCCGCCCGGGCCACAGGCAGCAGCAGCCGC CGCCGACTGAGGAGCCGCAGCCAGGGAGCCAGC CAGCGCCGCCCAGTGCCGA |
| CREB1-Deletion1 | Sense (SEQ ID NO: 226) | TCCTGGCTCCCTGGCTGCGGCTCCTCAGTCGGCG GCGGCTGCTGCTGCCTGTGGCCCGTGAGTGACGC GGCGGAGGTGTAGTTTGACGCGGTGTGTTACGTG GGGGAGAGAATAAAACTCCAGCGAGATCCGGGC CGCGAACGAAAGCAGTGACGGAGGAGCTTGTAC CACCGGTATCC |
| | Antisense (SEQ ID NO: 227) | GGATACCGGTGGTACAAGCTCCTCCGTCACTGCT TTCGTTCGCGGCCCGGATCTCGCTGGAGTTTTATT CTCTCCCCCACGTAACACACCGCGTCAAACTACA CCTCCGCCGCGTCACTCACGGGCCACAGGCAGCA GCAGCCGCCGCCGACTGAGGAGCCGCAGCCAGG GAGCCAGGA |
| CREB1-Deletion2 | Sense (SEQ ID NO: 228) | TCGGCACTGGGCGGCGCTGGCTGGCTCCCTGGCT GCGGCTCCTCAGTCGGCGGCGGCTGCTGCTGCCT GTGGCCCGGGCGGCTGGGAGAAGCGGAGTGTTG GTGAGTGACGCGGCGGAGGTGTAGTTTGACGCGG TGTGTTACGTGGGGGGCTCCAGCGAGATCCGGGCC GCGAACGAAAGCAGTGACGGAGGAGCTTGTACC ACCGGTATCC |
| | Antisense (SEQ ID NO: 229) | GGATACCGGTGGTACAAGCTCCTCCGTCACTGCT TTCGTTCGCGGCCCGGATCTCGCTGGAGCCCCCA CGTAACACACCGCGTCAAACTACACCTCCGCCGC GTCACTCACCAACACTCCGCTTCTCCCAGCCGCCC GGGCCACAGGCAGCAGCAGCCGCCGCCGACTGA GGAGCCGCAGCCAGGGAGCCAGCCAGCGCCGCC CAGTGCCGA |
| CREB1-Deletion3 | Sense (SEQ ID NO: 230) | TCGGCACTGGGCGGCGCTGGCTGGCTCTCATGCT GCCTGTGGCCCGGGCGGCTGGGAGAAGCGGAGT GTTGGTGAGTGACGCGGCGGAGGTGTAGTTTGAC GCGGTGTGTTACGTGGGGGAGAGAATAAAACTCC AGCGAGATCCGGGCCGCGAACGAAAGCAGTGAC GGAGGAGCTTGTACCACCGGTATCC |
| | Antisense (SEQ ID NO: 231) | GGATACCGGTGGTACAAGCTCCTCCGTCACTGCT TTCGTTCGCGGCCCGGATCTCGCTGGAGTTTTATT CTCTCCCCCACGTAACACACCGCGTCAAACTACA CCTCCGCCGCGTCACTCACCAACACTCCGCTTCTC CCAGCCGCCCGGGCCACAGGCAGCATGAGAGCC AGCCAGCGCCGCCCAGTGCCGA |

TABLE 8 -continued

| Gene/Type | Strand type (SEQ ID NO) | Sequence |
|---|---|---|
| IRSp53-WT | Sense (SEQ ID NO: 232) | GTGGTCCTGGTCTGCGCGCCTTTTCCTGTTGCTG CAGTTGTCGCTTTCCTCACCGCCACCCGTGCCCCT GCTCTGGTCTGTGGTGTAGCCGGGACCCAGGACC |
| | Antisense (SEQ ID NO: 233) | GGTCCTGGGTCCCGGCTACACCACAGACCAGAGC AGGGGCACGGGTGGCGGTGAGGAAAGCGACAAC TGCAGCAACAGGAAAAGGCGCGCAGACCAGGAC CAC |
| IRSp53-Deletion | Sense (SEQ ID NO: 234) | GTGGTCCTGGTCTGCGCGCCAGTTGTCGCTTTCCT CACCGCCACCCGTGCCCCTGCTCTGGTCTGTGGTG TAGCCGGGACCCAGGACC |
| | Antisense (SEQ ID NO: 235) | GGTCCTGGGTCCCGGCTACACCACAGACCAGAGC AGGGGCACGGGTGGCGGTGAGGAAAGCGACAAC TGGCGCGCAGACCAGGACCAC |

The synthesized 5'-UTR was cloned into a site between the SV40 promoter and the firefly luciferase open reading frame in the pGL3-promoter vector (Promega, E1761), using HindIII (NEB, R3104) and NcoI (NEB, R3193). *Renilla* pGL4.74 was used as a control reporter. HEK293T cells were co-transfected with a mixture of 30:30:1 of pGL3-SV40 5'-UTR reporter; FLAG-tagged mTOR WT, FLAG-tagged mTOR p.Cys1483Tyr, or FLAG-tagged mTOR p.Leu2427Pro; and pGL4.74 control reporter, using iNfect transfection reagent. Cells were harvested 24 hours after transfection and lysed. The cell lysate was measured for luciferase activity using a Dual Luciferase Assay kit (Promega, E1960). Firefly luciferase activity was normalized to *Renilla* activity and was expressed as values relative to HEK293T cells transfected with FLAG-tagged mTOR WT.

Figure 34A:
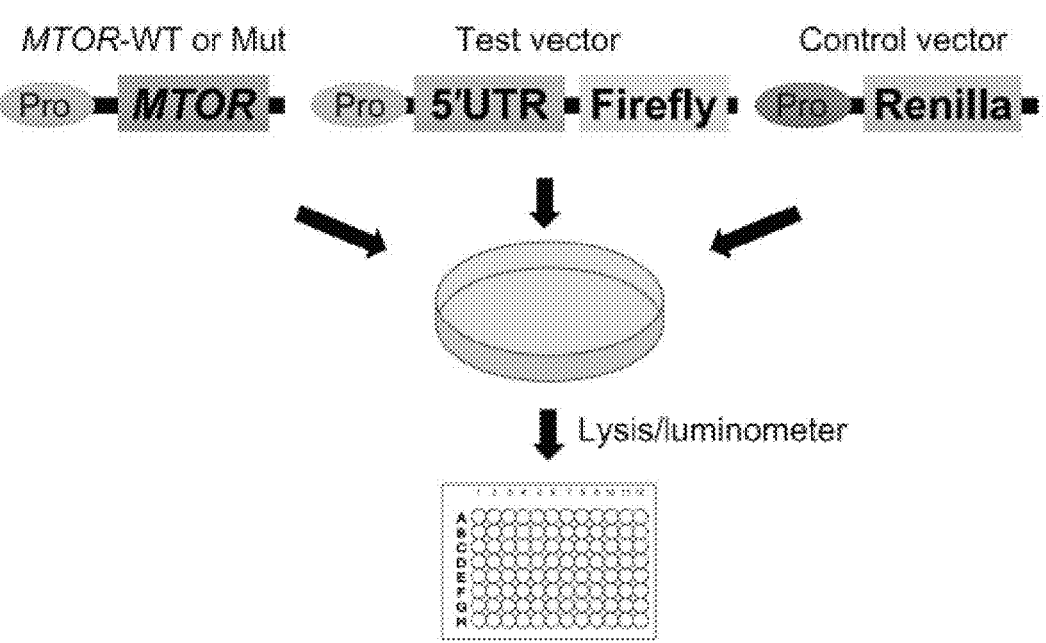
FIGS. 34a and 34b shows the increased expression of eIF4E activation-sensitive genes with 5'-UTR region by mTOR-activating mutation. When the 5'-UTRs of the eIF4E activation-sensitive genes Adk-S, Adk-L, Creb1, and IRSp53 are located upstream of the luciferase gene, the expression of luciferase was increased in response to somatic activating mutations in mTOR The mTOR activating mutations were mTOR p.C1483Y and mTOR p.L2427P while mTOR WT was used as a control. mTOR WT, mTOR p.C1483Y, and mTOR p.L2427P were expressed in HEK293T cells. In the figures, Pro stands for promoter, Actb for β-actin gene, and pGL3 for an empty vector lacking a 5'-UTR. Results are normalized to the luciferase activity in mTOR WT transfected cells.
Figure 34B:
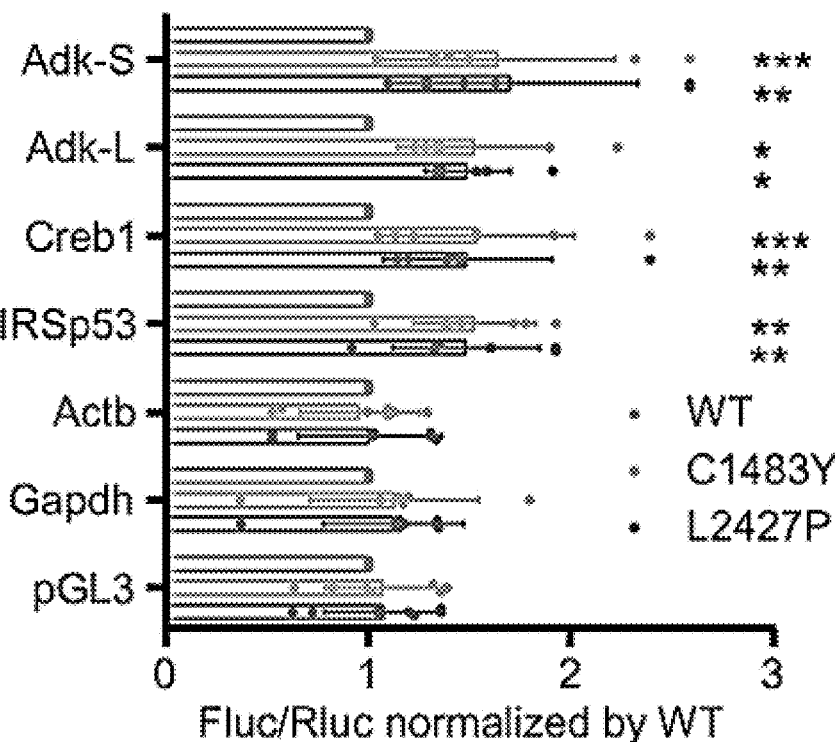

FIGS. 34*a* and 34*b* shows 5'-UTR motif-mediated translation upregulation in eIF4E activation-sensitive genes. In detail, when the 5'-UTRs of the eIF4E activation-sensitive genes Adk-S, Adk-L, Creb1, and IRSp53 are located upstream of the luciferase gene, the expression of luciferase was increased in response to somatic activating mutations in mTOR. The mTOR activating mutations were mTOR p.C1483Y and mTOR p.L2427P while mTOR WT was used as a control. mTOR WT, mTOR p.C1483Y, and mTOR p.L2427P were expressed in HEK293T cells. In the figures, Pro stands for promoter, Actb for β-actin gene, and pGL3 for an empty vector lacking a 5'-UTR Results are normalized to the luciferase activity in transfected mTOR WT cells.

FIG. 34*b* shows 5'-UTR motif-mediated expression upregulation. 5'-UTR-mediated translation of target mRNAs (ADK-S, ADK-L, CREB1, and IRSp53) and control mRNAs (ACTB and GAPDH) was conducted and results were analyzed by 5'-UTR luciferase reporter assay in mTOR WT (WT)- and mTOR p.C1483Y (p.C1483Y)-transfected HEK293T cells, or mTOR WT (WT)- and p.L2427P (p.L2427P)-transfected HEK293T cells.

In FIG. 34*a*, Pro denote promoter, Actb denotes, β-actin gene, and pGL3 denotes the test vector lacking a 5'-UTR. Analysis results normalized to 5'-UTR reporter activity in the transfected mTOR-WT cells. FIG. 34*b* shows quantification of results obtained in FIG. 34*a*.

Figure 35:
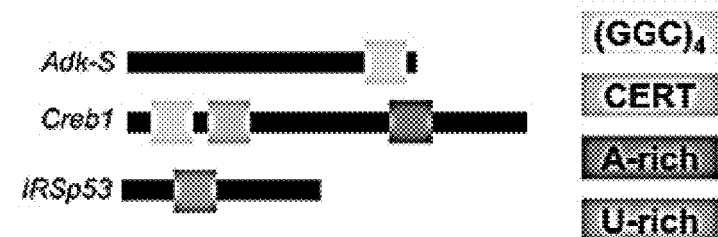
FIG. 35 shows a difference in expression levels of eIF4E activation-sensitive genes depending on the presence or absence of the 5'-UTR motifs, wherein locations of 5'-UTR motifs in Adk-S, IRSp53, and Creb1 are indicated. Deletion of the 5'-motifs from each of the eIF4E hyperactivation-sensitive genes reversed the increased expression of the genes in response to mTOR mutation, implying that the increased translation of eIF4E activation-sensitive genes in response to mTOR activating mutation relies on 5-UTR motifs of the corresponding genes.
Figure 35:
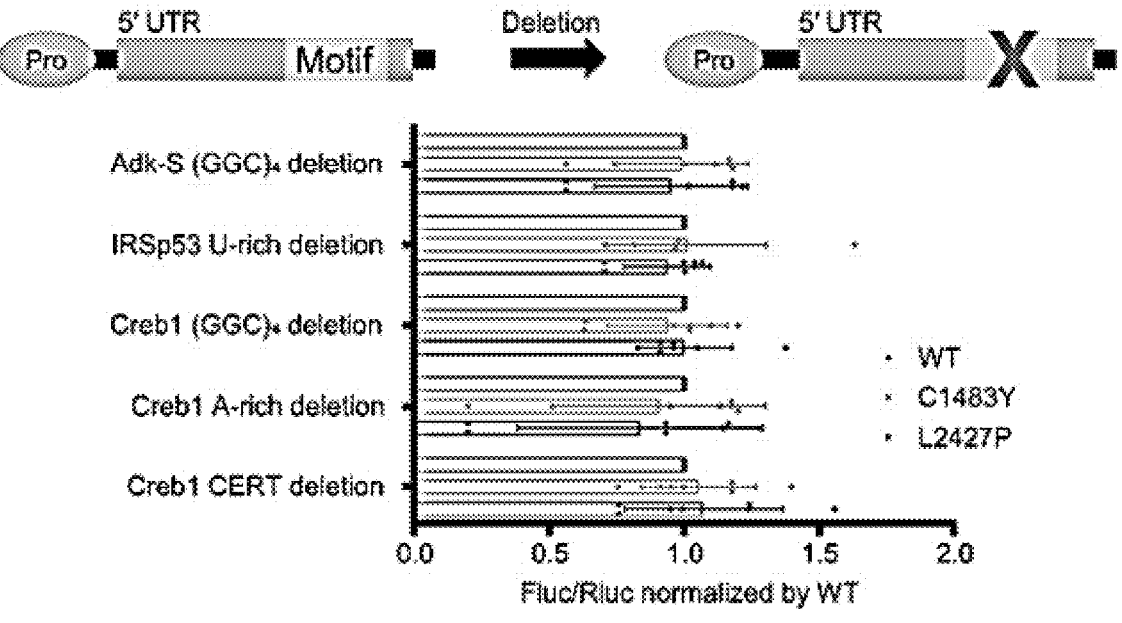

As can be understood from the data of FIG. 35, deletion of the specific motifs from the eIF4E hyperactivation-sensitive genes reversed the increased expression of the genes in response to mTOR mutation and eIF4E hyperactivation. From FIG. 35, it is observed that the eIF4E activation-sensitive genes provide novel eIF4E-responsive 5'-UTR motif and different expression levels were measured depending on the presence or absence of the 5'-UTR motifs. In the upper panel of FIG. 35, locations of 5'-UTR motifs in Adk-S, IRSp53, and Creb1 are indicated. The graph in the lower panel of FIG. 35 shows effects of deletion mutations in 5'-UTR motif domains in Adk-S, IRSp53, and Creb1 on 5'-UTR luciferase reporter activity in mTOR-activated (mTOR p.C1483Y [p.C1483Y] or p.L2427P [p.L2427P]) cells relative to mTOR WT (WT)-transfected HEK293T cells. In the figure, Pro denotes promoter.

<Example 10> Repeated Dose Toxicity Assay

ASO #16, #21, #27, #35, #75, #77, and #89 selected in Example 4 were each assayed for repeated dose toxicity by subcutaneous injection.

Repeated dose toxicity assay of the MO sequences was conducted by Biotoxtech Co., Ltd. In repeated dose toxicity assay, each ASO sequence was subcutaneously injected at a dose of 100 mg/kg to groups of four male mice seven times in total within a month (days 1, 3, 5, 7, 14, 21, and 28). Two days after the last injection, histopathologic observations were made.

No dead or moribund animals were observed in ASO #16, #21, #27, #35, #75, and #77 test groups whereas all animals in the ASO #89 test group were dead or in a moribund state. Except for ASO #89 test group, all the test groups were free of behavioral abnormality.

The toxicity of ASO #89 might be attributed to the sequence thereof other than the 2'-MOE gapmer chemically modified structure typically known, or might result from effect on the expression of off-target genes other than the target gene. The in-silico off-target gene analysis in Example 4-4 revealed that ASO #16, #21, #27, #35, #75, and #77, which each target eIF4E, are free of off-target genes coincident with the remaining 19 nucleotide sequences except for 1 nucleotide sequence whereas there are four off-target genes for ASO #89.

The invention claimed is:

1. A method for prevention, alleviation, or treatment of a disease associated with an increased activity or an increased expression level of eukaryotic translation initiation factor 4E (eIF4E) in brain neuronal cells, comprising administering an eIF4E inhibitor to a subject in need thereof, wherein the eIF4E inhibitor is one or more antisense oligonucleotides, wherein the one or more antisense oligonucleotides hybridizes to a nucleotide sequence encoding eIF4E, wherein each of the one or more antisense oligonucleotides consists of a nucleotide sequence selected from the group consisting of SEQ ID NOs: 16, 27, 35, and 182, wherein the disease is Focal Malformations of Cortical Development (FMCD) caused by mTOR hyperactivation, and wherein nucleotides at positions 1 to 5 and 16 to 20 in the 5' to 3' direction of each of the one or more antisense oligonucleotides include a 2'-O-methoxyethyl ribose, nucleotides at positions 6 to 15 include a 2-deoxyribose, all internucleoside linkages are phosphorothioate bonds, and all cytosine residues are 5-methylcytosine.

2. The method of claim 1, wherein the FMCD is focal cortical dysplasia (FCD), hemimegalencephaly (HME), or Tuberous sclerosis complex (TSC).

3. The method of claim 1, wherein the mTOR hyperactivation is caused by a brain somatic mutation.

4. The method of claim 1, wherein the method alleviates at least one symptom of the FMCD selected from the group consisting of epilepsy, anxiety, cognitive impairment, short-term memory impairment, motor impairment, social behavior disorder, repetitive behavior disorder, depression, spontaneous seizure, behavioral seizure or electroencephalogram seizure.

5. The method of claim 1, wherein the one or more antisense oligonucleotides suppress increased expression of an eIF4E activation-sensitive gene, or decreases expression of an eIF4E activation-sensitive gene, wherein the eIF4E activation-sensitive gene includes, at a 5'-untranslated region, at least one motif selected from the group consisting of a U-rich motif, a guanine quartet motif, an A-rich motif, and a CERT motif.

6. The method of claim 5, wherein the eIF4E activation-sensitive gene is adenosine kinase (ADK), cAMP responsive element binding protein 1 (CREB1) or insulin receptor substrate p53 (IRSp53).

7. The method of claim 1, wherein the FMCD is a focal cortical dysplasia type II (FCD type II).

8. An antisense oligonucleotide wherein the antisense oligonucleotide inhibits expression or activity of eIF4E,
- wherein the antisense oligonucleotide hybridizes to a nucleotide sequence encoding eIF4E,
- wherein the antisense oligonucleotide comprises an oligonucleotide selected from the group consisting of SEQ ID NOs: 16, 27, 35, 143, 149, 182 and 184, and
- wherein the antisense oligonucleotide comprises at least one chemical modification selected from the group consisting of a chemically-modified inter-nucleoside linkage, a chemically-modified sugar moiety, and a chemically-modified nucleobase.

9. The antisense oligonucleotide of claim 8, wherein the expression level of eIF4E measured in the presence of a control oligonucleotide consisting of SEQ ID NO: 201 is defined as 100%, and the antisense oligonucleotide decreases the expression level of eIF4E to 90% or less relative to the control expression level.

10. The antisense oligonucleotide of claim 8, wherein at least one nucleotide included in the antisense oligonucleotide comprises at least one chemical modification selected from the group consisting of 2'-O-methoxyethyl ribose, CET ribose and a locked nucleic acid.

11. The antisense oligonucleotide of claim 10, wherein one to six nucleotides at each end of the antisense oligonucleotide comprise at least one chemical modification selected from the group consisting of 2'-O-methoxyethyl ribose, cET ribose and a locked nucleic acid.

12. The antisense oligonucleotide of claim 8, wherein the antisense oligonucleotide comprises at least one chemically-modified inter-nucleoside linkage.

13. The antisense oligonucleotide of claim 8, wherein the chemically-modified inter-nucleoside linkage is a phosphorothioate bond, the chemically-modified sugar moiety is 2'-O-methoxyethyl ribose, and the chemically-modified nucleobase is 5-methylcytosine.

14. The antisense oligonucleotide of claim 8, wherein the antisense oligonucleotide comprises a phosphorothioate bond, 2'-O-methoxyethyl ribose and 5-methylcytosine.

* * * * *

SEQUENCE LISTING

<160> NUMBER OF SEQ ID NOS: 235

<210> SEQ ID NO 1
<211> LENGTH: 20

-continued

```
<212> TYPE: DNA
<213> ORGANISM: Artificial Sequence
<220> FEATURE:
<223> OTHER INFORMATION: Antisense oligonucleotide

<400> SEQUENCE: 1
aaacaaagat agccacatca                                             20

<210> SEQ ID NO 2
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 2
tcaaactagt gctccaaact                                             20

<210> SEQ ID NO 3
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 3
aggacaaatc tagttgtcta                                             20

<210> SEQ ID NO 4
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 4
ggacaaatct agttgtctaa                                             20

<210> SEQ ID NO 5
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 5
agttgtctaa aagacaattc                                             20

<210> SEQ ID NO 6
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 6
ctttccttgt ataccctcct                                             20

<210> SEQ ID NO 7
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 7
```

-continued

```
tttccttgta taccctccta                                        20

<210> SEQ ID NO 8
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 8
aggataggtt ttttttatac                                        20

<210> SEQ ID NO 9
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 9
gataggtttt ttttatacct                                        20

<210> SEQ ID NO 10
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 10
cactgcgcct ggtgtcaaat                                        20

<210> SEQ ID NO 11
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 11
gcctggtgtc aaatattact                                        20

<210> SEQ ID NO 12
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 12
ggcatacata cagggacatg                                        20

<210> SEQ ID NO 13
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 13
gcatacatac agggacatgt                                        20

<210> SEQ ID NO 14
<211> LENGTH: 20
<212> TYPE: DNA
<213> ORGANISM: Artificial Sequence
```

-continued

<220> FEATURE:
<223> OTHER INFORMATION: Antisense oligonucleotide

<400> SEQUENCE: 14
gcttactgtg gtgagagtca                                                    20

<210> SEQ ID NO 15
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 15
cttactgtgg tgagagtcaa                                                    20

<210> SEQ ID NO 16
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 16
aaaccttact gtctctagcc                                                    20

<210> SEQ ID NO 17
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 17
aaccttactg tctctagcca                                                    20

<210> SEQ ID NO 18
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 18
aacagttaag caacaacact                                                    20

<210> SEQ ID NO 19
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 19
acagttaagc aacaacactg                                                    20

<210> SEQ ID NO 20
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 20
ctggataatc aaagctctca                                                    20

-continued

```
<210> SEQ ID NO 21
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 21
tggataatca aagctctcat                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
taagcatacc ttaaaaagtg                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 23
aagcatacct taaaaagtga                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 24
agcatacctt aaaaagtgag                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 25
gcatacctta aaagtgagt                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
cataccttaa aaagtgagta                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense oligonucleotide
```

-continued

```
<400> SEQUENCE: 27
tctccaatat tagatggcag                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 28
ccaatattag atggcagaaa                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 29
aaattattag gccttaaatg                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 30
ttattaggcc ttaaatgtag                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 31
tggttactta cgcccaaaag                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 32
ggttacttac gcccaaaagt                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 33
gttacttacg cccaaaagtc                                              20

<210> SEQ ID NO 34
```

-continued

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 34
ttacttacgc ccaaaagtct                                                20

<210> SEQ ID NO 35
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 35
acttacgccc aaaagtcttc                                                20

<210> SEQ ID NO 36
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 36
ccaagtcagc acggactttt                                                20

<210> SEQ ID NO 37
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 37
caagtcagca cggacttttt                                                20

<210> SEQ ID NO 38
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 38
aagtcagcac ggactttttt                                                20

<210> SEQ ID NO 39
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 39
tccattatga ccaatacttt                                                20

<210> SEQ ID NO 40
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 40
```

-continued ccattatgac caatacttttt                                                        20

<210> SEQ ID NO 41
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 41
cattatgacc aatactttttc                                                        20

<210> SEQ ID NO 42
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 42
ttagaaagct tacctgttct                                                         20

<210> SEQ ID NO 43
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 43
tagaaagctt acctgttctg                                                         20

<210> SEQ ID NO 44
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 44
agaaagctta cctgttctgt                                                         20

<210> SEQ ID NO 45
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 45
tataacaatt acaggaagct                                                         20

<210> SEQ ID NO 46
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 46
aacaattaca ggaagctata                                                         20

<210> SEQ ID NO 47
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 47
catgctcatt tccacttctc                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 48
tacagcgatc tgtaggcctc                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 49
atctgtaggc ctcgctcctc                                             20

<210> SEQ ID NO 50
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 50
ttccctcctc catgacagcc                                             20

<210> SEQ ID NO 51
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 51
aaggcaatac tcaccggttc                                             20

<210> SEQ ID NO 52
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 52
gacagtcgcc atcttagatc                                             20

<210> SEQ ID NO 53
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 53
tagatcgatc tgatcgcaca                                             20
```

-continued

```
<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
tctgatcgca caaccgctcc                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 55
aatgagattc aaaccggatt                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 56
agattcaaac cggattggcc                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 57
ggcttctggg aagtggagtc                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 58
ataaggcttc atttgcttag                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 59
gggtcaacta tgactcttga                                              20

<210> SEQ ID NO 60
<211> LENGTH: 20
<212> TYPE: DNA
<213> ORGANISM: Artificial Sequence
<220> FEATURE:
```

-continued

<223> OTHER INFORMATION: Antisense oligonucleotide

<400> SEQUENCE: 60
actatgactc ttgacgttga                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 61
gactcttgac gttgactcat                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 62
ctccttaggc gagtgactta                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63
gatacactta cctcacaagg                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64
ttacctcaca agggtgtgct                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 65
aaatctagtt gtctaaaaga                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 66
tagttgtcta aaagacaatt                                              20

-continued

```
<210> SEQ ID NO 67
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 67
tctgtaggcc tcgctcctcc                                                20

<210> SEQ ID NO 68
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 68
ctgtaggcct cgctcctccc                                                20

<210> SEQ ID NO 69
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 69
tccctcctcc atgacagccc                                                20

<210> SEQ ID NO 70
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 70
agatgccagc cagggaagcc                                                20

<210> SEQ ID NO 71
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 71
gccagccagg gaagccactc                                                20

<210> SEQ ID NO 72
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 72
tgctatctta tcacctttag                                                20

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide
```

-continued

```
<400> SEQUENCE: 73
ggcgaatgag acttctctta                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 74
tcctggatcc ttcaccaatg                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 75
tgtcatattc ctggatcctt                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 76
tggatccttc accaatgtta                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 77
gatccttcac caatgttaca                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 78
tatcaccttt agctctaaca                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 79
aattactaga caactggata                                              20

<210> SEQ ID NO 80
<211> LENGTH: 20
```

-continued

```
<212> TYPE: DNA
<213> ORGANISM: Artificial Sequence
<220> FEATURE:
<223> OTHER INFORMATION: Antisense oligonucleotide

<400> SEQUENCE: 80
catcttagat cgatctgatc                                            20

<210> SEQ ID NO 81
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 81
ctggatcctt caccaa                                                16

<210> SEQ ID NO 82
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 82
ctatcttatc accttt                                                16

<210> SEQ ID NO 83
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 83
ttactagaca actgga                                                16

<210> SEQ ID NO 84
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 84
atcttagatc gatctg                                                16

<210> SEQ ID NO 85
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 85
ttacttacgc ccaaaa                                                16

<210> SEQ ID NO 86
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 86
```

-continued ttccttgtat accctc                                                16

<210> SEQ ID NO 87
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 87
accttactgt ctctag                                                16

<210> SEQ ID NO 88
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 88
gaaagcttac ctgttc                                                16

<210> SEQ ID NO 89
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 89
ctcttgacgt tgactc                                                16

<210> SEQ ID NO 90
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 90
gtaggcctcg ctcctc                                                16

<210> SEQ ID NO 91
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 91
cattatgacc aatact                                                16

<210> SEQ ID NO 92
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 92
aatattagat ggcaga                                                16

<210> SEQ ID NO 93
<211> LENGTH: 16
<212> TYPE: DNA
<213> ORGANISM: Artificial Sequence -continued
<220> FEATURE:
<223> OTHER INFORMATION: Antisense oligonucleotide

<400> SEQUENCE: 93
ggataatcaa agctct                                                            16

<210> SEQ ID NO 94
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 94
ttactgtggt gagagt                                                            16

<210> SEQ ID NO 95
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 95
ctggtgtcaa atatta                                                            16

<210> SEQ ID NO 96
<211> LENGTH: 8
<212> TYPE: DNA
<213> ORGANISM: Artificial Sequence
<220> FEATURE:
<223> OTHER INFORMATION: ASO Common motif

<400> SEQUENCE: 96 acawyagc                                                                     8

<210> SEQ ID NO 97
<211> LENGTH: 11
<212> TYPE: DNA
<213> ORGANISM: Artificial Sequence
<220> FEATURE:
<223> OTHER INFORMATION: U-rich motif
<220> FEATURE:
<221> NAME/KEY: misc_feature
<222> LOCATION: (10)..(10)
<223> OTHER INFORMATION: n is any nucleotide

<400> SEQUENCE: 97
ttdwtttttn t                                                                 11

<210> SEQ ID NO 98
<211> LENGTH: 12
<212> TYPE: DNA
<213> ORGANISM: Artificial Sequence
<220> FEATURE:
<223> OTHER INFORMATION: guanine quartet

<400> SEQUENCE: 98
ggcggcggcg gc                                                                12

<210> SEQ ID NO 99
<211> LENGTH: 11
<212> TYPE: DNA
<213> ORGANISM: Artificial Sequence
<220> FEATURE:
<223> OTHER INFORMATION: A-rich motif
<220> FEATURE:

-continued

```
<221> NAME/KEY: misc_feature
<222> LOCATION: (5)..(5)
<223> OTHER INFORMATION: n is any nucleotide

<400> SEQUENCE: 99
aaaanataaa a                                                          11

<210> SEQ ID NO 100
<211> LENGTH: 12
<212> TYPE: DNA
<213> ORGANISM: Artificial Sequence
<220> FEATURE:
<223> OTHER INFORMATION: CERT motif

<400> SEQUENCE: 100
gccgccgccg cc                                                         12

<210> SEQ ID NO 101
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 101
ccatcttaga tcgatctgat                                                 20

<210> SEQ ID NO 102
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 102
atcttagatc gatctgatcg                                                 20

<210> SEQ ID NO 103
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 103
acgtgacgga tatgtccgtt                                                 20

<210> SEQ ID NO 104
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 104
tgccaggcaa gcctactgtg                                                 20

<210> SEQ ID NO 105
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 105
gaagttctgt gcaaccgttc                                                 20
```

```
<210> SEQ ID NO 106
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 106
agttctgtgc aaccgttcca                                                20

<210> SEQ ID NO 107
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 107
gaaatagcct aagtccagat                                                20

<210> SEQ ID NO 108
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 108
tagcctaagt ccagatgcca                                                20

<210> SEQ ID NO 109
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 109
caactatgac tcttgacgtt                                                20

<210> SEQ ID NO 110
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 110
aggtgatgat acacttacct                                                20

<210> SEQ ID NO 111
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 111
gactctagaa atgattcata                                                20

<210> SEQ ID NO 112
<211> LENGTH: 20
<212> TYPE: DNA
<213> ORGANISM: Artificial Sequence
<220> FEATURE:
```

<223> OTHER INFORMATION: Antisense oligonucleotide

<400> SEQUENCE: 112
actaaacctg aactgatatg                                                                20

<210> SEQ ID NO 113
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 113
aacctgaact gatatgctga                                                                20

<210> SEQ ID NO 114
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 114
ctatcgtaac ctaaaagttc                                                                20

<210> SEQ ID NO 115
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 115
tattttcaat ggaacctaac                                                                20

<210> SEQ ID NO 116
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 116
gtatttgtga aacgtaagca                                                                20

<210> SEQ ID NO 117
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 117
attcaggctt acatattgta                                                                20

<210> SEQ ID NO 118
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 118
acgtgttcgg tcaatgctac                                                                20

```
<210> SEQ ID NO 119
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 119
tcggtcaatg ctacagcacc                                                    20

<210> SEQ ID NO 120
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 120
tcatatatca atcatgattc                                                    20

<210> SEQ ID NO 121
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 121
actggattac taaagagttg                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 122
gattactaaa gagttgtgat                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 123
ccaggcctaa aacttggatg                                                    20

<210> SEQ ID NO 124
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 124
ggcctaaaac ttggatgaat                                                    20

<210> SEQ ID NO 125
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 125
tacatacgtt gaacattatg                                          20

<210> SEQ ID NO 126
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 126
cgtttatgat gtaagcacta                                          20

<210> SEQ ID NO 127
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 127
agttcagctt taatccaatc                                          20

<210> SEQ ID NO 128
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 128
ggagataggt tttccacatt                                          20

<210> SEQ ID NO 129
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 129
ataggttttc cacattagac                                          20

<210> SEQ ID NO 130
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 130
agaaacacga cctactggag                                          20

<210> SEQ ID NO 131
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 131
ttagattccg ttttctcctc                                          20

<210> SEQ ID NO 132
<211> LENGTH: 20
```

<212> TYPE: DNA
<213> ORGANISM: Artificial Sequence
<220> FEATURE:
<223> OTHER INFORMATION: Antisense oligonucleotide

<400> SEQUENCE: 132
agattccgtt ttctcctctt                                        20

<210> SEQ ID NO 133
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 133
ttttctcctc ttctgtagtc                                        20

<210> SEQ ID NO 134
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 134
tctcctcttc tgtagtcggg                                        20

<210> SEQ ID NO 135
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 135
cctcttctgt agtcggggga                                        20

<210> SEQ ID NO 136
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 136
cttctgtagt cgggggatta                                        20

<210> SEQ ID NO 137
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 137
tgtagtcggg ggattaggag                                        20

<210> SEQ ID NO 138
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 138

-continued agtcggggga ttaggagtag                                                          20

<210> SEQ ID NO 139
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 139
ggtgattgcc actagccaaa                                                          20

<210> SEQ ID NO 140
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 140
cggaattcac agaaatgacg                                                          20

<210> SEQ ID NO 141
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 141
gcttcaaagt catcaatacg                                                          20

<210> SEQ ID NO 142
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 142
agtcattggc tgcaagatcc                                                          20

<210> SEQ ID NO 143
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 143
ttcatctgcc actgtaagcc                                                          20

<210> SEQ ID NO 144
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 144
taagcagtgt atgatgttaa                                                          20

<210> SEQ ID NO 145
<211> LENGTH: 20
<212> TYPE: DNA
<213> ORGANISM: Artificial Sequence -continued

```
<220> FEATURE:
<223> OTHER INFORMATION: Antisense oligonucleotide

<400> SEQUENCE: 145
gttaaactat ataagactgc                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 146
atataagact gcctctaacg                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 147
cctcaacctt agcatatcta                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 148
tagcatatct aaaactagtc                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 149
gacatcttgc ttcatttgac                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 150
gtaatataga gtttaggtgc                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 151
tagagtttag gtgcttacat                                              20
```

<210> SEQ ID NO 152
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 152
agtttaggtg cttacatata                                                                    20

<210> SEQ ID NO 153
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 153
cgatgactta gttgcttgcc                                                                    20

<210> SEQ ID NO 154
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 154
cttagttgct tgcctgaagg                                                                    20

<210> SEQ ID NO 155
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 155
cacaaatata gtttaggtga                                                                    20

<210> SEQ ID NO 156
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 156
atagtttagg tgagacaacc                                                                    20

<210> SEQ ID NO 157
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 157
atgagcagaa tatcttgagg                                                                    20

<210> SEQ ID NO 158
<211> LENGTH: 20
<212> TYPE: DNA
<213> ORGANISM: Artificial Sequence
<220> FEATURE:
<223> OTHER INFORMATION: Antisense oligonucleotide -continued

<400> SEQUENCE: 158
ttagataact gctaggtaat                                          20

<210> SEQ ID NO 159
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 159
gaggttgatc aaagtataat                                          20

<210> SEQ ID NO 160
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 160
tactagacaa ctggatatgg                                          20

<210> SEQ ID NO 161
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 161
tagacaactg gatatggttg                                          20

<210> SEQ ID NO 162
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 162
acaactggat atggttgtac                                          20

<210> SEQ ID NO 163
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 163
actggatatg gttgtacaga                                          20

<210> SEQ ID NO 164
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 164
gcatgacatt gcagaattag                                          20

<210> SEQ ID NO 165

-continued

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 165
agactggata atcaaagctc                                                    20

<210> SEQ ID NO 166
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 166
gactggataa tcaaagctct                                                    20

<210> SEQ ID NO 167
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 167
aagcgatcga ggtcacttcg                                                    20

<210> SEQ ID NO 168
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 168
cgatcgaggt cacttcgtct                                                    20

<210> SEQ ID NO 169
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 169
tcgaggtcac ttcgtctctg                                                    20

<210> SEQ ID NO 170
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 170
aggtcacttc gtctctgctg                                                    20

<210> SEQ ID NO 171
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 171
```

-continued

```
gtcacttcgt ctctgctgtt                                        20

<210> SEQ ID NO 172
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 172
tttgcataga aactaaaggc                                        20

<210> SEQ ID NO 173
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 173
atagaaacta aaggcagttt                                        20

<210> SEQ ID NO 174
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 174
ttggcagtta atgtcatggc                                        20

<210> SEQ ID NO 175
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 175
gcagttaatg tcatggcaga                                        20

<210> SEQ ID NO 176
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 176
tgctctgctg ctgcttatat                                        20

<210> SEQ ID NO 177
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 177
tgtcttgtaa agccagaagt                                        20

<210> SEQ ID NO 178
<211> LENGTH: 20
<212> TYPE: DNA
```

-continued

```
<213> ORGANISM: Artificial Sequence
<220> FEATURE:
<223> OTHER INFORMATION: Antisense oligonucleotide

<400> SEQUENCE: 178
ctctaacatt aacaacagcg                                              20

<210> SEQ ID NO 179
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 179
aacattaaca acagcgccac                                              20

<210> SEQ ID NO 180
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 180
ttaacaacag cgccacatac                                              20

<210> SEQ ID NO 181
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 181
acaacagcgc cacatacatc                                              20

<210> SEQ ID NO 182
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 182
agcgccacat acatcatcac                                              20

<210> SEQ ID NO 183
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 183
gacctgtatc acatgcatac                                              20

<210> SEQ ID NO 184
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 184
ctgtatcaca tgcatactta                                              20
```

```
<210> SEQ ID NO 185
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 185
tttcaagtaa gacatgactc                                              20

<210> SEQ ID NO 186
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 186
agtaagacat gactctattg                                              20

<210> SEQ ID NO 187
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 187
tgagataaag ctgacaaggt                                              20

<210> SEQ ID NO 188
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 188
taaagctgac aaggtttcag                                              20

<210> SEQ ID NO 189
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 189
ttaatgaaaa ttatacgtag                                              20

<210> SEQ ID NO 190
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 190
aaattatacg tagtaaacac                                              20

<210> SEQ ID NO 191
<211> LENGTH: 20
<212> TYPE: DNA
<213> ORGANISM: Artificial Sequence
<220> FEATURE:
```

<223> OTHER INFORMATION: Antisense oligonucleotide

<400> SEQUENCE: 191
caaccttcat aaaagtacta                                              20

<210> SEQ ID NO 192
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 192
tgccacttga tactgctgaa                                              20

<210> SEQ ID NO 193
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 193
agtttctaga cacgtacaag                                              20

<210> SEQ ID NO 194
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 194
actttacttg gacaatcata                                              20

<210> SEQ ID NO 195
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 195
cttttgaatg caactttagc                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 196
tatgtacagt atgctgagat                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 197
ctaagactga atgactgtgc                                              20

-continued

```
<210> SEQ ID NO 198
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 198
actgtgcctt actttataaa                                                20

<210> SEQ ID NO 199
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 199
cactgatttg aatgaaatgc                                                20

<210> SEQ ID NO 200
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 200
ccaaatctcg attgcttgac                                                20

<210> SEQ ID NO 201
<211> LENGTH: 20
<212> TYPE: DNA
<213> ORGANISM: Artificial Sequence
<220> FEATURE:
<223> OTHER INFORMATION: scrambled ASO-1

<400> SEQUENCE: 201
ctcagtaaca gtgacaccag                                                20

<210> SEQ ID NO 202
<211> LENGTH: 21
<212> TYPE: DNA
<213> ORGANISM: Artificial Sequence
<220> FEATURE:
<223> OTHER INFORMATION: shScramble

<400> SEQUENCE: 202
cgattgatct ctaagtttga t                                              21

<210> SEQ ID NO 203
<211> LENGTH: 63
<212> TYPE: DNA
<213> ORGANISM: Artificial Sequence
<220> FEATURE:
<223> OTHER INFORMATION: sheIF4E sense strand

<400> SEQUENCE: 203
tcgattgatc tctaagtttg atttcaagag aatcaaactt agagatcaat cgttttttct   60
cga                                                                  63

<210> SEQ ID NO 204
<211> LENGTH: 63
<212> TYPE: DNA
<213> ORGANISM: Artificial Sequence
<220> FEATURE:
```

-continued

<223> OTHER INFORMATION: sheIF4E anti-sense strand

<400> SEQUENCE: 204
tcgagaaaaa acgattgatc tctaagtttg attctcttga aatcaaactt agagatcaat        60
cga                                                                       63

<210> SEQ ID NO 205
<211> LENGTH: 19
<212> TYPE: DNA
<213> ORGANISM: Artificial Sequence
<220> FEATURE:
<223> OTHER INFORMATION: shScramble

<400> SEQUENCE: 205
ggaatctcat tcgatgcat                                                       19

<210> SEQ ID NO 206
<211> LENGTH: 59
<212> TYPE: DNA
<213> ORGANISM: Artificial Sequence
<220> FEATURE:
<223> OTHER INFORMATION: shScramble sense strand

<400> SEQUENCE: 206
tggaatctca ttcgatgcat ttcaagagaa tgcatcgaat gagattcctt ttttctcga         59

<210> SEQ ID NO 207
<211> LENGTH: 59
<212> TYPE: DNA
<213> ORGANISM: Artificial Sequence
<220> FEATURE:
<223> OTHER INFORMATION: shScramble anti-sense strand

<400> SEQUENCE: 207
tcgagaaaaa aggaatctca ttcgatgcat tctcttgaaa tgcatcgaat gagattcca         59

<210> SEQ ID NO 208
<211> LENGTH: 36
<212> TYPE: DNA
<213> ORGANISM: Artificial Sequence
<220> FEATURE:
<223> OTHER INFORMATION: Forward primer for sheIF4E

<400> SEQUENCE: 208
ggccgaggcc tcctgggccc gctctagaga tccgac                                   36

<210> SEQ ID NO 209
<211> LENGTH: 24
<212> TYPE: DNA
<213> ORGANISM: Artificial Sequence
<220> FEATURE:
<223> OTHER INFORMATION: Reverse primer for sheIF4E

<400> SEQUENCE: 209
cgagtactag gatccattag gcgg                                                 24

<210> SEQ ID NO 210
<211> LENGTH: 17
<212> TYPE: DNA
<213> ORGANISM: Artificial Sequence
<220> FEATURE:
<223> OTHER INFORMATION: EIF4E forward primer

<400> SEQUENCE: 210
tggcgactgt cgaaccg                                                         17

-continued

<210> SEQ ID NO 211
<211> LENGTH: 26
<212> TYPE: DNA
<213> ORGANISM: Artificial Sequence
<220> FEATURE:
<223> OTHER INFORMATION: EIF4E reverse primer

<400> SEQUENCE: 211
agattccgtt ttctcctctt ctgtag                                          26

<210> SEQ ID NO 212
<211> LENGTH: 23
<212> TYPE: DNA
<213> ORGANISM: Artificial Sequence
<220> FEATURE:
<223> OTHER INFORMATION: GAPDH forward primer

<400> SEQUENCE: 212
gaaggtgaag gtcggagtca acg                                             23

<210> SEQ ID NO 213
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 213
gaagatggtg atgggatttc c                                               21

<210> SEQ ID NO 214
<211> LENGTH: 20
<212> TYPE: DNA
<213> ORGANISM: Artificial Sequence
<220> FEATURE:
<223> OTHER INFORMATION: mismatch ASO

<400> SEQUENCE: 214
gatcctttgt taatgttaca                                                 20

<210> SEQ ID NO 215
<211> LENGTH: 20
<212> TYPE: DNA
<213> ORGANISM: Artificial Sequence
<220> FEATURE:
<223> OTHER INFORMATION: ERBB4 forward primer

<400> SEQUENCE: 215
cagtcagtgt gtgcaggaac                                                 20

<210> SEQ ID NO 216
<211> LENGTH: 20
<212> TYPE: DNA
<213> ORGANISM: Artificial Sequence
<220> FEATURE:
<223> OTHER INFORMATION: ERBB4 reverse primer

<400> SEQUENCE: 216
agcctgtgac ttctcgaaca                                                 20

<210> SEQ ID NO 217
<211> LENGTH: 20
<212> TYPE: DNA
<213> ORGANISM: Artificial Sequence
<220> FEATURE:

<223> OTHER INFORMATION: TTC28 forward primer

<400> SEQUENCE: 217
ctcatgggaa tctgggctct                                                                              20

<210> SEQ ID NO 218
<211> LENGTH: 20
<212> TYPE: DNA
<213> ORGANISM: Artificial Sequence
<220> FEATURE:
<223> OTHER INFORMATION: TTC28 reverse primer

<400> SEQUENCE: 218
tgatgaagct gcctctcgat                                                                              20

<210> SEQ ID NO 219
<211> LENGTH: 20
<212> TYPE: DNA
<213> ORGANISM: Artificial Sequence
<220> FEATURE:
<223> OTHER INFORMATION: scrambled ASO-2

<400> SEQUENCE: 219
taaggctatg aagagatacg                                                                              20

<210> SEQ ID NO 220
<211> LENGTH: 156
<212> TYPE: DNA
<213> ORGANISM: Artificial Sequence
<220> FEATURE:
<223> OTHER INFORMATION: ADK-WT-UTR sense

<400> SEQUENCE: 220
gggccgcccg cgcgcggggt gtgtaaggac gagctctccg acgctgagtg ccagagctag       60
ggagcagttg ctgtggtacc tactgctacc tgggcagacg ctgagcatcg gacatcaggc      120
gcggggcgct gcggtgcggg acgggtaggt gcagtc                                            156

<210> SEQ ID NO 221
<211> LENGTH: 156
<212> TYPE: DNA
<213> ORGANISM: Artificial Sequence
<220> FEATURE:
<223> OTHER INFORMATION: ADK-WT-UTR antisense

<400> SEQUENCE: 221
gactgcacct acccgtcccg caccgcagcg ccccgcgcct gatgtccgat gctcagcgtc       60
tgcccaggta gcagtaggta ccacagcaac tgctccctag ctctggcact cagcgtcgga      120
gagctcgtcc ttacacaccc cgcgcgcggg cggccc                                            156

<210> SEQ ID NO 222
<211> LENGTH: 122
<212> TYPE: DNA
<213> ORGANISM: Artificial Sequence
<220> FEATURE:
<223> OTHER INFORMATION: ADK-Deletion-UTR sense

<400> SEQUENCE: 222
gggccgcccg cgcgcggggt gtgtaaggac gagctctccg acgctgagtg ccagagctag       60
ggagcagttg ctgtggtacc tactgctacc tgggcagacg ctgagcatcc gctgctgcag      120
tc                                                                                            122

<210> SEQ ID NO 223
<211> LENGTH: 122
<212> TYPE: DNA
<213> ORGANISM: Artificial Sequence
<220> FEATURE:
<223> OTHER INFORMATION: ADK-Deletion-UTR antisense

<400> SEQUENCE: 223
gactgcagca gcggatgctc agcgtctgcc caggtagcag taggtaccac agcaactgct      60
ccctagctct ggcactcagc gtcggagagc tcgtccttac acacccgcg cgcgggcggc      120 cc                                                                     122

<210> SEQ ID NO 224
<211> LENGTH: 223
<212> TYPE: DNA
<213> ORGANISM: Artificial Sequence
<220> FEATURE:
<223> OTHER INFORMATION: CREB1-WT-UTR sense

<400> SEQUENCE: 224
tcggcactgg gcggcgctgg ctggctccct ggctgcggct cctcagtcgg cggcggctgc      60
tgctgcctgt ggcccgggcg gctgggagaa gcggagtgtt ggtgagtgac gcggcggagg      120
tgtagtttga cgcggtgtgt tacgtggggg agagaataaa actccagcga gatccgggcc      180
gcgaacgaaa gcagtgacgg aggagcttgt accaccggta tcc                        223

<210> SEQ ID NO 225
<211> LENGTH: 223
<212> TYPE: DNA
<213> ORGANISM: Artificial Sequence
<220> FEATURE:
<223> OTHER INFORMATION: CREB1-WT-UTR antisense

<400> SEQUENCE: 225
ggataccggt ggtacaagct cctccgtcac tgctttcgtt cgcggcccgg atctcgctgg      60
agttttattc tctcccccac gtaacacacc gcgtcaaact acacctccgc cgcgtcactc      120
accaacactc cgcttctccc agccgcccgg gccacaggca gcagcagccg ccgccgactg      180
aggagccgca gccagggagc cagccagcgc cgcccagtgc cga                        223

<210> SEQ ID NO 226
<211> LENGTH: 179
<212> TYPE: DNA
<213> ORGANISM: Artificial Sequence
<220> FEATURE:
<223> OTHER INFORMATION: CREB1-Deletion1-UTR sense

<400> SEQUENCE: 226
tcctggctcc ctggctgcgg ctcctcagtc ggcggcggct gctgctgcct gtggcccgtg      60
agtgacgcgg cggaggtgta gtttgacgcg gtgtgttacg tgggggagag aataaaactc      120
cagcgagatc cgggccgcga acgaaagcag tgacggagga gcttgtacca ccggtatcc       179

<210> SEQ ID NO 227
<211> LENGTH: 179
<212> TYPE: DNA
<213> ORGANISM: Artificial Sequence
<220> FEATURE:
<223> OTHER INFORMATION: CREB1-Deletion1-UTR antisense

<400> SEQUENCE: 227
ggataccggt ggtacaagct cctccgtcac tgctttcgtt cgcggcccgg atctcgctgg      60
agttttattc tctcccccac gtaacacacc gcgtcaaact acacctccgc cgcgtcactc          120
acgggccaca ggcagcagca gccgccgccg actgaggagc cgcagccagg gagccagga          179

<210> SEQ ID NO 228
<211> LENGTH: 212
<212> TYPE: DNA
<213> ORGANISM: Artificial Sequence
<220> FEATURE:
<223> OTHER INFORMATION: CREB1-Deletion2-UTR sense

<400> SEQUENCE: 228
tcggcactgg gcggcgctgg ctggctccct ggctgcggct cctcagtcgg cggcggctgc          60
tgctgcctgt ggcccgggcg gctgggagaa gcggagtgtt ggtgagtgac gcggcggagg          120
tgtagtttga cgcggtgtgt tacgtggggg ctccagcgag atccgggccg cgaacgaaag          180
cagtgacgga ggagcttgta ccaccggtat cc                                        212

<210> SEQ ID NO 229
<211> LENGTH: 212
<212> TYPE: DNA
<213> ORGANISM: Artificial Sequence
<220> FEATURE:
<223> OTHER INFORMATION: CREB1-Deletion2-UTR antisense

<400> SEQUENCE: 229
ggataccggt ggtacaagct cctccgtcac tgctttcgtt cgcggcccgg atctcgctgg          60
agcccccacg taacacaccg cgtcaaacta cacctccgcc gcgtcactca ccaacactcc          120
gcttctccca gccgcccggg ccacaggcag cagcagccgc cgccgactga ggagccgcag          180
ccagggagcc agccagcgcc gcccagtgcc ga                                        212

<210> SEQ ID NO 230
<211> LENGTH: 193
<212> TYPE: DNA
<213> ORGANISM: Artificial Sequence
<220> FEATURE:
<223> OTHER INFORMATION: CREB1-Deletion3-UTR sense

<400> SEQUENCE: 230
tcggcactgg gcggcgctgg ctggctctca tgctgcctgt ggcccgggcg gctgggagaa          60
gcggagtgtt ggtgagtgac gcggcggagg tgtagtttga cgcggtgtgt tacgtggggg          120
agagaataaa actccagcga gatccgggcc gcgaacgaaa gcagtgacgg aggagcttgt          180
accaccggta tcc                                                             193

<210> SEQ ID NO 231
<211> LENGTH: 193
<212> TYPE: DNA
<213> ORGANISM: Artificial Sequence
<220> FEATURE:
<223> OTHER INFORMATION: CREB1-Deletion3-UTR antisense

<400> SEQUENCE: 231
ggataccggt ggtacaagct cctccgtcac tgctttcgtt cgcggcccgg atctcgctgg          60
agttttattc tctcccccac gtaacacacc gcgtcaaact acacctccgc cgcgtcactc          120
accaacactc cgcttctccc agccgcccgg gccacaggca gcatgagagc cagccagcgc          180
cgcccagtgc cga                                                             193

<210> SEQ ID NO 232
<211> LENGTH: 103

-continued

```
<212> TYPE: DNA
<213> ORGANISM: Artificial Sequence
<220> FEATURE:
<223> OTHER INFORMATION: IRSp53-WT-UTR sense

<400> SEQUENCE: 232
gtggtcctgg tctgcgcgcc ttttcctgtt gctgcagttg tcgctttcct caccgccacc      60
cgtgcccctg ctctggtctg tggtgtagcc gggacccagg acc                       103

<210> SEQ ID NO 233
<211> LENGTH: 103
<212> TYPE: DNA
<213> ORGANISM: Artificial Sequence
<220> FEATURE:
<223> OTHER INFORMATION: IRSp53-WT-UTR antisense

<400> SEQUENCE: 233
ggtcctgggt cccggctaca ccacagacca gagcaggggc acgggtggcg gtgaggaaag      60
cgacaactgc agcaacagga aaaggcgcgc agaccaggac cac                       103

<210> SEQ ID NO 234
<211> LENGTH: 88
<212> TYPE: DNA
<213> ORGANISM: Artificial Sequence
<220> FEATURE:
<223> OTHER INFORMATION: IRSp53-Deletion-UTR sense

<400> SEQUENCE: 234
gtggtcctgg tctgcgcgcc agttgtcgct ttcctcaccg ccaccgtgc ccctgctctg       60 gtctgtggtg tagccgggac ccaggacc                                        88

<210> SEQ ID NO 235
<211> LENGTH: 88
<212> TYPE: DNA
<213> ORGANISM: Artificial Sequence
<220> FEATURE:
<223> OTHER INFORMATION: IRSp53-Deletion-UTR antisense

<400> SEQUENCE: 235
ggtcctgggt cccggctaca ccacagacca gagcaggggc acgggtggcg gtgaggaaag      60
cgacaactgg cgcgcagacc aggaccac                                        88
```